United States Patent
Harrop

(10) Patent No.: US 11,427,645 B2
(45) Date of Patent: Aug. 30, 2022

(54) 5T4-TARGETING AGENTS AND METHODS

(71) Applicant: OXFORD BIOMEDICA (UK) LIMITED, Oxford (GB)

(72) Inventor: Richard Harrop, Oxford (GB)

(73) Assignee: OXFORD BIOMEDICA (UK) LIMITED, Oxfordshire (GB)

(*) Notice: Subject to any disclaimer, the term of this patent is extended or adjusted under 35 U.S.C. 154(b) by 422 days.

(21) Appl. No.: 16/490,972

(22) PCT Filed: Mar. 14, 2018

(86) PCT No.: PCT/GB2018/050652
§ 371 (c)(1),
(2) Date: Sep. 4, 2019

(87) PCT Pub. No.: WO2018/167486
PCT Pub. Date: Sep. 20, 2018

(65) Prior Publication Data
US 2020/0010560 A1    Jan. 9, 2020

(30) Foreign Application Priority Data

Mar. 15, 2017 (GB) .................................. 1704084
Dec. 21, 2017 (GB) .................................. 1721603

(51) Int. Cl.
| | | |
|---|---|---|
| C07K 16/30 | (2006.01) | |
| A61K 35/17 | (2015.01) | |
| C07K 14/725 | (2006.01) | |
| C12N 5/0783 | (2010.01) | |
| A61P 35/00 | (2006.01) | |
| A61K 47/68 | (2017.01) | |
| A61P 35/02 | (2006.01) | |
| A61K 9/00 | (2006.01) | |
| A61K 38/17 | (2006.01) | |
| A61K 39/395 | (2006.01) | |
| A61K 45/06 | (2006.01) | |
| C07K 14/705 | (2006.01) | |
| A61K 39/00 | (2006.01) | |

(52) U.S. Cl.
CPC ............ *C07K 16/30* (2013.01); *A61K 9/0019* (2013.01); *A61K 35/17* (2013.01); *A61K 38/1774* (2013.01); *A61K 39/39558* (2013.01); *A61K 45/06* (2013.01); *A61K 47/6857* (2017.08); *A61K 47/6867* (2017.08); *A61K 47/6869* (2017.08); *A61P 35/00* (2018.01); *A61P 35/02* (2018.01); *C07K 14/7051* (2013.01); *C07K 14/70517* (2013.01); *C07K 14/70578* (2013.01); *C12N 5/0636* (2013.01); *A61K 2039/505* (2013.01); *A61K 2039/54* (2013.01); *A61K 2039/545* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
CPC ..... C07K 14/7051–70521; C07K 2319/00–03; C12N 5/636
See application file for complete search history.

(56) References Cited

U.S. PATENT DOCUMENTS

| | | | |
|---|---|---|---|
| 4,690,915 | A | 9/1987 | Rosenberg |
| 5,118,672 | A | 6/1992 | Schinazi et al. |
| 5,199,942 | A | 4/1993 | Gillis |
| 5,869,053 | A | 2/1999 | Stern et al. |
| 6,352,694 | B1 | 3/2002 | June et al. |
| 6,924,123 | B2 | 8/2005 | Kingsman et al. |
| 6,969,598 | B2 | 11/2005 | Olsen et al. |
| 7,056,699 | B2 | 6/2006 | Kingsman et al. |
| 7,067,318 | B2 | 6/2006 | June et al. |
| 7,074,909 | B2* | 7/2006 | Kingsman ............... C07K 16/28 435/325 |
| 7,144,575 | B2 | 12/2006 | June et al. |
| 7,172,869 | B2 | 2/2007 | June et al. |
| 7,572,631 | B2 | 8/2009 | Berenson et al. |
| 7,662,625 | B2* | 2/2010 | Stern ................... G01N 33/5073 435/325 |
| 7,820,174 | B2 | 10/2010 | Wang et al. |
| 8,216,565 | B2 | 7/2012 | Restifo et al. |
| 8,715,947 | B2* | 5/2014 | Stern ........................ A61P 1/16 435/7.23 |

(Continued)

FOREIGN PATENT DOCUMENTS

| | | | |
|---|---|---|---|
| EP | 1152060 A1 | 11/2001 | |
| EP | 1160323 A1 | 12/2001 | |

(Continued)

OTHER PUBLICATIONS

Southall et al., Br. J. Cancer, 61:89-95 (Year: 1990).*
Mcpherson et al., PCR1: A practical approach, Oxford University Press, pp. 1 (1991).
Mulryan et al., Attenuated recombinant vaccinia virus expressing oncofetal antigen (Tumor-associated antigen) 5T4 induces active therapy of established tumors, Molecular Cancer Therapeutics, 1:1129-1137 (Oct. 2002).

(Continued)

*Primary Examiner* — Jessica H Roark
(74) *Attorney, Agent, or Firm* — Marshall, Gerstein & Borun LLP

(57) ABSTRACT

The present invention relates to immunotherapeutic approaches to treating haematological cancers. In particular the invention relates to a method for treating a haematological cancer by targeting the 5T4 antigen. As such, the invention provides a method for treating haematological cancers comprising administering to a subject a 5T4-targeting agent. The invention also provides a 5T4-specific chimeric antigen receptor (CAR) and uses thereof in treating cancers.

Figure 1:
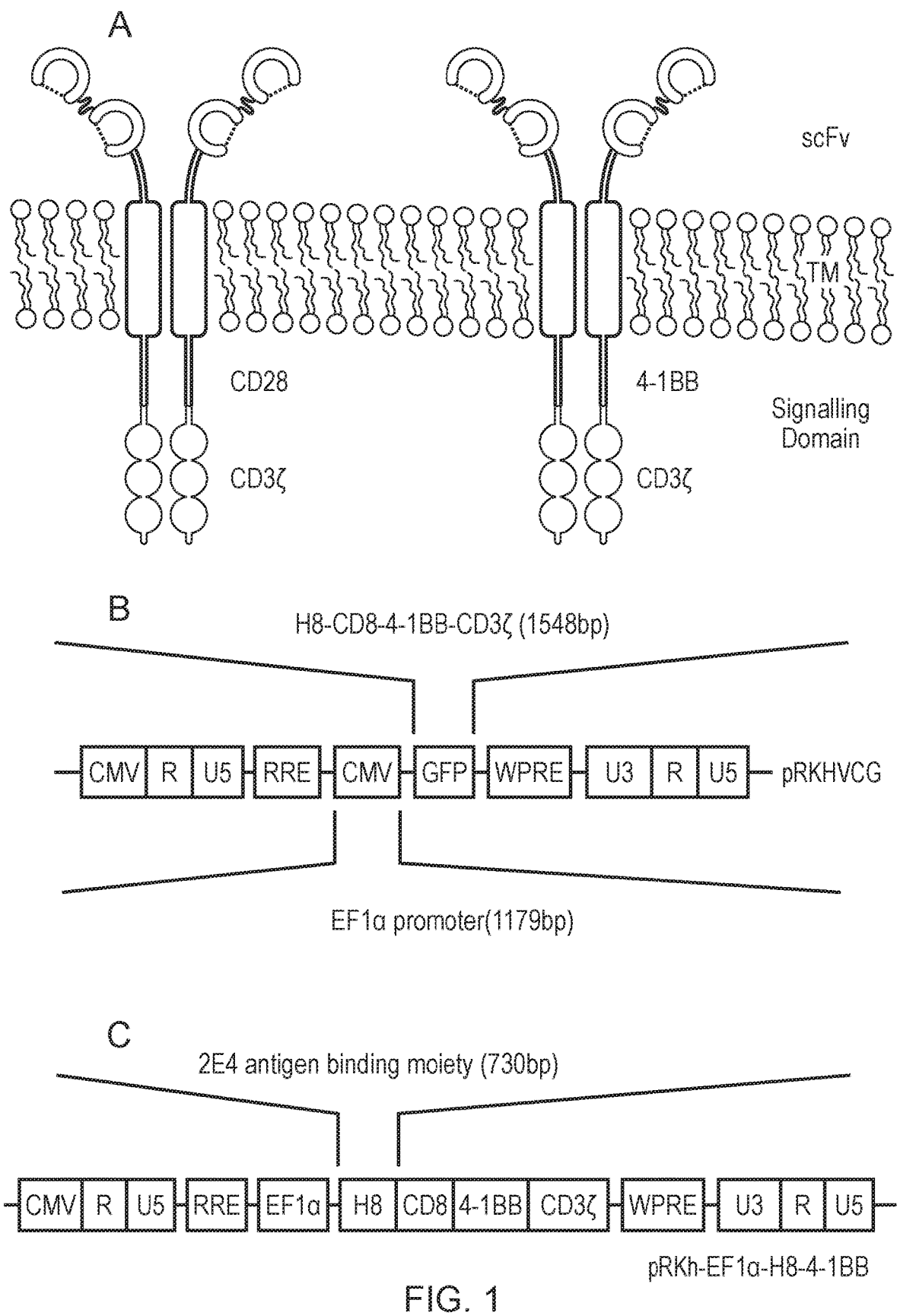

34 Claims, 23 Drawing Sheets
Specification includes a Sequence Listing.

(56) References Cited

U.S. PATENT DOCUMENTS

| | | | |
|---|---|---|---|
| 8,785,601 | B2 | 7/2014 | Rosenberg et al. |
| 9,340,774 | B2* | 5/2016 | Damelin ............... C12N 5/0695 |
| 10,239,949 | B2* | 3/2019 | Bienvenue ............... A61P 35/00 |
| 10,316,080 | B2* | 6/2019 | Smith ................ A61K 47/6843 |
| 2003/0018004 | A1 | 1/2003 | Kingsman et al. |
| 2003/0170238 | A1 | 9/2003 | Gruenberg et al. |
| 2006/0088522 | A1 | 4/2006 | Boghaert et al. |
| 2010/0124534 | A1* | 5/2010 | Harrop ............. G01N 33/57438 424/9.2 |
| 2012/0071350 | A1* | 3/2012 | Damelin ............ G01N 33/5011 506/10 |
| 2013/0274203 | A1 | 10/2013 | Morgan et al. |
| 2016/0185859 | A1 | 6/2016 | Boghaert et al. |
| 2017/0275374 | A1* | 9/2017 | Schiffer-Mannioui ....................... C07K 19/00 |

FOREIGN PATENT DOCUMENTS

| | | |
|---|---|---|
| EP | 1586655 A2 | 10/2005 |
| GB | 2370571 A | 7/2002 |
| GB | 2378704 A | 2/2003 |
| WO | 1989/07947 A1 | 9/1989 |
| WO | 1992/03568 A1 | 3/1992 |
| WO | 1992/21402 A1 | 12/1992 |
| WO | 1994/29348 A2 | 12/1994 |
| WO | 1998/17815 A1 | 4/1998 |
| WO | 1998/55607 A2 | 12/1998 |
| WO | 1998/56919 A2 | 12/1998 |
| WO | 1999/32646 A1 | 7/1999 |
| WO | 2000/29428 A2 | 5/2000 |
| WO | 2001/21201 A2 | 3/2001 |
| WO | 2001/36486 A2 | 5/2001 |
| WO | 2001/62895 A2 | 8/2001 |
| WO | 2001/79518 A2 | 10/2001 |
| WO | 2002/38612 A2 | 5/2002 |
| WO | 2003/38098 A2 | 5/2003 |
| WO | 2003/64665 A2 | 8/2003 |
| WO | 2004/044004 A2 | 5/2004 |
| WO | 2006/031653 A2 | 3/2006 |
| WO | 2006/120473 A2 | 11/2006 |
| WO | 2007/034188 A2 | 3/2007 |
| WO | 2007/106744 A2 | 9/2007 |
| WO | 2009/070003 A2 | 6/2009 |
| WO | 2009/072003 A2 | 6/2009 |
| WO | 2010/007365 A1 | 1/2010 |
| WO | 2010/079339 A2 | 7/2010 |
| WO | 2011/048369 A1 | 4/2011 |
| WO | 2012/059750 A2 | 5/2012 |
| WO | 2012/131527 A1 | 10/2012 |
| WO | 2012/172277 A1 | 12/2012 |
| WO | 2013/068874 A1 | 5/2013 |
| WO | 2013/176915 A1 | 11/2013 |
| WO | 2014/031687 A1 | 2/2014 |
| WO | 2014/055668 A1 | 4/2014 |
| WO | 2015/092440 A1 | 6/2015 |
| WO | 2016/034666 A1 | 3/2016 |
| WO | WO-2016034666 A1 * | 3/2016 ............. A61P 37/04 |
| WO | 2016/196388 A1 | 12/2016 |

OTHER PUBLICATIONS

Myers et al., Isolation of a cDNA encoding 5T4 oncofetal trophoblast glycoprotein. An antigen associated with metastasis contains leucine-rich repeats, J. Biol. Chem., 269:9319-9324 (1994).
Myers et al., Optimal alignments in linear space, Bioinformatics, Cabios, 4:11-17 (1988).
Myers et al., Targeting immune effector molecules to human tumor cells through genetic delivery of 5T4-specific scFv fusion proteins, Cancer Gene. Ther., 9:884-896 (2002).
Obenaus et al., Identification of human T-cell receptors with optimal affinity to cancer antigens using antigen-negative humanized mice, Nat. Biotechnol., 33:402-407 (2015).
Park et al., Treating cancer with genetically engineered T cells, Trends Biotechnol., 29:550-557 (2011).
Parslow et al., Antibody-drug conjugates for cancer therapy, Biomedicines, 4:14 (2016).
Pearson et al., Improved tools for biological sequence comparison, Proc. Natl. Acad. Sci. USA, 85:2444-2448 (1988).
Pearson et al., Rapid and sensitive sequence comparison with FASTP and FASTA, Methods Enzymol., 183:63-98 (1999).
Porter et al., Chimeric antigen receptor T cells persist and induce sustained remissions in relapsed refractory chronic lymphocytic leukemia, Science Translational Medicine, 7:1-13 (2015).
Remington: The Science and Practice of Pharmacy, Lippincott Williams & Wilkins, 21st edition (May 1, 2005).
Richardson et al., A phase 2 study of bortezomib in relapsed, refractory myeloma, N. Engl. J. Med., 348:2609-2617 (2003).
Roberge et al., A strategy for a convergent synthesis of N-linked glycopeptides on a solid support, Science, 269:202-204 (1995).
Rooney et al., Infusion of cytotoxic T cells for the prevention and treatment of Epstein-Barr virus-induced lymphoma in allogeneic transplant recipients, Blood, 92:1549-1555 (1998).
Rosenberg et al., Durable complete responses in heavily pretreated patients with metastatic melanoma using T-cell transfer immunotherapy, Clin. Cancer Res., 17:4550-4557 (2011).
Rosenberg, Cell transfer immunotherapy for metastatic solid cancer—what clinicians need to know, Nat. Rev. Clin. Oncol., 8:557-585 (2011).
Sambrook et al., Molecular cloning: A laboratory manual, 2nd edition, Cold Spring Harbor Laboratory Press, Cold Spring Harbor, NY (1989).
Sapra et al., Long-term tumor regression induced by an Antibody-drug conjugate that targets 5T4, an Oncofetal Antigen Expressed on Tumor-initiating cells, Molecular Cancer Therapeutics, 12:38-47 (2012).
Shaw et al., Glycosylation and epitope mapping of the 5T4 glycoprotein oncofoetal antigen, Biochem. J., 363(part 1):137-145 (2002).
Shaw et al., Isolation of a high affinity scFv from a monoclonal antibody recognising the oncofoetal antigen 5T4, Biochem. Biophys. Acta., 1524:238-246 (2000).
Shibahara et al., Site-directed cleavage of RNA, Nucleic Acids Res., 15:4403-4415 (1987).
Siegel et al., A phase 2 study of single-agent carfilzomib (PX-171-003-A1) in patients with relapsed and refractory multiple myeloma, Blood, 120:2817-2825 (2012).
Starzynska et al., 5T4 oncofetal antigen in gastric carcinoma and its clinical significance, Eur. J. Gastroenterol. Hepatol., 10:479-484 (1998).
Starzynska et al., Prognostic significance of 5T4 oncofetal antigen expression in colorectal carcinoma, Br. J. Cancer, 69:899-902 (1994).
Starzynska et al., The expression of 5T4 antigen in colorectal and gastric carcinoma, Br. J. Cancer., 66:867-9 (1992).
Stern et al., 5T4 oncofoetal antigen: an attractive target for immune intervention in cancer, Cancer Immunology, Immunotherapy, 66:415-426 (2016).
Themeli et al., Generation of tumor-targeted human T lymphocytes from induced pluripotent stem cells for cancer therapy, Nat. Biotechnol., 31:928-933 (2013).
Thompson et al., Clustal W: improving the sensitivity of progressive multiple sequence alignment through sequence weighting, position-specific gap penalties and weight matrix choice, Nucleic Acids Res., 22:4673-4680 (1994).
Tsukahara et al., CD19 target-engineered T-cells accumulate at tumor lesions in human B-cell lymphoma xenograft mouse models, Biochem. Biophys. Res. Commun., 438:84-89 (2013).
Woods et al., Characterization of the murine 5T4 oncofoetal antigen: a target for immunotherapy in cancer, Biochem. J., 366:353-365 (2002).
Wrigley et al., 5T4 oncofetal antigen expression in ovarian carcinoma, Int. J. Gynecol. Cancer, 5:269-274 (1995).
Zhao et al., Structural design of engineered costimulation determines tumor rejection kinetics and persistence of CAR T cells, Cancer Cell, 28:415-428 (2015).

(56) References Cited

OTHER PUBLICATIONS

Zonder et al., A phase 1, multicenter, open-label, dose escalation study of elotuzumab in patients with advanced multiple myeloma, Blood, 120:552-559 (2012).
Al-Taei et al., Overexpression and potential targeting of the oncofoetal antigen 5T4 in malignant pleural mesothelioma, Lung Cancer, 7:312-318 (2012).
Alonso-Camino et al., CARbodies: Human antibodies against cell surface tumor antigens selected from repertoires displayed on T cell chimeric antigen receptors, Mol. Ther. Nucl. Acids, 2:e93 (2013).
Altschul et al., Gapped BLAST and PSI-BLAST: a new generation of protein database search programs, Nucleic Acids Research, 25:3389-3402 (1997).
Amato et al., Vaccination of metastatic renal cancer patients with MVA-5T4: a randomized, double-blind, placebo-controlled phase III study, Clin. Cancer Res., 16:5539-5547 (2010).
Ausubel et al., Current protocols in molecular biology, John Wiley & Sons, New York (1999).
Ausubel et al., Short Protocols in Molecular Biology, 4th edition, John Wiley & Sons, Inc. (1999).
Beckwith et al., The CD37-targeted antibody-drug conjugate IMGN529 is highly active against human CLL and in a novel CD37 transgenic murine leukemia model, Leukemia, 28:1501-1510 (2014).
Berdeja et al., Phase I/II study of the combination of panobinostat and carfilzomib in patients with relapsed/refractory multiple myeloma, Haematologica, 100:670-676 (2015).
Bodansky, Peptide Chemistry, A Practical Textbook, Spring-Verlag, Berlin (1988).
Brash et al., Strontium phosphate transfection of human cells in primary culture: stable expression of the simian virus 40 large-T-antigen gene in primary human bronchial epithelial cells, Mol. Cell. Biol., 7:2013-2034 (1987).
Butterfield, Cancer vaccines, British Medical Journal, 350:h988 (2015).
Castro et al., 5T4 oncofetal antigen is expressed in high risk of relapse childhood pre-B acute lymphoblasitc leukemia and is associated with a more invasive and chemtactic phenotype, Leukemia, 26:1487-1498 (2012).
Chen et al., Expression and purification of two anti-CD19 single chain Fv fragments for targeting lipsomes to CD19-expressing cell, Biochimica. Et. Biophysica. Acta., 1768:21-29 (2007).
Cheng et al., Individualized patient Dosing in phase 1 clinical trials: the role of escalation with overdose control in PNU-214936, J. Clin. Oncol., 22:602-609 (2004).
Coffin et al., Retroviruses, Cold Spring Harbour Laboratory Press Eds., 758-763 (1997).
Creighton, Proteins Structures and Molecular Principles, W H Freeman & Co., New York, NY (1992).
Damelin et al., Delineation of a cellular hierarchy in lung cancer reveals an oncofetal antigen expressed on tumor-initiating cells, Cancer Research, 71:4236-4246 (2011).
Davila et al., CD19 CAR-targeted T cells induce long-term remission and B bell aplasia in an immunocompetent mouse model of B cell acute lymphoblastic leukemia, PLoS One, 8:e61338 (2013).
Dudley et al., Generation of tumor-infiltrating lymphocyte cultures for use in adoptive transfer therapy for melanoma patients, J. Immunother., 26:332-342 (2003).
Dudley et al., Microsatellite instability as a biomarker for PD-1 blockade, Clin. Cancer Res., 16:6122-6131 (2010).
Fedorov et al., PD-1- and CTLA-4-based inhibitory chimeric antigen receptors (iCARs) divert off-target immunotherapy responses, Sci. Transl. Med., 5:215ra172 (2013).
Fonseca et al., International myeloma working group molecular classification of multiple myeloma: spotlight review, Leukemia, 23:2210-2221 (2009).
Forsberg et al., Therapy of human non-small-cell lung carcinoma using antibody targeting of a modified superantigen, Br. J. Cancer, 85:129-136 (2001).
Freed et al., Culture of organized cell communities, Advanced Drug Delivery Reviews, 33:15-30 (1998).
Freeman et al., Immunotherapy in Chronic Lymphocyctice Leukaemia (CLL), Current Hematologic Malignancy Reports, 11:29-36 (2015).
Genbank accession No. AJ012160 Mus musculus 5T4 oncofetal trophoblast glycoprotein gene (Apr. 15, 2005).
Genbank accession No. Z29083 *Homo sapiens* 5T4 gene for 5T4 oncofoetal antigen (Nov. 2006).
Griffiths et al., Expression of the 5T4 oncofoetal antigen in renal cell carcinoma: a potential target for T-cell-based immunotherapy, British Journal of Cancer, 93:670-677 (2005).
Guschlbauer et al., Nucleoside conformation is determined by the electronegativity of the sugar substituent, Nucleic Acids Res, 4:1933 (1977).
Guthrie et al., Guide to yeast genetics and molecular biology, Methods in Enzymology, Academic Press Inc., p. 194, (1991).
Harrop et al., Analysis of pre-treatment markers predictive of treatment benefit for the therapeutic cancer vaccine MVA-5T4 (TroVax), Cancer Immunol. Immunother., 61:2283-2294 (2012).
Harrop et al., Vaccination of castration-resistant prostate cancer patients with TroVax (MVA-5T4) in combination with docetaxel: a randomized phase II trial, Cancer Immunol. Immunother., 62:1511-1520 (2013).
Hawkins et al., A randomized phase II/III study of naptumomab estafenatox + IFN(Alpha) versus IFN(Alpha) in renal cell carcinoma: final analysis with baseline biomarker subgroup and trend analysis, Clin. Cancer Research, 22:3172-3181 (2016).
He et al., Trophoblast glycoprotein promotes pancreatic ductal adenocarcinoma cell metastasis through Wnt/planar cell polarity signaling, Molecular Medicine Reports, 12:503-509 (2015).
Hinrichs et al., Reassessing target antigens for adoptive T cell therapy, Nature Biotechnology, 31:999-1008 (2013).
Hole et al., A 72 kD trophoblast glycoprotein defined by a monoclonal antibody, Br. J. Cancer, 57:239-246 (1988).
Holm et al., Dali: a network tool for protein structure comparison, Trends Biochem. Sci., 20:478-480 (1995).
Holm et al., Protein structure comparison by alignment of distance matrices, J. Mol. Biol., 233:123-138 (1993).
Holm et al., Touring protein fold space with Dali/FSSP, Nucleic Acid Res., 26:316-319 (1998).
Innis et al., , PCR protocols: A guide to methods and applications, Academic Press, San Diego, California (1990).
International Preliminary Report on Patentability for Corresponding International Application No. PCT/GB2018/050652, dated Sep. 26, 2019, 14 pages.
International Search Report and Written Opinion for Corresponding International Application No. PCT/GB2018/050652, dated Aug. 23, 2018, 20 pages.
Jones et al., Investigation of expression of 5T4 antigen in cervical cancer, British Journal Cancer, 61:96-100 (1990).
June et al., Engineering lymphocyte subsets: tools, trials and tribulations, Nat. Rev. Immunol., 9:704-716 (2009).
Kerk et al., 5T4-targeted therapy ablates cancer stem cells and prevents recurrence of head and neck squamous cel carcinoma, Clinical Cancer Research, 23:2516-2527 (2017).
King et al., Organisation of the mouse and human 5T4 oncofoetal leucine-rich glycoprotein genes and expression in foetal and adult murine tissues, Biochim. Biophys. Acta., 1445:257-2770 (1999).
Koste et al., T-cell receptor transfer into human T cells with ecotropic retroviral vectors, Gene. Therapy., 21:533-538 (2014).
Lokhorst et al., Targeting CD38 with daratumumab monotherapy in multiple myeloma, N. Engl. J. Med., 373:1207-1219 (2015).
Lundblad, Chemical reagents for protein modification, 3rd edition, CRC Press (2004).
Lynn et al., High affinity FR(Beta)-specific CAR T cells eradicate AML and normal myeloid lineage without HSC toxicity, Leukemia, 3096:1355-1364 (2016).
McGinn O J et al., Targeting the 5T4 oncofetal glycoprotein with an antibody drug conjugate (A1mcMMAF) improves survival in pateint-derived xenofraft models of acute lymphoblastic leukemia, Haematolgica, 102(6):1075-1084 (2017).

* cited by examiner

SEQUENCE LISTING

```
<160> NUMBER OF SEQ ID NOS: 14

<210> SEQ ID NO 1
<211> LENGTH: 515
<212> TYPE: PRT
<213> ORGANISM: Artificial Sequence
<220> FEATURE:
<223> OTHER INFORMATION: 5T4-specific CAR sequence

<400> SEQUENCE: 1

Met Gly Val Leu Leu Thr Gln Arg Thr Leu Leu Ser Leu Val Leu Ala
1               5                   10                  15

Leu Leu Phe Pro Ser Met Ala Ser Met Glu Val Gln Leu Gln Gln Ser
            20                  25                  30
```

```
Gly Pro Asp Leu Val Lys Pro Ala Ser Val Lys Ile Ser Cys Lys
        35                  40                  45

Ala Ser Gly Tyr Ser Phe Thr Gly Tyr Tyr Met His Trp Val Lys Gln
50                  55                  60

Ser His Gly Lys Ser Leu Glu Trp Ile Gly Arg Ile Asn Pro Asn Asn
65                  70                  75                  80

Gly Val Thr Leu Tyr Asn Gln Lys Phe Lys Asp Lys Ala Ile Leu Thr
                85                  90                  95

Val Asp Lys Ser Ser Thr Thr Ala Tyr Met Glu Leu Arg Ser Leu Thr
            100                 105                 110

Ser Glu Asp Ser Ala Val Tyr Tyr Cys Ala Arg Ser Thr Met Ile Thr
            115                 120                 125

Asn Tyr Val Met Asp Tyr Trp Gly Gln Val Thr Ser Val Thr Val Ser
130                 135                 140

Ser Gly Gly Gly Gly Ser Gly Gly Gly Gly Thr Gly Gly Gly Gly Ser
145                 150                 155                 160

Ser Ile Val Met Thr Gln Thr Pro Thr Phe Leu Leu Val Ser Ala Gly
            165                 170                 175

Asp Arg Val Thr Ile Thr Cys Lys Ala Ser Gln Ser Val Ser Asn Asp
            180                 185                 190

Val Ala Trp Tyr Gln Gln Lys Pro Gly Gln Ser Pro Thr Leu Leu Ile
        195                 200                 205

Ser Tyr Thr Ser Ser Arg Tyr Ala Gly Val Pro Asp Arg Phe Ile Gly
        210                 215                 220

Ser Gly Tyr Gly Thr Asp Phe Thr Phe Thr Ile Ser Thr Leu Gln Ala
225                 230                 235                 240

Glu Asp Leu Ala Val Tyr Phe Cys Gln Gln Asp Tyr Asn Ser Pro Pro
                245                 250                 255

Thr Phe Gly Gly Gly Thr Lys Leu Glu Ile Lys Arg Ala Ala Ala Leu
            260                 265                 270

Ser Asn Ser Ile Met Tyr Phe Ser His Phe Val Pro Val Phe Leu Pro
            275                 280                 285

Ala Lys Pro Thr Thr Thr Pro Ala Pro Arg Pro Pro Thr Pro Ala Pro
        290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
                325                 330                 335

Ile Tyr Ile Trp Ala Pro Leu Ala Gly Thr Cys Gly Val Leu Leu Leu
            340                 345                 350

Ser Leu Val Ile Thr Leu Tyr Cys Lys Arg Gly Arg Lys Lys Leu Leu
            355                 360                 365

Tyr Ile Phe Lys Gln Pro Phe Met Arg Pro Val Gln Thr Thr Gln Glu
370                 375                 380

Glu Asp Gly Cys Ser Cys Arg Phe Pro Glu Glu Glu Gly Gly Cys
385                 390                 395                 400

Glu Leu Leu Arg Val Lys Phe Ser Arg Ser Ala Asp Ala Pro Ala Tyr
                405                 410                 415

Gln Gln Gly Gln Asn Gln Leu Tyr Asn Glu Leu Asn Leu Gly Arg Arg
            420                 425                 430

Glu Glu Tyr Asp Val Leu Asp Lys Arg Arg Gly Arg Asp Pro Glu Met
            435                 440                 445
```

Gly Gly Lys Pro Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
                500                 505                 510

Pro Pro Arg
        515

<210> SEQ ID NO 2
<211> LENGTH: 24
<212> TYPE: PRT
<213> ORGANISM: Artificial Sequence
<220> FEATURE:
<223> OTHER INFORMATION: Oncostatin M leader

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser
            20

<210> SEQ ID NO 3
<211> LENGTH: 244
<212> TYPE: PRT
<213> ORGANISM: Artificial Sequence
<220> FEATURE:
<223> OTHER INFORMATION: H8 anti5T4 domain

<400> SEQUENCE: 3

Met Glu Val Gln Leu Gln Gln Ser Gly Pro Asp Leu Val Lys Pro Gly
1               5                   10                  15

Ala Ser Val Lys Ile Ser Cys Lys Ala Ser Gly Tyr Ser Phe Thr Gly
            20                  25                  30

Tyr Tyr Met His Trp Val Lys Gln Ser His Gly Lys Ser Leu Glu Trp
        35                  40                  45

Ile Gly Arg Ile Asn Pro Asn Asn Gly Val Thr Leu Tyr Asn Gln Lys
    50                  55                  60

Phe Lys Asp Lys Ala Ile Leu Thr Val Asp Lys Ser Ser Thr Thr Ala
65                  70                  75                  80

Tyr Met Glu Leu Arg Ser Leu Thr Ser Glu Asp Ser Ala Val Tyr Tyr
                85                  90                  95

Cys Ala Arg Ser Thr Met Ile Thr Asn Tyr Val Met Asp Tyr Trp Gly
            100                 105                 110

Gln Val Thr Ser Val Thr Val Ser Ser Gly Gly Gly Ser Gly Gly
        115                 120                 125

Gly Gly Thr Gly Gly Gly Ser Ser Ile Val Met Thr Gln Thr Pro
    130                 135                 140

Thr Phe Leu Leu Val Ser Ala Gly Asp Arg Val Thr Ile Thr Cys Lys
145                 150                 155                 160

Ala Ser Gln Ser Val Ser Asn Asp Val Ala Trp Tyr Gln Gln Lys Pro
                165                 170                 175

Gly Gln Ser Pro Thr Leu Leu Ile Ser Tyr Thr Ser Ser Arg Tyr Ala
            180                 185                 190

Gly Val Pro Asp Arg Phe Ile Gly Ser Gly Tyr Gly Thr Asp Phe Thr
        195                 200                 205

```
Phe Thr Ile Ser Thr Leu Gln Ala Glu Asp Leu Ala Val Tyr Phe Cys
        210                 215                 220

Gln Gln Asp Tyr Asn Ser Pro Pro Thr Phe Gly Gly Gly Thr Lys Leu
225                 230                 235                 240

Glu Ile Lys Arg

<210> SEQ ID NO 4
<211> LENGTH: 3
<212> TYPE: PRT
<213> ORGANISM: Artificial Sequence
<220> FEATURE:
<223> OTHER INFORMATION: linker

<400> SEQUENCE: 4

Ala Ala Ala
1

<210> SEQ ID NO 5
<211> LENGTH: 65
<212> TYPE: PRT
<213> ORGANISM: Artificial Sequence
<220> FEATURE:
<223> OTHER INFORMATION: CD8 hinge

<400> SEQUENCE: 5

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60

Asp
65

<210> SEQ ID NO 6
<211> LENGTH: 24
<212> TYPE: PRT
<213> ORGANISM: Artificial Sequence
<220> FEATURE:
<223> OTHER INFORMATION: CD8 transmembrane region

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 42
<212> TYPE: PRT
<213> ORGANISM: Artificial Sequence
<220> FEATURE:
<223> OTHER INFORMATION: 41BB costimulatory domain

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30
```

```
<210> SEQ ID NO 8
<211> LENGTH: 113
<212> TYPE: PRT
<213> ORGANISM: Artificial Sequence
<220> FEATURE:
<223> OTHER INFORMATION: CD3 zeta stimulatory domain

<400> SEQUENCE: 8

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 9
<211> LENGTH: 1548
<212> TYPE: DNA
<213> ORGANISM: Artificial Sequence
<220> FEATURE:
<223> OTHER INFORMATION: codon-optimised sequence encoding the 5T4-CAR
      protein

<400> SEQUENCE: 9
atgggagtgc tgctgaccca gagaaccctg ctgtctctgg tgctggccct gctgttccct      60
agcatggcca gcatggaagt gcagctgcag cagagcggcc ctgacctcgt gaaacctggc     120
gcctccgtga agatcagctg caaggccagc ggctacagct tcaccggcta ctacatgcac     180
tgggtcaagc agagccacgg caagagcctg aatggatcg gccggatcaa ccccaacaac      240
ggcgtgaccc tgtacaacca gaagttcaag gacaaggcca tcctgaccgt ggacaagagc     300
agcaccaccg cctacatgga actgcggagc ctgaccagcg aggacagcgc cgtgtactac     360
tgcgcccggt ccaccatgat caccaactac gtgatggact actggggcca agtgaccagc     420
gtgaccgtgt ctgcggagg cggaggatct ggcggcggag aacaggcgg agggggatct      480 agcatcgtga tgacccagac ccccacctc ctgctggtgt ctgccggcga cagagtgacc      540
atcacatgca aggcctccca gagcgtgtcc aacgacgtgg cctggtatca gcagaagcct     600
ggccagagcc caccctgct gattagctac accagctcca gatatgccgg cgtgcccgac     660
agattcatcg gcagcggcta tgcaccgac ttcaccttca ccatcagcac actgcaggcc      720
gaggacctgg ctgtgtactt ctgtcagcaa gactacaaca gccccctac cttcggcgga     780 ggcaccaagc tggaaatcaa gagagccgcc gctctgagca cagcatcat gtacttcagc     840 cacttcgtgc ccgtgtttct gccgccaag cctaccacaa ccctgccc tagacctcct       900 accccagcc ctacaatcgc cagccagcct ctgtctctga ggcccgaggc ttgtagacct      960
```

```
gctgctggcg gagccgtgca caccagagga ctggatttcg cctgcgacat ctacatctgg    1020 gccctctgg ccggcacatg tggcgtgctg ctgctgagcc tcgtgatcac cctgtactgc    1080
aagcggggca gaaagaagct gctgtacatc ttcaagcagc ccttcatgcg gcccgtgcag    1140
accacccagg aagaggacgg ctgctcctgc agattccccg aggaagaaga aggcggctgc    1200
gagctgctga gagtgaagtt cagcagatcc gccgacgccc ctgcctacca gcagggacag    1260
aatcagctgt acaacgagct gaacctgggc agacgggaag agtacgacgt gctggacaag    1320
cggagaggca gggaccctga tgggcggc aagcccagaa gaaagaaccc ccaggaaggc       1380
ctgtataacg aactgcagaa agacaagatg gccgaggcct acagcgagat cggaatgaag    1440
ggcgagcgga gaaggcaa gggccacgat ggactgtacc agggcctgag caccgccacc      1500
aaggacacct atgacgccct gcacatgcag gctctgcccc ccagatga                 1548
```

<210> SEQ ID NO 10
<211> LENGTH: 1179
<212> TYPE: DNA
<213> ORGANISM: Artificial Sequence
<220> FEATURE:
<223> OTHER INFORMATION: EF1alpha promoter sequence

<400> SEQUENCE: 10

```
ggctccggtg cccgtcagtg ggcagagcgc acatcgccca cagtccccga gaagttgggg    60
ggaggggtcg gcaattgaac cggtgcctag agaaggtggc gcggggtaaa ctgggaaagt    120
gatgtcgtgt actggctccg ccttttttccc gagggtgggg gagaaccgta tataagtgca   180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccacct ggctgcagta cgtgattctt gatcccgagc ttcgggttgg aagtgggtgg    360
gagagttcga ggccttgcgc ttaaggagcc cttcgcctc gtgcttgagt tgaggcctgg    420
cctgggcgct ggggccgccg cgtgcgaatc tggtggcacc ttcgcgcctg tctcgctgct    480
ttcgataagt ctctagccat ttaaaatttt tgatgacctg ctgcgacgct ttttttctgg    540
caagatagtc ttgtaaatgc gggccaagat ctgcacactg gtatttcggt ttttggggcc    600
gcgggcggcg acggggcccg tgcgtcccag cgcacatgtt cggcgaggcg ggcctgcga    660 gcgcggccac cgagaatcgg acggggtag tctcaagctg gccggcctgc tctggtgcct     720
ggcctcgcgc cgccgtgtat cgccccgccc tgggcggcaa ggctggcccg gtcggcacca    780
gttgcgtgag cggaaagatg gccgcttccc ggccctgctg cagggagctc aaaatggagg    840
acgcggcgct cgggagagcg ggcgggtgag tcacccacac aaaggaaaag gccttttccg    900
tcctcagccg tcgcttcatg tgactccacg gagtaccggg gcgcgtccag gcacctcgat    960
tagttctcga gcttttggag tacgtcgtct ttaggttggg gggaggggtt ttatgcgatg    1020
gagtttcccc acactgagtg ggtggagact gaagttaggc cagcttggca cttgatgtaa    1080
ttctccttgg aatttgccct ttttgagttt ggatcttggt tcattctcaa gcctcagaca    1140
gtggttcaaa gtttttttct tccatttcag gtgtcgtga                           1179
```

<210> SEQ ID NO 11
<211> LENGTH: 243
<212> TYPE: PRT
<213> ORGANISM: Artificial Sequence
<220> FEATURE:
<223> OTHER INFORMATION: 2E4 anti5T4 domain

<400> SEQUENCE: 11

```
Met Glu Val Gln Leu Gln Gln Ser Gly Pro Glu Leu Val Lys Pro Gly
1               5                   10                  15

Ala Ser Val Lys Ile Ser Cys Lys Ala Ser Gly Tyr Ser Phe Thr Gly
            20                  25                  30

Tyr Tyr Met His Trp Val Lys Gln Ser His Val Lys Ser Leu Glu Trp
            35                  40                  45

Ile Gly Arg Ile Asn Pro Tyr Asn Gly Ala Thr Thr Tyr Asn Gln Asp
50                  55                  60

Phe Lys Asp Lys Ala Ser Leu Thr Val Asp Lys Ser Ser Ser Thr Ala
65                  70                  75                  80

Ser Met Glu Leu His Ser Leu Thr Ser Glu Asp Ser Ala Val Tyr Tyr
                85                  90                  95

Cys Ala Leu Ser Thr Met Ile Thr Thr Ala Trp Phe Ala Tyr Trp Gly
                100                 105                 110

Gln Gly Thr Leu Val Thr Val Ser Pro Gly Gly Gly Ser Gly Gly
                115                 120                 125

Gly Gly Thr Gly Gly Gly Ser Asn Phe Val Met Thr Gln Thr Pro
        130                 135                 140

Lys Phe Leu Leu Ala Ser Ala Gly Asp Arg Val Thr Ile Ser Cys Lys
145                 150                 155                 160

Ala Ser Gln Ser Val Ser Asn Asp Val Gly Trp Tyr Gln Gln Lys Pro
            165                 170                 175

Gly Gln Ser Pro Lys Leu Leu Ile Tyr Phe Ala Ser Asn Arg Tyr Thr
            180                 185                 190

Gly Val Pro Asp Arg Phe Ile Gly Ser Gly Tyr Gly Thr Asp Phe Thr
            195                 200                 205

Phe Thr Ile Ser Thr Val Gln Ala Glu Asp Leu Ala Val Tyr Phe Cys
            210                 215                 220

Gln Gln Asp Tyr Ser Ser Pro Phe Thr Phe Gly Ser Gly Thr Lys Leu
225                 230                 235                 240

Glu Ile Lys

<210> SEQ ID NO 12
<211> LENGTH: 243
<212> TYPE: PRT
<213> ORGANISM: Artificial Sequence
<220> FEATURE:
<223> OTHER INFORMATION: 2E4 antibody sequence

<400> SEQUENCE: 12

Met Glu Val Gln Leu Gln Gln Ser Gly Pro Glu Leu Val Lys Pro Gly
1               5                   10                  15

Ala Ser Val Lys Ile Ser Cys Lys Ala Ser Gly Tyr Ser Phe Thr Gly
            20                  25                  30

Tyr Tyr Met His Trp Val Lys Gln Ser His Val Lys Ser Leu Glu Trp
            35                  40                  45

Ile Gly Arg Ile Asn Pro Tyr Asn Gly Ala Thr Thr Tyr Asn Gln Asp
50                  55                  60

Phe Lys Asp Lys Ala Ser Leu Thr Val Asp Lys Ser Ser Ser Thr Ala
65                  70                  75                  80

Ser Met Glu Leu His Ser Leu Thr Ser Glu Asp Ser Ala Val Tyr Tyr
                85                  90                  95

Cys Ala Leu Ser Thr Met Ile Thr Thr Ala Trp Phe Ala Tyr Trp Gly
                100                 105                 110
```

```
Gln Gly Thr Leu Val Thr Val Ser Pro Gly Gly Gly Ser Gly Gly
            115                 120                 125

Gly Gly Thr Gly Gly Gly Ser Asn Phe Val Met Thr Gln Thr Pro
130                 135                 140

Lys Phe Leu Leu Ala Ser Ala Gly Asp Arg Val Thr Ile Ser Cys Lys
145                 150                 155                 160

Ala Ser Gln Ser Val Ser Asn Asp Val Gly Trp Tyr Gln Lys Pro
            165                 170                 175

Gly Gln Ser Pro Lys Leu Leu Ile Tyr Phe Ala Ser Asn Arg Tyr Thr
            180                 185                 190

Gly Val Pro Asp Arg Phe Ile Gly Ser Gly Tyr Gly Thr Asp Phe Thr
            195                 200                 205

Phe Thr Ile Ser Thr Val Gln Ala Glu Asp Leu Ala Val Tyr Phe Cys
    210                 215                 220

Gln Gln Asp Tyr Ser Ser Pro Phe Thr Phe Gly Ser Gly Thr Lys Leu
225                 230                 235                 240

Glu Ile Lys

<210> SEQ ID NO 13
<211> LENGTH: 514
<212> TYPE: PRT
<213> ORGANISM: Artificial Sequence
<220> FEATURE:
<223> OTHER INFORMATION: 5T4-specific CAR sequence

<400> SEQUENCE: 13

Met Gly Val Leu Leu Thr Gln Arg Thr Leu Leu Ser Leu Val Leu Ala
1               5                   10                  15

Leu Leu Phe Pro Ser Met Ala Ser Met Glu Val Gln Leu Gln Gln Ser
            20                  25                  30

Gly Pro Glu Leu Val Lys Pro Gly Ala Ser Val Lys Ile Ser Cys Lys
        35                  40                  45

Ala Ser Gly Tyr Ser Phe Thr Gly Tyr Tyr Met His Trp Val Lys Gln
    50                  55                  60

Ser His Val Lys Ser Leu Glu Trp Ile Gly Arg Ile Asn Pro Tyr Asn
65                  70                  75                  80

Gly Ala Thr Thr Tyr Asn Gln Asp Phe Lys Asp Lys Ala Ser Leu Thr
                85                  90                  95

Val Asp Lys Ser Ser Ser Thr Ala Ser Met Glu Leu His Ser Leu Thr
            100                 105                 110

Ser Glu Asp Ser Ala Val Tyr Tyr Cys Ala Leu Ser Thr Met Ile Thr
        115                 120                 125

Thr Ala Trp Phe Ala Tyr Trp Gly Gln Gly Thr Leu Val Thr Val Ser
    130                 135                 140

Pro Gly Gly Gly Gly Ser Gly Gly Gly Gly Thr Gly Gly Gly Gly Ser
145                 150                 155                 160

Asn Phe Val Met Thr Gln Thr Pro Lys Phe Leu Leu Ala Ser Ala Gly
                165                 170                 175

Asp Arg Val Thr Ile Ser Cys Lys Ala Ser Gln Ser Val Ser Asn Asp
            180                 185                 190

Val Gly Trp Tyr Gln Gln Lys Pro Gly Gln Ser Pro Lys Leu Leu Ile
        195                 200                 205

Tyr Phe Ala Ser Asn Arg Tyr Thr Gly Val Pro Asp Arg Phe Ile Gly
    210                 215                 220

Ser Gly Tyr Gly Thr Asp Phe Thr Phe Thr Ile Ser Thr Val Gln Ala
```

225                 230                 235                 240
    Glu Asp Leu Ala Val Tyr Phe Cys Gln Gln Asp Tyr Ser Ser Pro Phe
                        245                 250                 255

Thr Phe Gly Ser Gly Thr Lys Leu Glu Ile Lys Ala Ala Ala Leu Ser
                        260                 265                 270

Asn Ser Ile Met Tyr Phe Ser His Phe Val Pro Val Phe Leu Pro Ala
                        275                 280                 285

Lys Pro Thr Thr Thr Pro Ala Pro Arg Pro Pro Thr Pro Ala Pro Thr
    290                 295                 300

Ile Ala Ser Gln Pro Leu Ser Leu Arg Pro Glu Ala Cys Arg Pro Ala
    305                 310                 315                 320

Ala Gly Gly Ala Val His Thr Arg Gly Leu Asp Phe Ala Cys Asp Ile
                        325                 330                 335

Tyr Ile Trp Ala Pro Leu Ala Gly Thr Cys Gly Val Leu Leu Leu Ser
                        340                 345                 350

Leu Val Ile Thr Leu Tyr Cys Lys Arg Gly Arg Lys Lys Leu Leu Tyr
                        355                 360                 365

Ile Phe Lys Gln Pro Phe Met Arg Pro Val Gln Thr Thr Gln Glu Glu
    370                 375                 380

Asp Gly Cys Ser Cys Arg Phe Pro Glu Glu Glu Glu Gly Gly Cys Glu
    385                 390                 395                 400

Leu Leu Arg Val Lys Phe Ser Arg Ser Ala Asp Ala Pro Ala Tyr Gln
                        405                 410                 415

Gln Gly Gln Asn Gln Leu Tyr Asn Glu Leu Asn Leu Gly Arg Arg Glu
                        420                 425                 430

Glu Tyr Asp Val Leu Asp Lys Arg Arg Gly Arg Asp Pro Glu Met Gly
                        435                 440                 445

Gly Lys Pro Arg Arg Lys Asn Pro Gln Glu Gly Leu Tyr Asn Glu Leu
    450                 455                 460

Gln Lys Asp Lys Met Ala Glu Ala Tyr Ser Glu Ile Gly Met Lys Gly
    465                 470                 475                 480

Glu Arg Arg Arg Gly Lys Gly His Asp Gly Leu Tyr Gln Gly Leu Ser
                        485                 490                 495

Thr Ala Thr Lys Asp Thr Tyr Asp Ala Leu His Met Gln Ala Leu Pro
                        500                 505                 510

Pro Arg

<210> SEQ ID NO 14
<211> LENGTH: 730
<212> TYPE: DNA
<213> ORGANISM: Artificial Sequence
<220> FEATURE:
<223> OTHER INFORMATION: sequence encoding the 2E4 antigen binding
      moiety

<400> SEQUENCE: 14
atggaagtgc agctgcagca gtctggcccc gagctcgtga aacctggcgc ctccgtgaag     60
atcagctgca aggccagcgg ctacagcttc accggctact acatgcactg ggtcaagcag    120
agccacgtga agtccctgga atggatcggc cggatcaacc cctacaacgg cgccaccacc    180
tacaaccagg acttcaagga caaggcctcc ctgaccgtgg acaagagcag cagcaccgcc    240
agcatggaac tgcacagcct gaccagcgag gacagcgccg tgtactactg tgccctgagc    300
accatgatca ccaccgcttg gtttgcctac tggggccagg gcacactcgt gaccgtgtct    360
ccaggaggcg gaggatctgg cggcggagga acaggcggag ggggatctaa cttcgtgatg    420

-continued

```
acccagaccc ccaagttcct gctggcctct gccggcgaca gagtgaccat cagctgcaag      480
gccagccaga gcgtgtccaa cgacgtgggc tggtatcagc agaagcccgg ccagagcccc      540
aagctgctga tctacttcgc cagcaaccgg tacaccggcg tgcccgacag attcatcggc      600
agcggctacg gcaccgactt caccttcacc atcagcaccg tgcaggccga ggacctggcc      660
gtgtacttct gtcagcaaga ctacagcagc cctttcacct tcggctccgg caccaagctg      720
gaaatcaagg                                                             730
```

5T4-TARGETING AGENTS AND METHODS

CROSS-REFERENCE TO RELATED APPLICATIONS

This application is a U.S. National Phase of International Patent Application No. PCT/GB2018/050652, filed Mar. 14, 2018, which claims benefit of Application No. 1721603.7 filed on Dec. 21, 2017, in the United Kingdom and Application No. 1704084.1 filed on Mar. 15, 2017, in the United Kingdom.

INCORPORATION BY REFERENCE OF MATERIALS SUBMITTED ELECTRONICALLY

This application contains, as a separate part of the disclosure, a Sequence Listing in computer readable form (Filename: 53951_Seqlisting.txt; Size: 23,894 bytes; Created: Aug. 20, 2019), which is incorporated herein by reference in its entirety.

FIELD OF THE INVENTION

The present invention relates to immunotherapeutic approaches to treating haematological cancers. In particular the invention relates to a method for treating a haematological cancer by targeting the 5T4 antigen. As such, the invention provides a method for treating haematological cancers comprising administering to a subject a 5T4-targeting agent. The invention also provides a 5T4-specific chimeric antigen receptor (CAR) and uses thereof in treating cancers.

BACKGROUND TO THE INVENTION

Haematological cancers may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukaemias, and myeloma are from the lymphoid line, while acute and chronic myelogenous leukaemia, myelodysplastic syndromes and myeloproliferative diseases are myeloid in origin.

Haematologic cancers may cause a number of symptoms. Several of the most common are weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function). Certain symptoms are more likely to occur with some cancers than others. For example, bone pain is more frequently found in myeloma, and enlarged lymph nodes are most common with lymphoma. The specific effects of the enlarged lymph nodes depend on the location and size of these nodes.

Taken together, haematological malignancies account for 9.5% of new cancer diagnoses in the United States and 30,000 patients in the UK are diagnosed each year. It may be expected that the prevalence of haematological cancers may increase with their attendant consequences as a result of aging of the population and inability to invoke prevention in most cases.

Some therapeutic options for treating haematological cancers are currently available, for example chemotherapy, radiotherapy, immunotherapy and bone marrow transplant. There is, however, a need in the art for alternative ways of treating or preventing haematological cancers.

SUMMARY OF THE INVENTION

The present inventors have surprisingly found that the antigen 5T4 is expressed on cells in haematological cancers, and therefore targeting 5T4 provides an option for the treatment or prevention of haematological cancers.

As such, the invention provides a method for treating or preventing a haematological cancer in a subject comprising administering a 5T4-targeting agent to the subject.

In a further aspect the invention provides a 5T4-targeting agent for use in the treatment or prevention of a haematological cancer.

Also provided is use of a 5T4-targeting agent in the manufacture of a medicament for treating or preventing a haematological cancer, and use of a 5T4-targeting agent for treating or preventing a haematological cancer.

The invention also provides a 5T4-specific chimeric antigen receptor (CAR) and cells expressing 5T4-specific CARs, and uses thereof in the treatment or prevention of cancer, in particular a haematological cancer.

In an alternative aspect the invention provides a cancer vaccine targeting 5T4 for the treatment or prevention of a haematological cancer.

Other aspects of the present invention are presented in the accompanying claims and in the following description and discussion. These aspects may be presented under separate section headings. However, it is to be understood that the teachings under each section heading are not necessarily limited to that particular section heading.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry).

Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). These documents are incorporated herein by reference.

LIST OF FIGURE LEGENDS

FIG. 1: Schematic of 5T4-CAR-T constructs. These include variations in the α-5T4 scFv (H8 or 2E4); in the co-stimulatory domain (CD28 or 4-1BB); or in the promoter region (CMV or EF1α).

Figure 2:
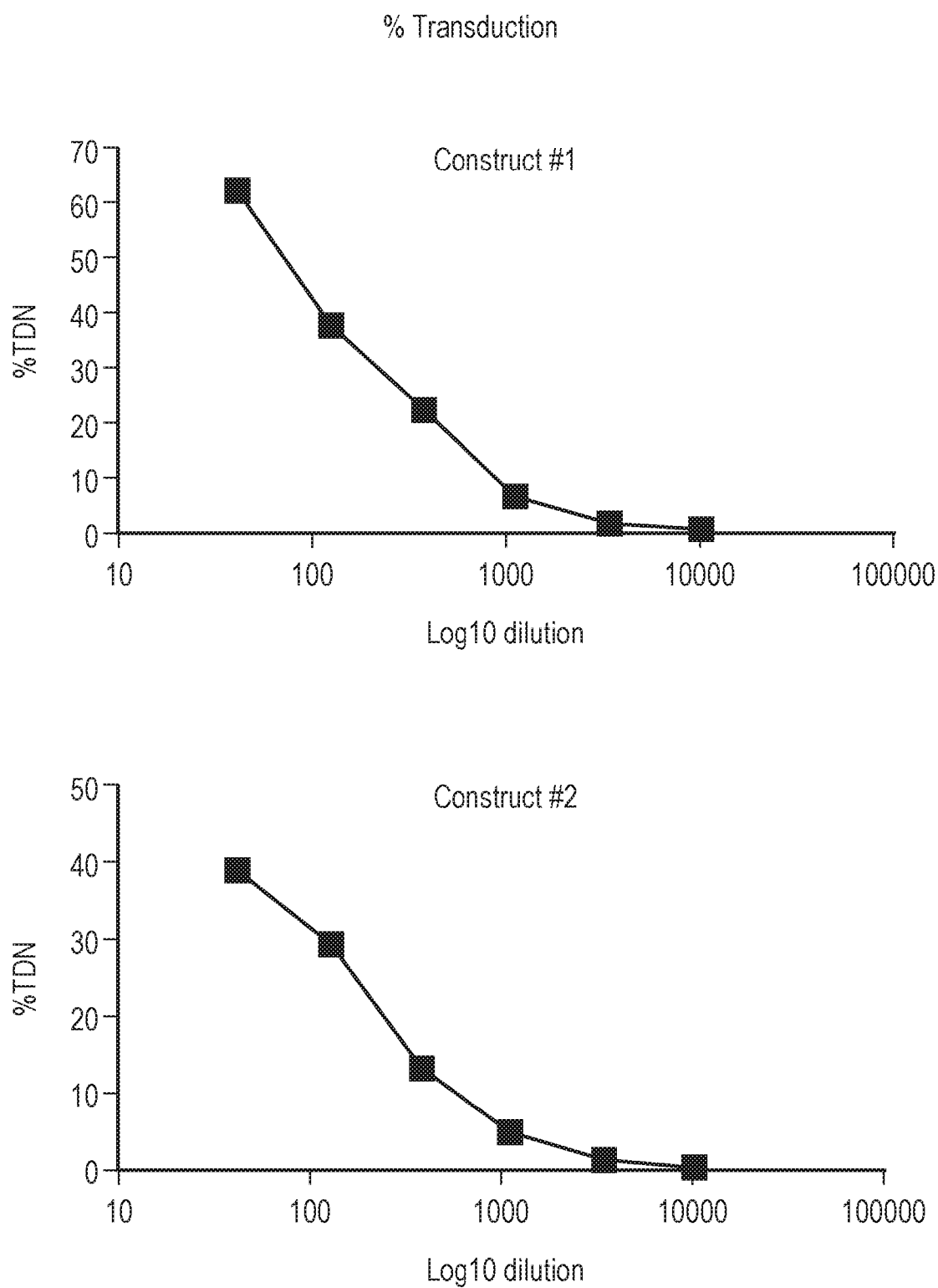
Figure 2:
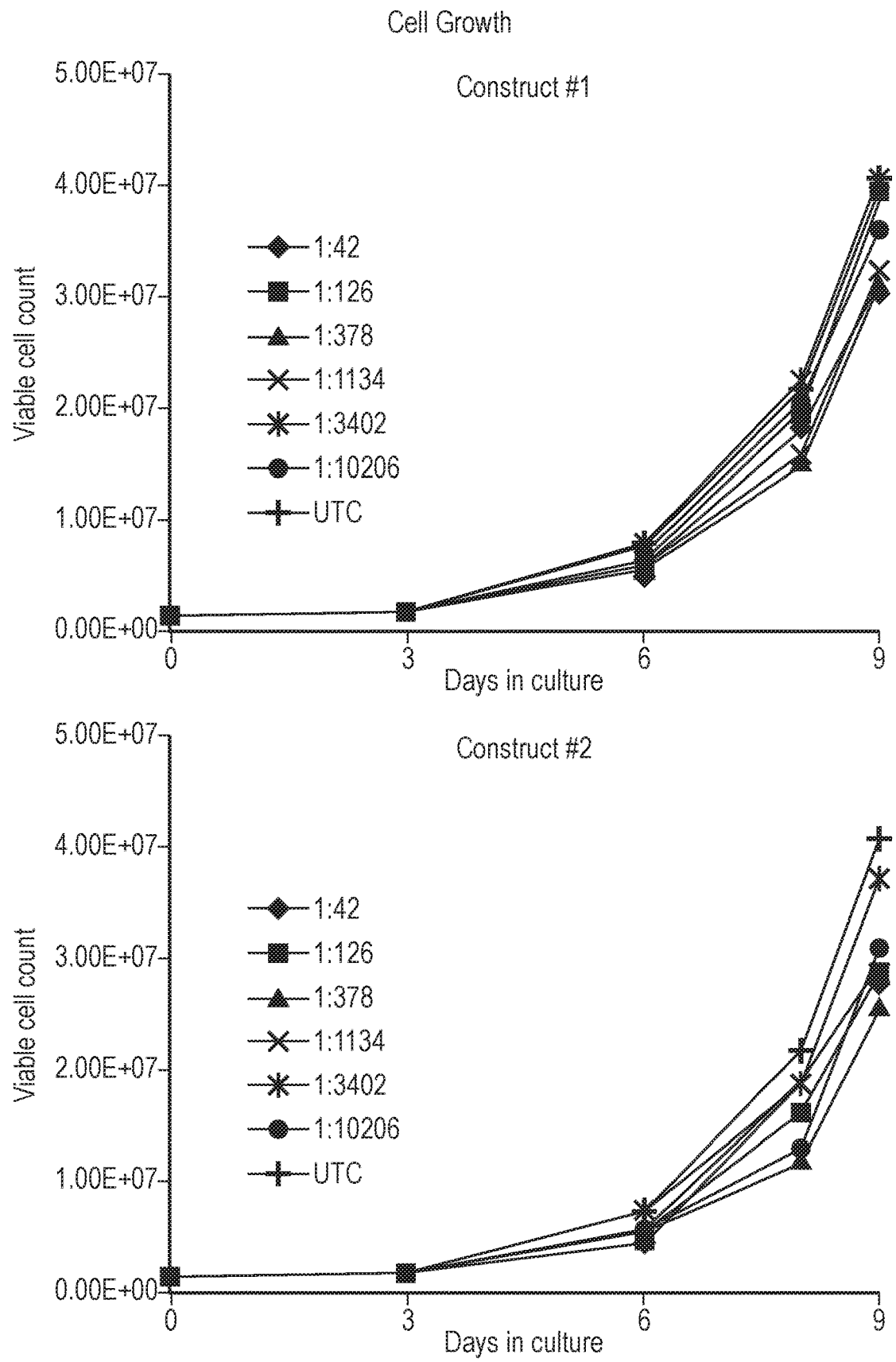

FIG. 2: Transduction of CAR-5T4 constructs into and subsequent growth in human T cells.

Figure 3:
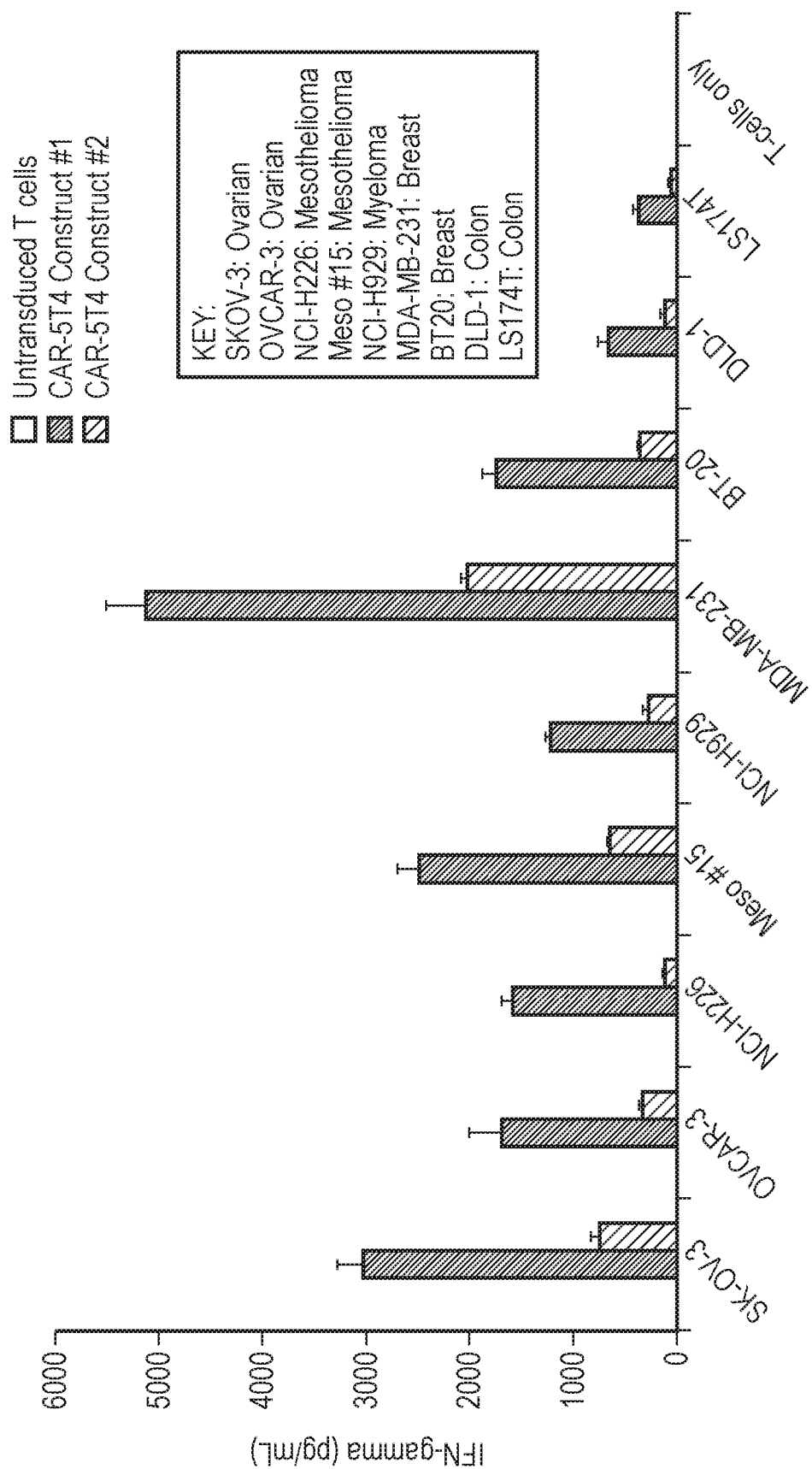

FIG. 3: In vitro IFNγ secretion by 5T4 CAR-T cells following exposure to 5T4-positive tumour cells.

Figure 4:
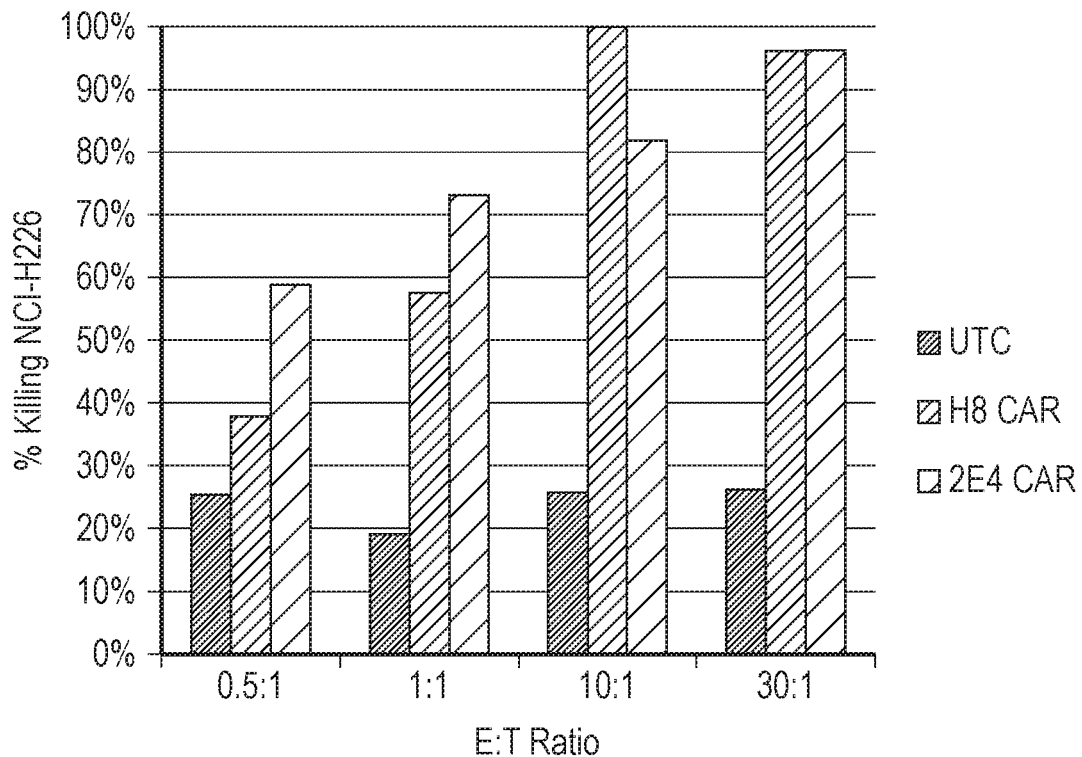
Figure 4:
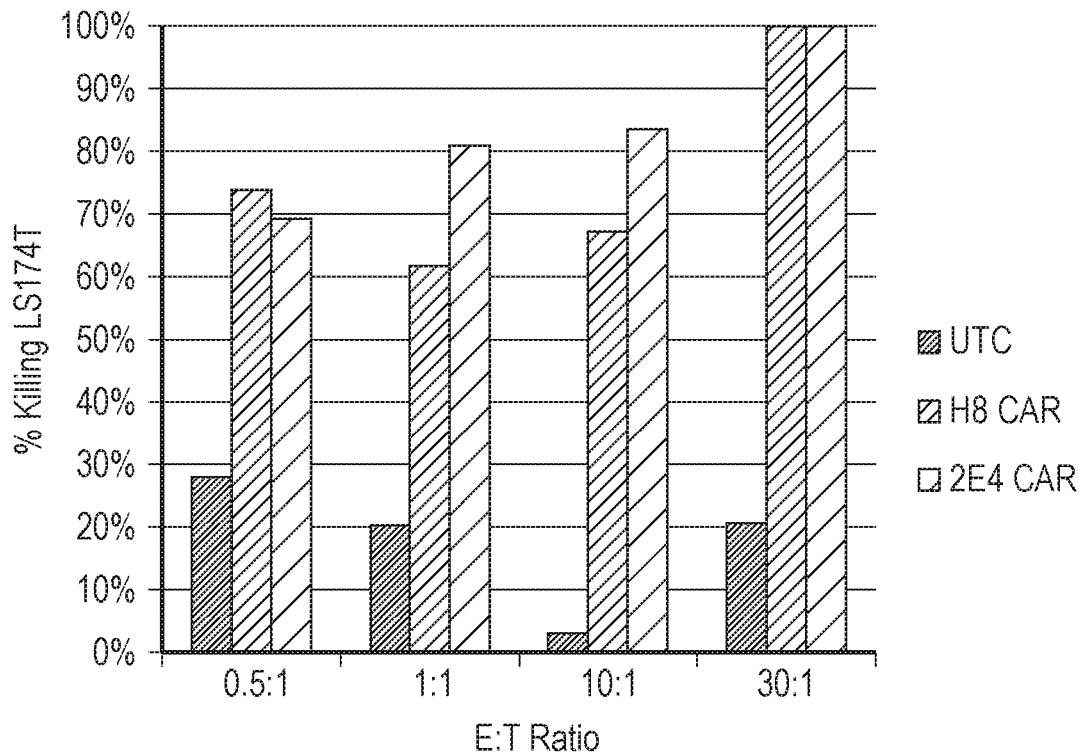

FIG. 4: Activity of 5T4 CAR constructs H8-EF1α-CD3ζ/4-1BB and 2E4-EF1α-CD3ζ/4-1BB in vitro against (A) the human mesothelioma cell line NCI-H226 (high 5T4 expresser) and (B) the colorectal cell line LS174T (low 5T4 expresser).

Figure 5:
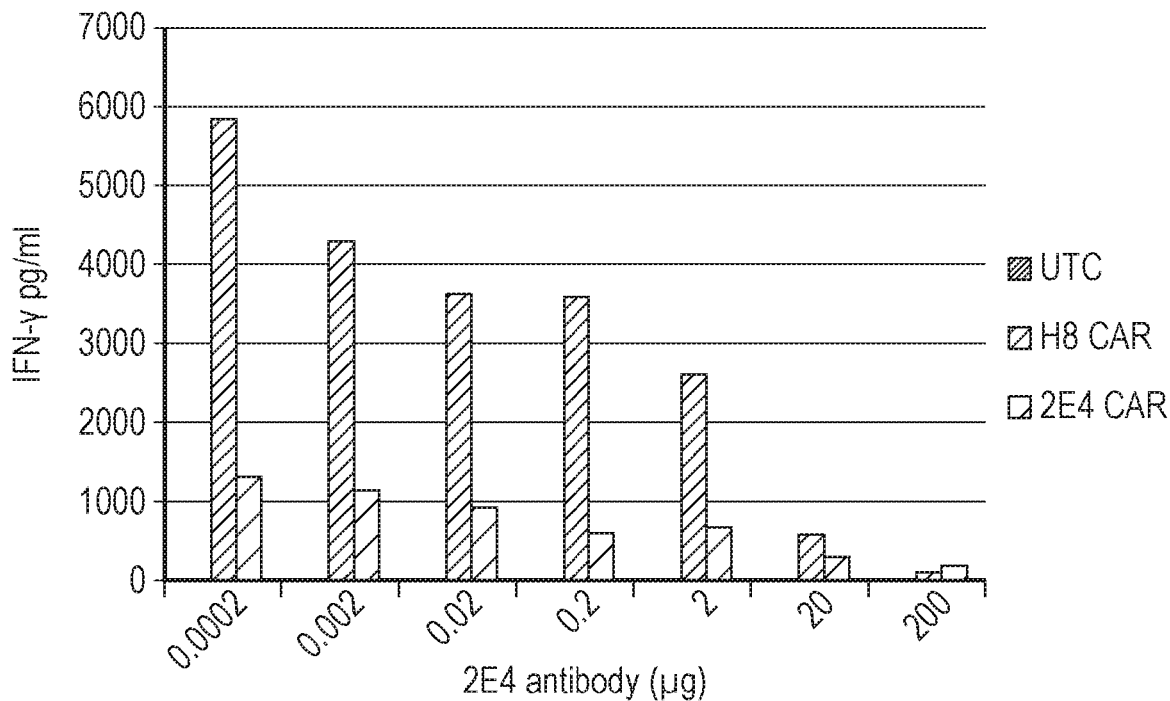
Figure 5:
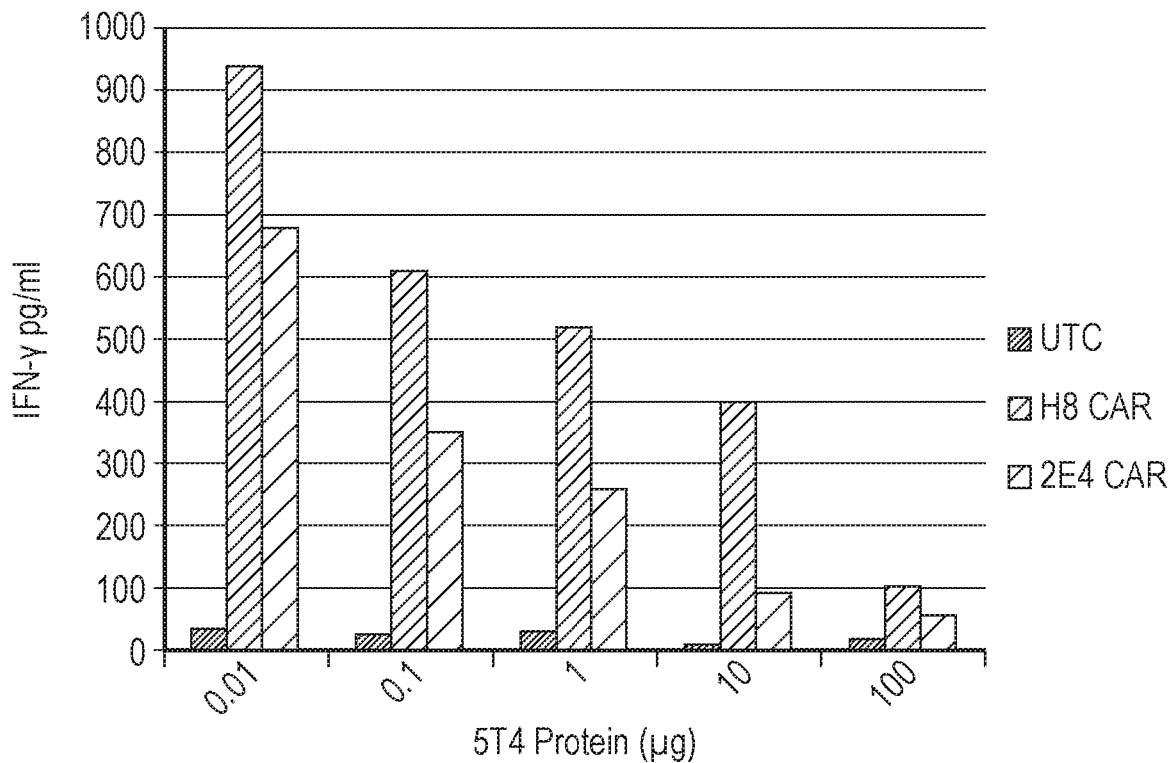

FIG. 5: Specificity of 5T4 CAR constructs (H8-EF1α-CD3ζ/4-1BB and 2E4-EF1α-CD3ζ/4-1BB) for 5T4-blocking in vitro using a 5T4-specific monoclonal antibody/5T4 protein.

Figure 6:
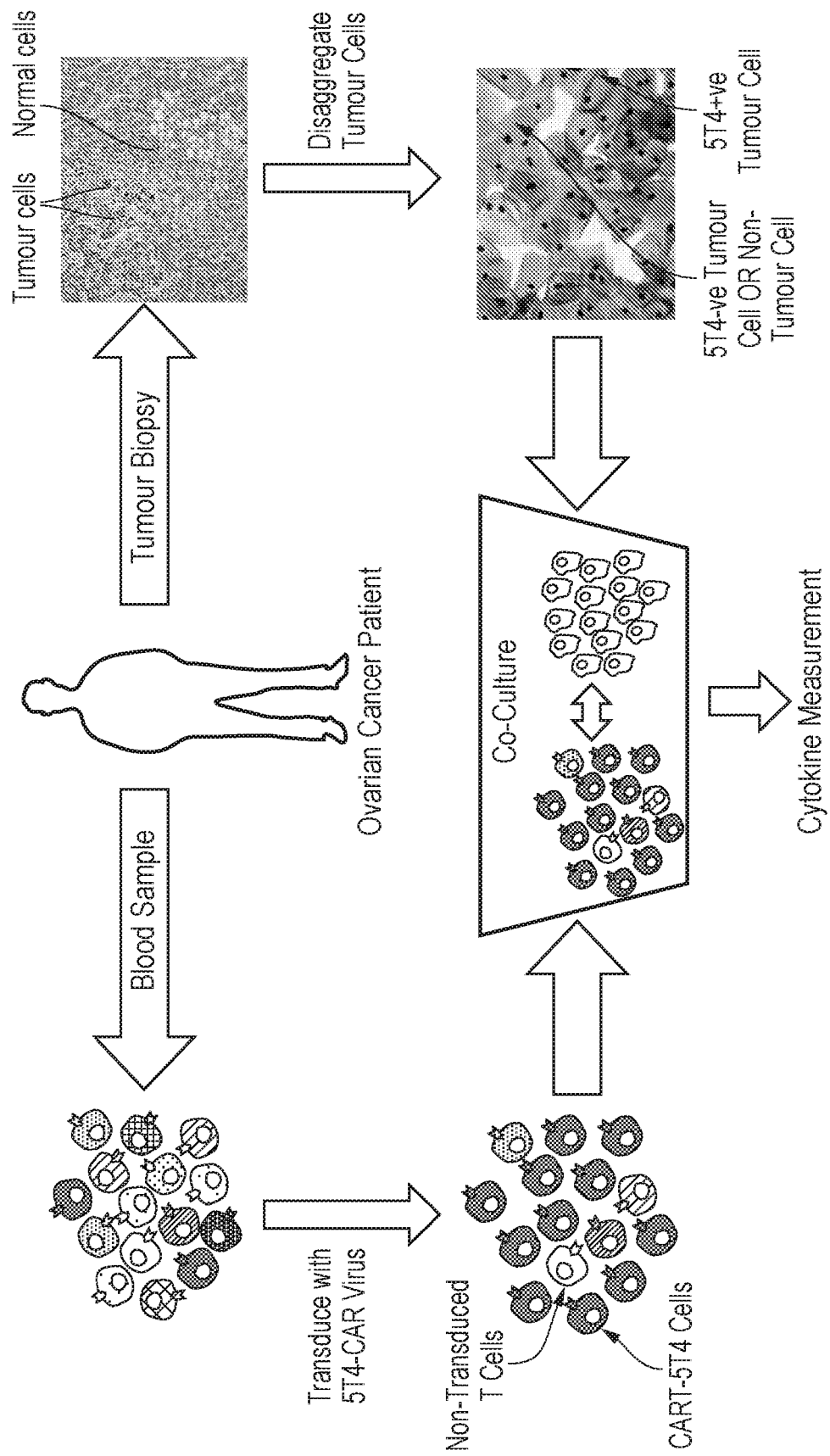

FIG. 6: Schematic for the in vitro assessment of CAR-T cell functionality, when co-cultured with ovarian cancer cells.

Figure 7:
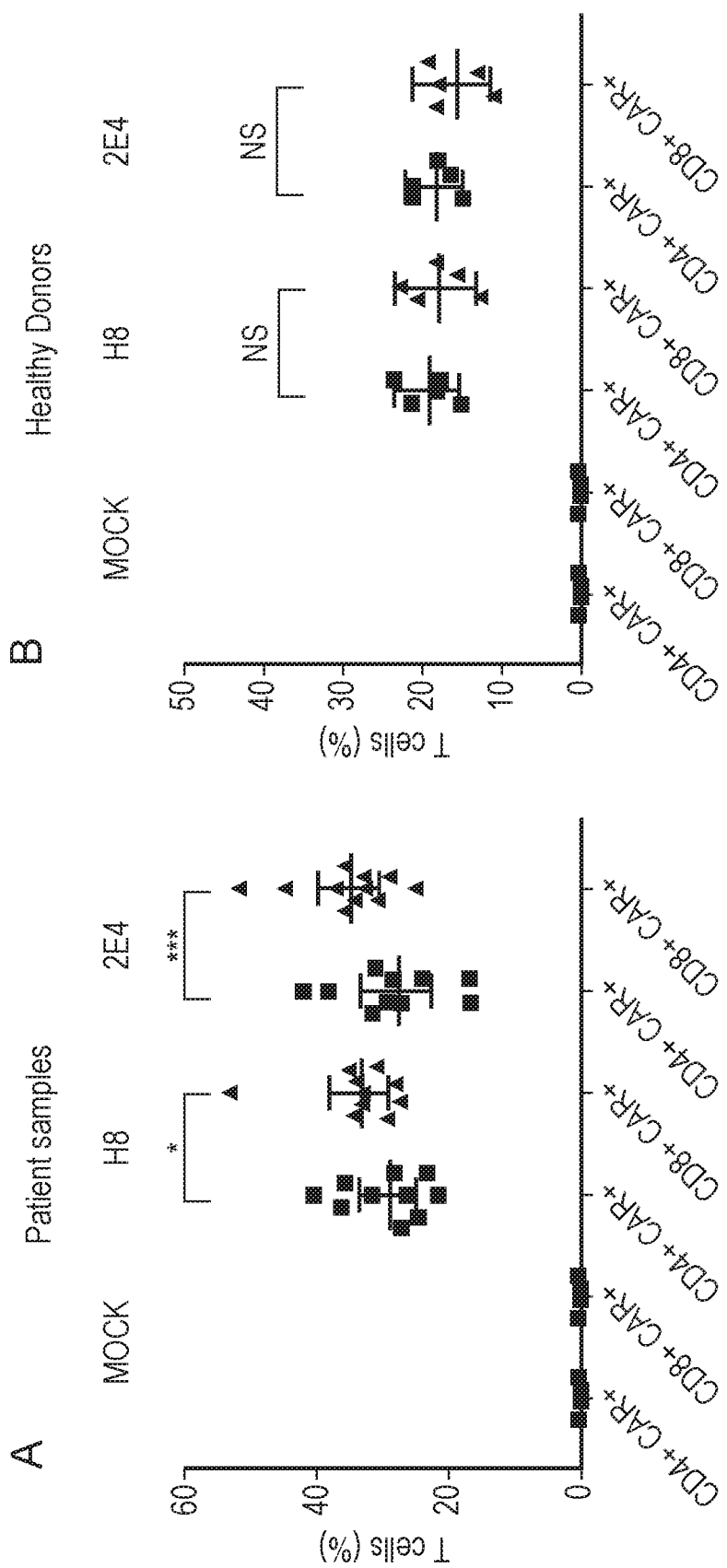

FIG. 7: Transduction of 5T4 CAR construct into PBMCs from (A) ovarian cancer patients compared to (B) healthy donors.

Figure 8:
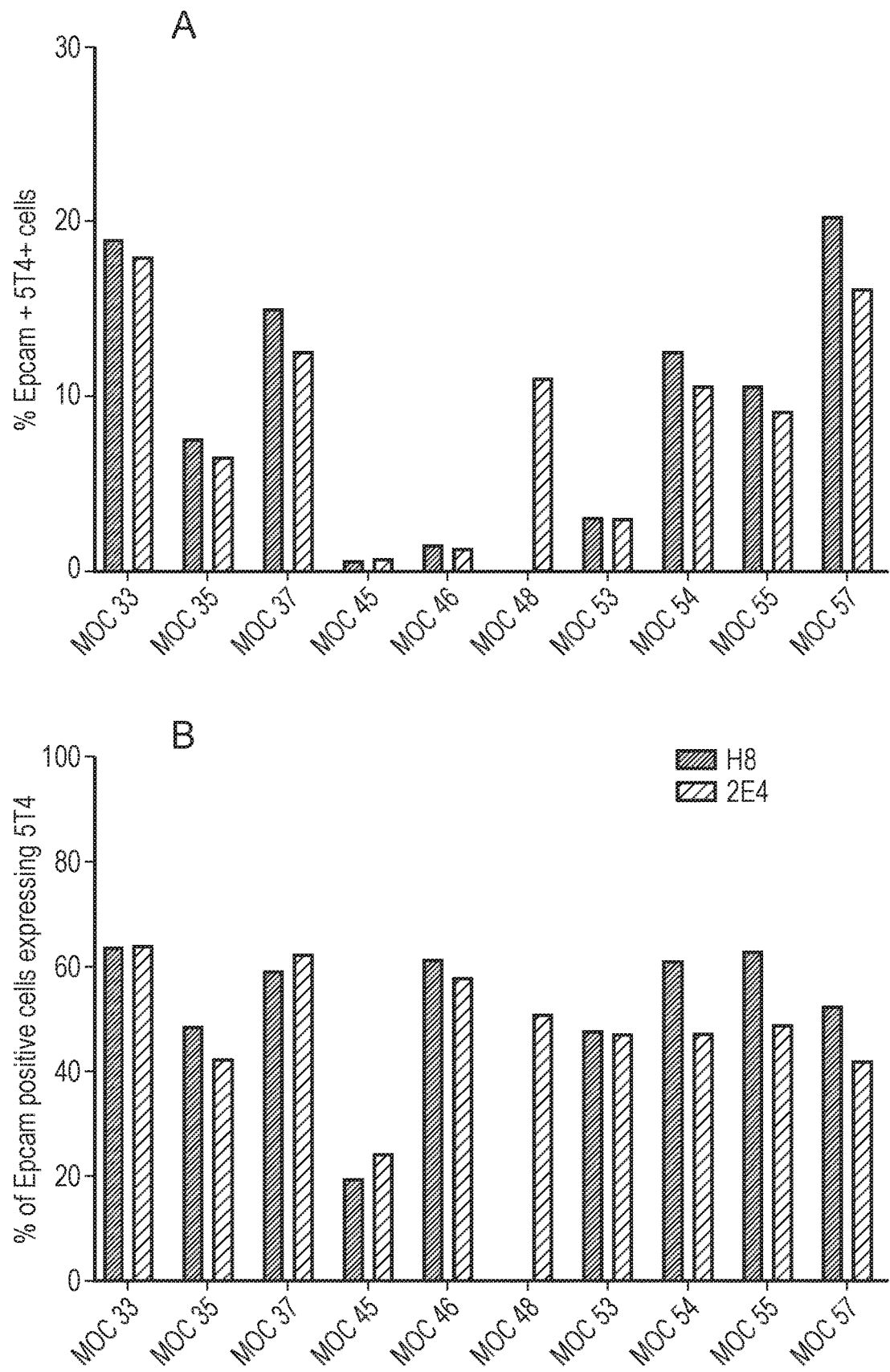

FIG. 8: 5T4 Expression on tumour disaggregates recovered from ovarian cancer patients and stained with either (A) H8 or (B) 2E4 5t4-specific monoclonal antibodies.

Figure 9:
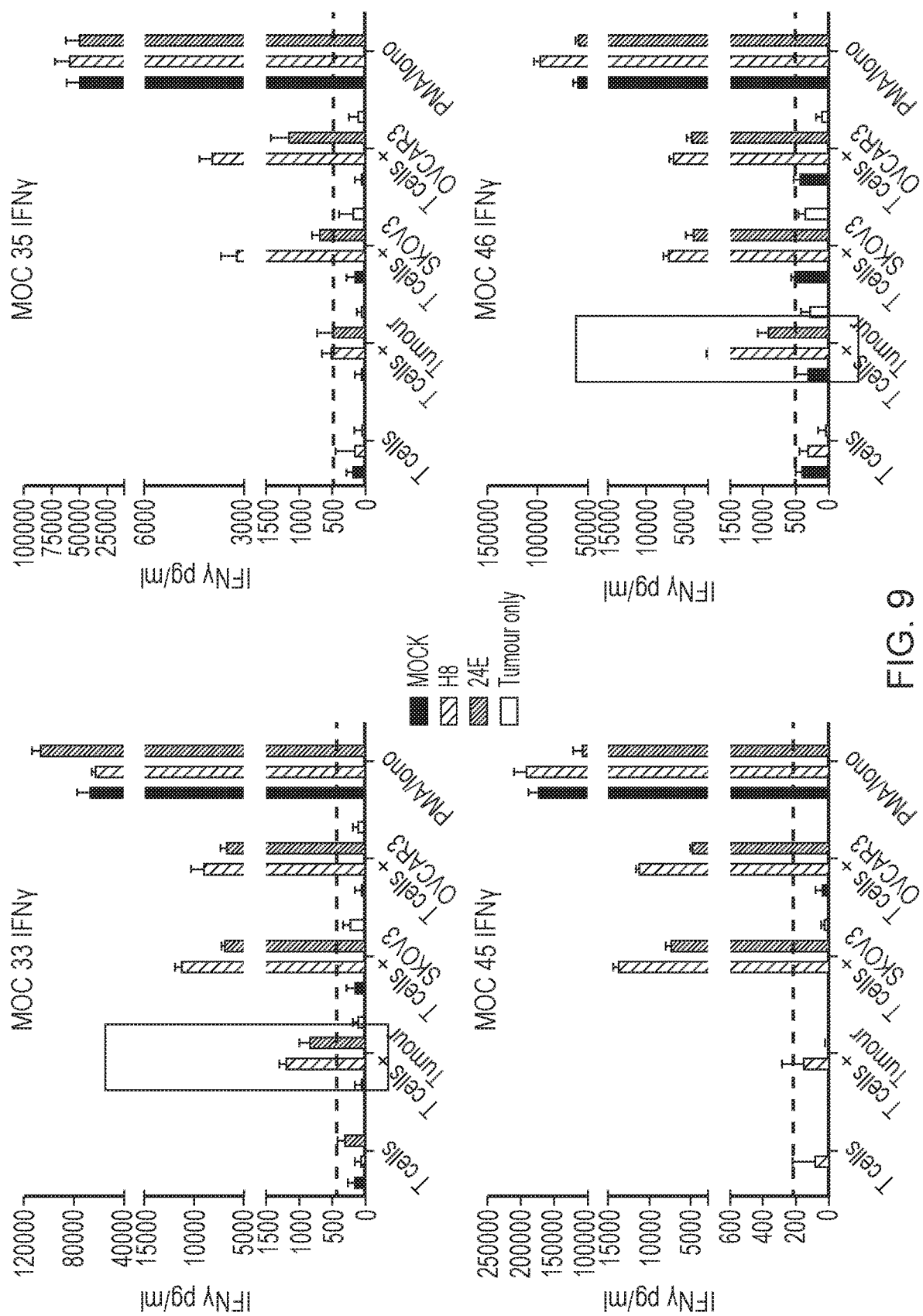
Figure 9:
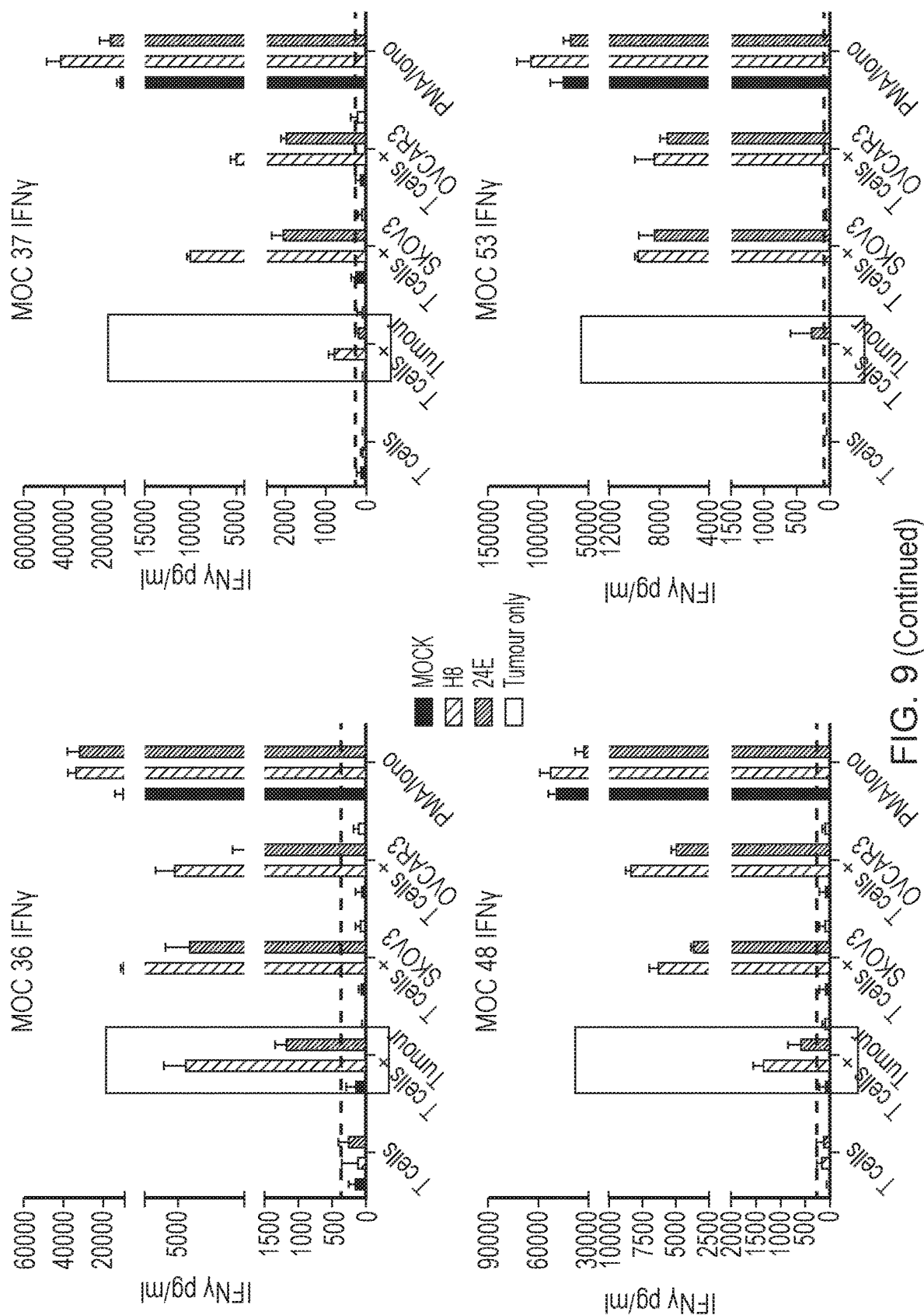

FIG. 9: IFNγ secretion by CAR-T 5T4 cells co-cultured with autologous ovarian tumour disaggregates.

Figure 10:
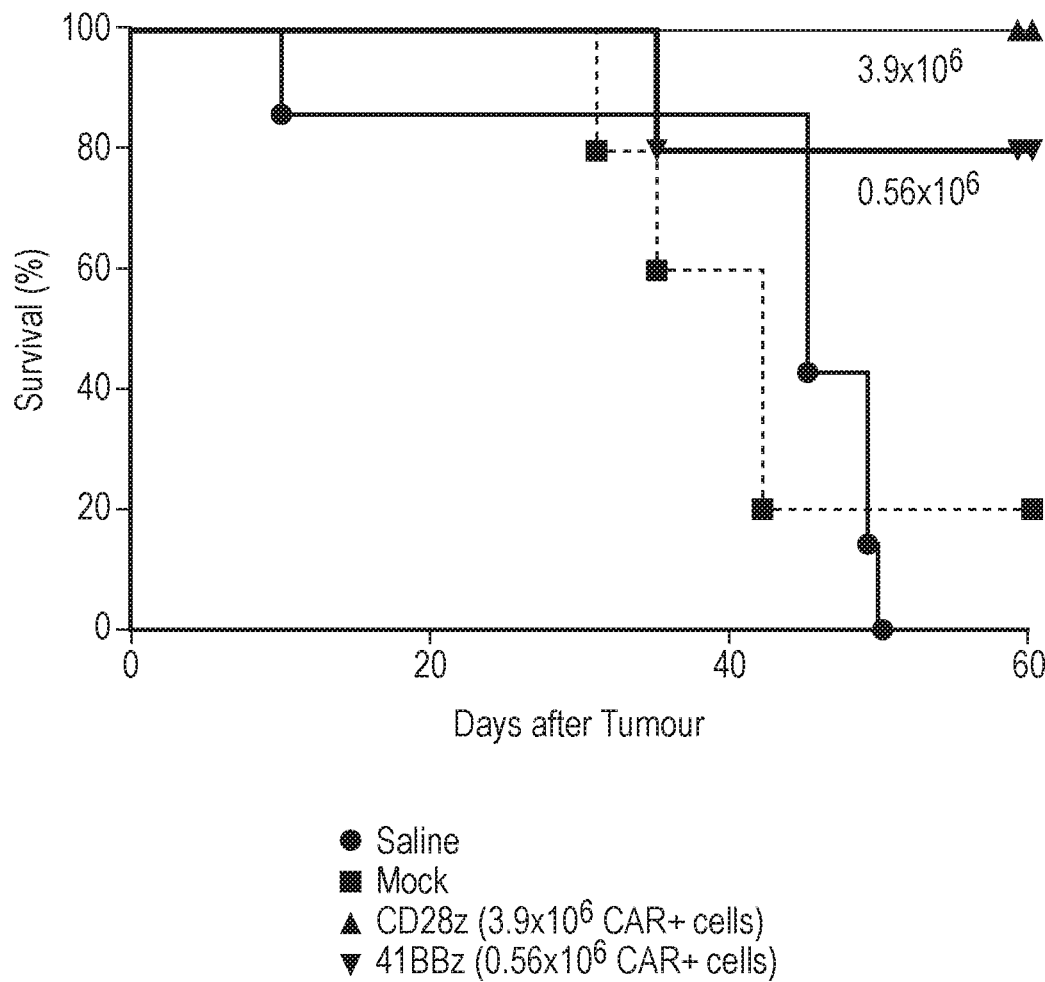

FIG. 10: Survival curve showing in vivo efficacy of 5T4 CAR-T cells against an ovarian cancer model; Construct: CMV-H8-CAR-CD3ζ/4-1BB and CMV-H8-CAR-CD3ζ/CD28; Mice: NSG (3 per group); Cell Dose/Route: $2 \times 10^7$ Total T cells, IV Administration.

Figure 11:
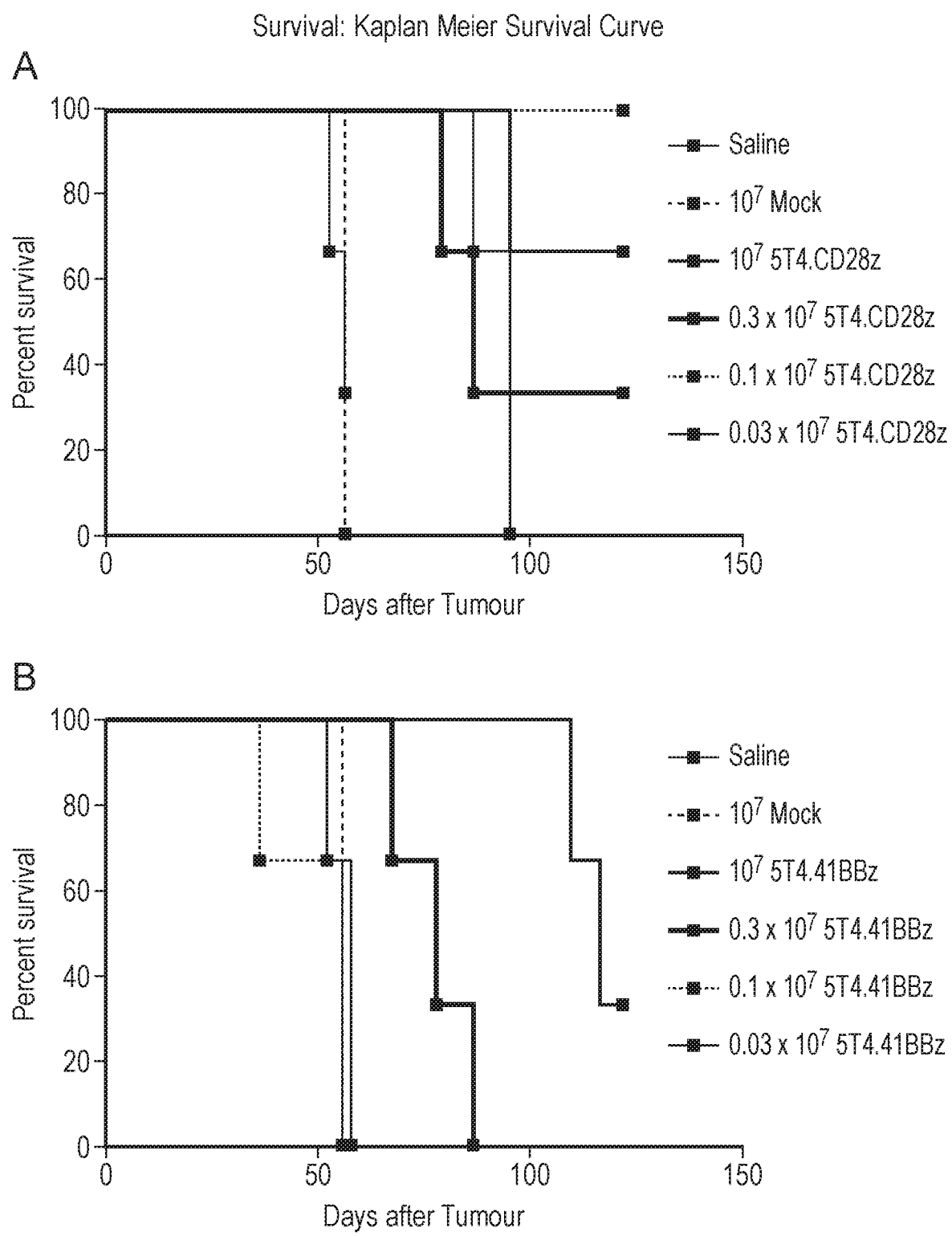

FIG. 11: Survival curves showing minimal efficacious dose of 5T4 CAR-T cells against an ovarian cancer model; Construct: CMV-H8-CAR-CD3ζ/4-1BB (Panel B) and CMV-H8-CAR-CD3ζ/CD28 (Panel A); Tumour Cell: SKOV-3Ovarian Cancer ($2.5 \times 10^6$ IP administered challenge) CAR-T Cells: $1 \times 10^7$, $0.3 \times 10^7$, $0.1 \times 10^7$, $0.03 \times 10^7$ CAR-T cells delivered via IV administration.

Figure 12:
Figure 12:
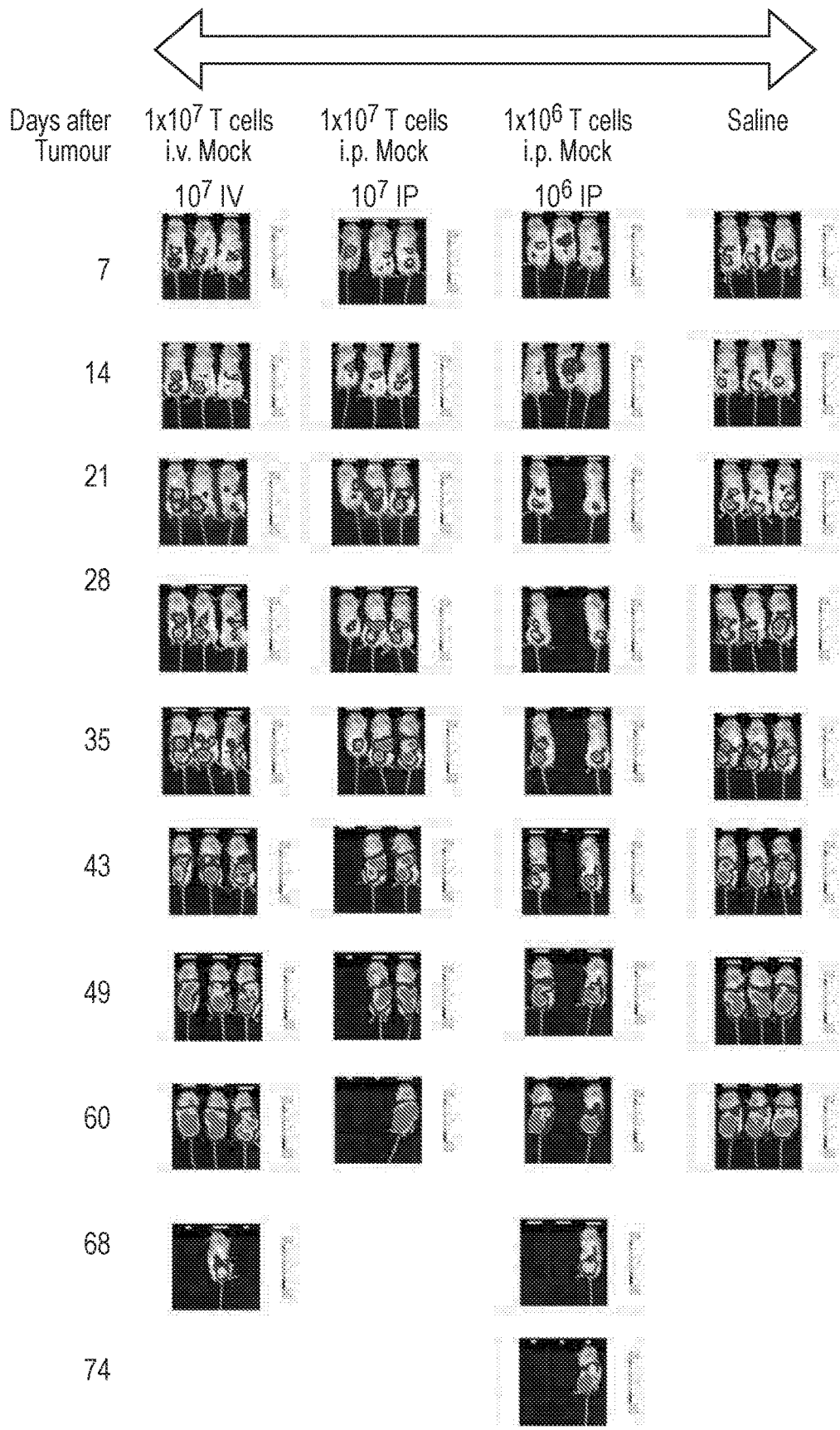

FIG. 12: Bioluminescence images showing comparison between efficacy of CAR-T administration through either IP or IV administration against ovarian cancer challenge; Tumour Cell: SKOV-3 Ovarian Cancer ($2.5 \times 10^6$ IP administered challenge); CAR-T Cells: $1 \times 10^7$ or $1 \times 10^6$ CAR T cells via IP or IV administration route.

Figure 13:
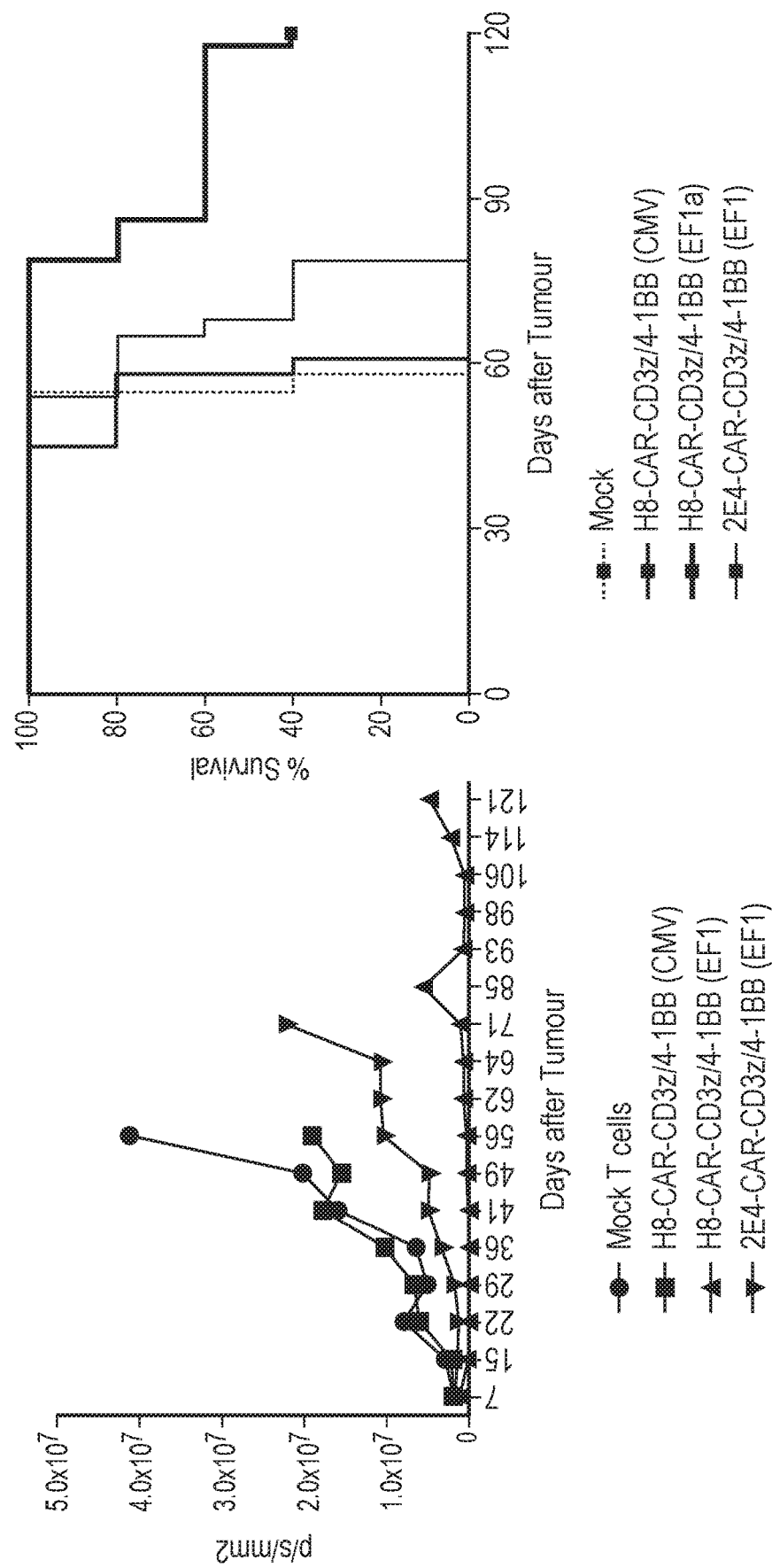

FIG. 13: Survival curve showing in vivo efficacy of 5T4 CAR-T cells against an ovarian cancer model using different α-5T4 ScFv; Constructs: (H8-EF1α-CD3ζ/4-1BB and 2E4-EF1α-CD3ζ/4-1BB); Test Cells: $1 \times 10^7$ CART cells; Tumour Cell: SKOV-3 Ovarian Cancer.

Figure 14:
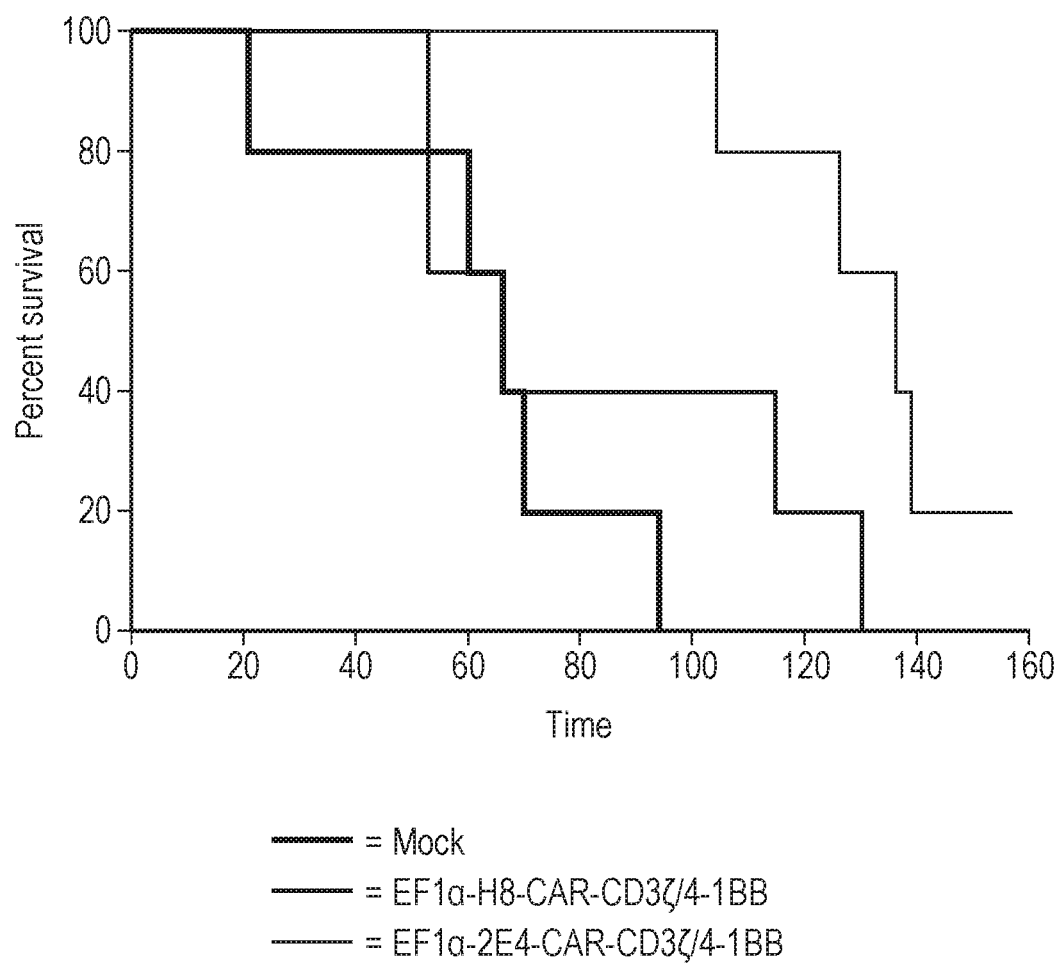

FIG. 14: Survival curve showing in vivo efficacy of 5T4 CAR-T cells against an ovarian cancer model using different α-5T4 ScFv; Constructs: (H8-EF1α-CD3ζ/4-1BB and 2E4-EF1α-CD3ζ/4-1BB); Tumour Cell: NCI-H929 Myeloma Cells.

Figure 15:
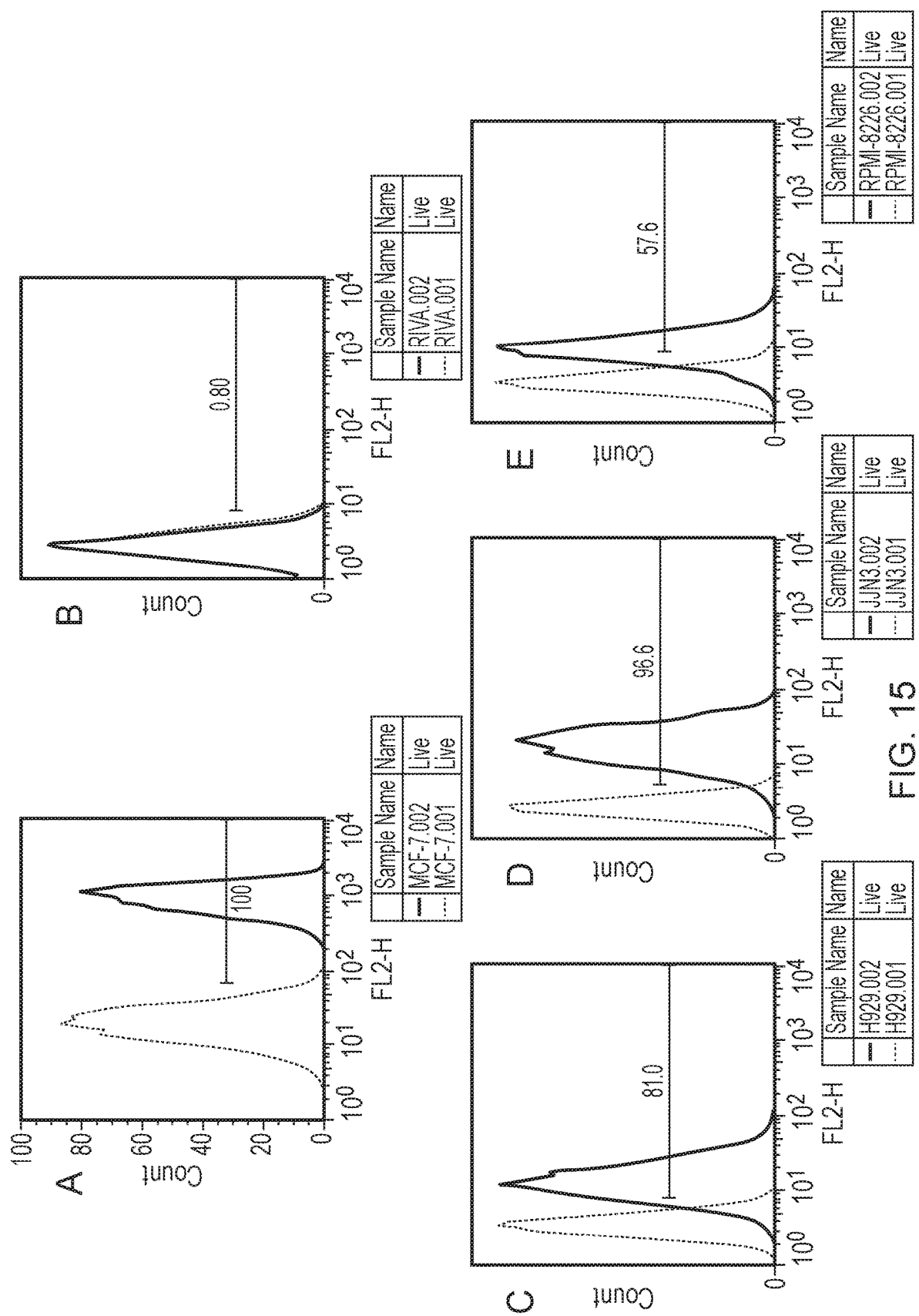

FIG. 15: FACS analysis of 5T4 expression in three myeloma cell lines; A: Positive Control (Breast [MCF7] cell line); B: Negative Control (DLBCL); C: H929 Myeloma line; D: JJN3 Myeloma cell line; E: RPMI-8226 cell line.

Figure 16:
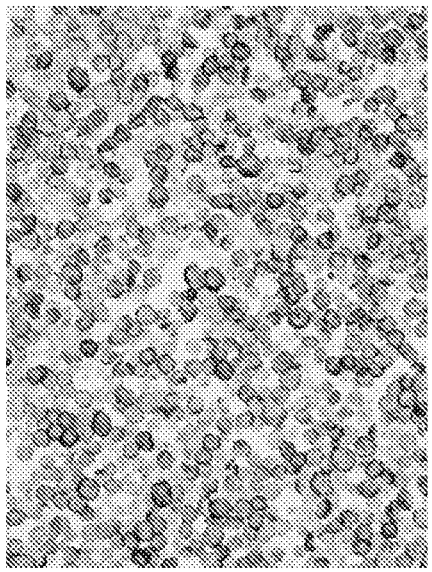
Figure 16:
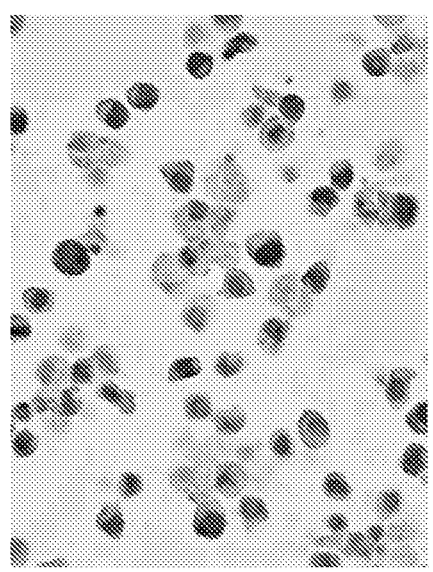
Figure 16:
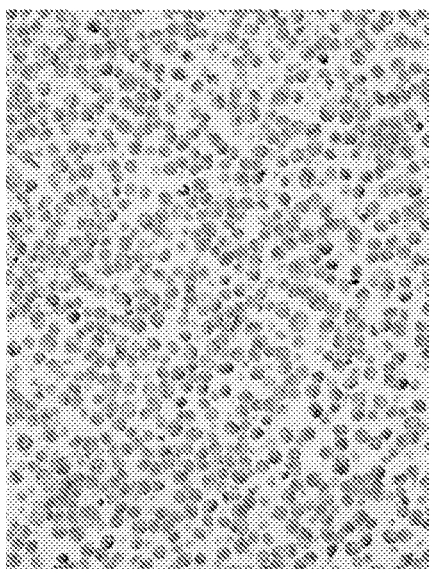
Figure 16:
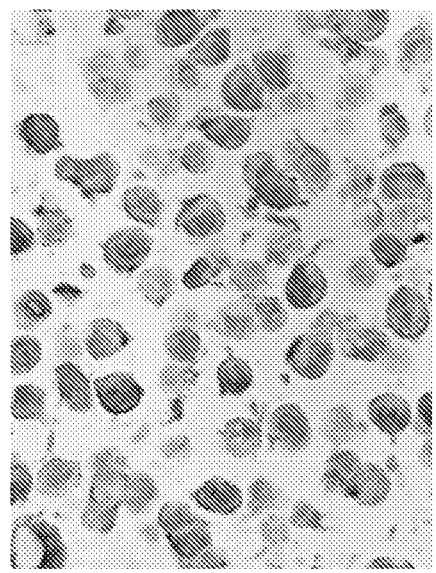
Figure 17:
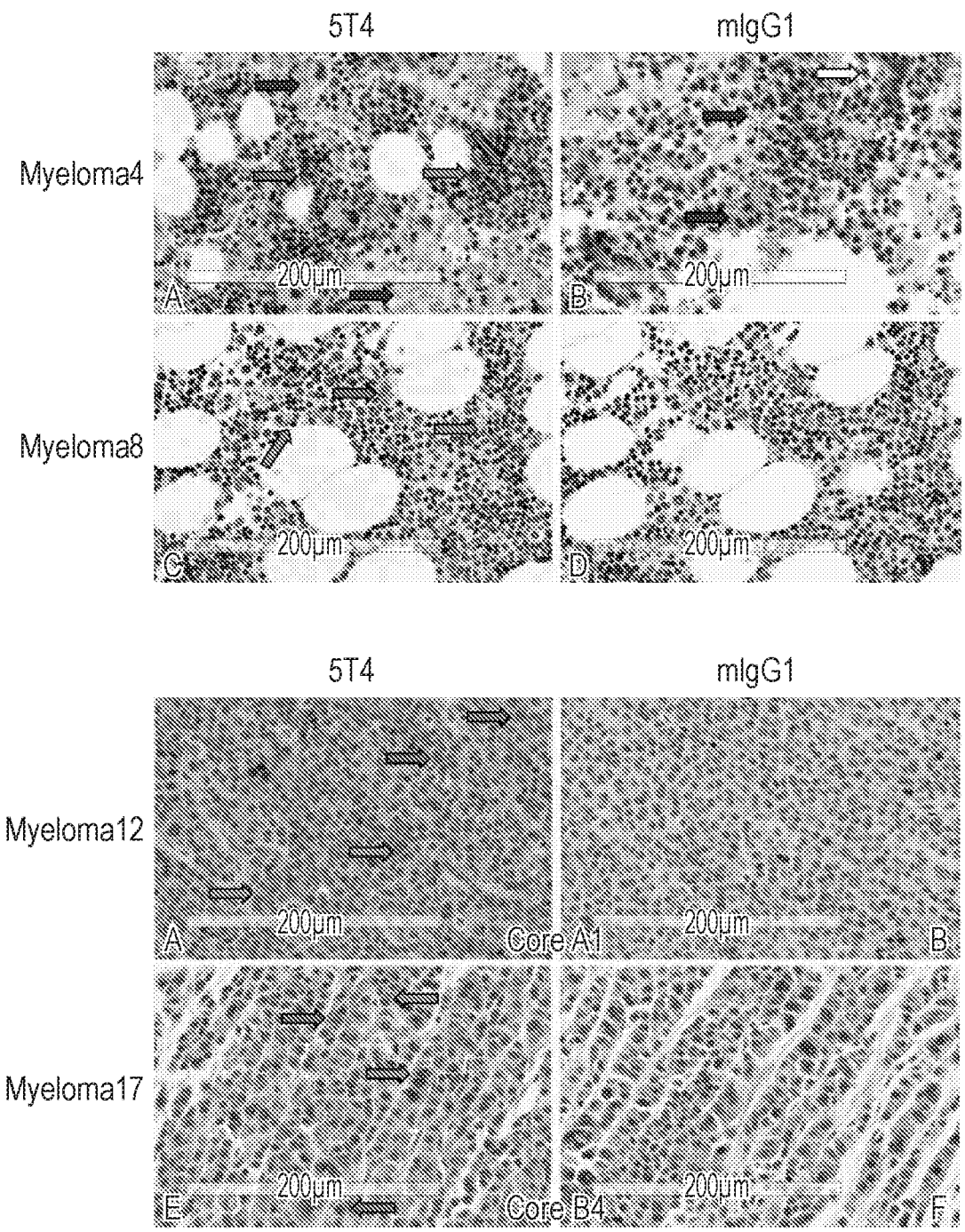

FIG. 16: Immunohistochemistry images, staining for 5T4; A: CHO cells (negative control); B: CHO cells transfected with 5T4 (positive control); C: MCF7 (Breast) cells; D: H929 (myeloma) cells FIG. 17: Immunohistochemistry images, staining for 5T4 on myeloma samples taken from 4 patients with multiple myeloma.

Figure 18:
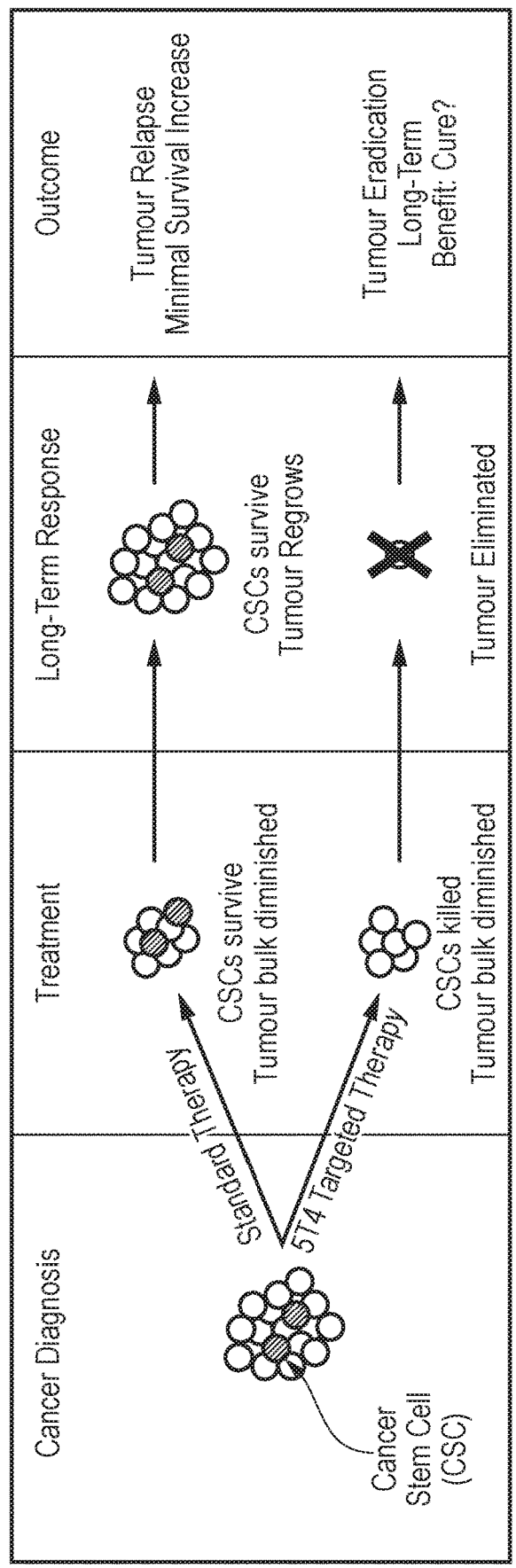

FIG. 18: Importance of Eradication of Cancer Stem Cells in the Treatment of Cancer. It has been postulated that conventional chemotherapy (standard therapy) de-bulks most solid tumours by removing the rapidly proliferating cells but misses the cancer stem cells (CSCs) that are likely to be more resistant to the therapy due to their membrane-sited drug transporters, which could lead to relapse. It can be argued that the optimal therapeutic regimen for removing a tumour, aside from surgery, is to target both the bulk tumour cells and the cancer stem cells within the tumour (e.g. 5T4 targeted therapy).

Figure 19:
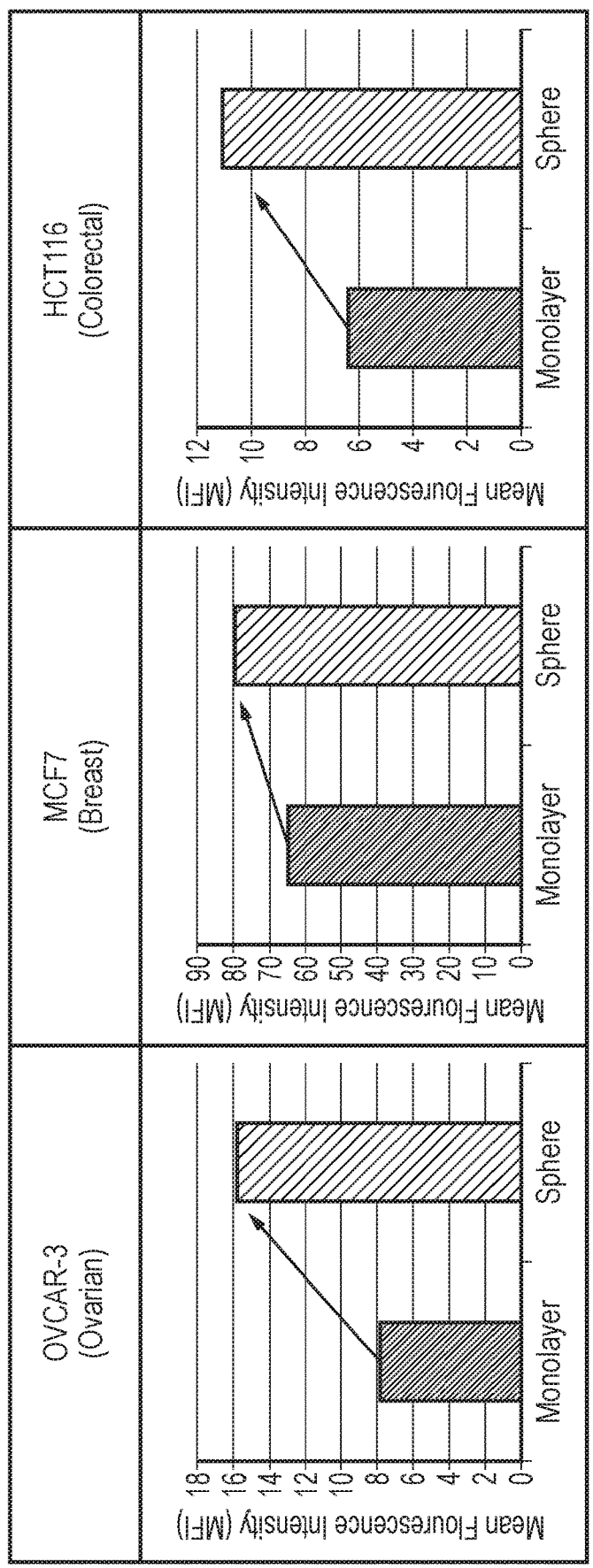
Figure 19:
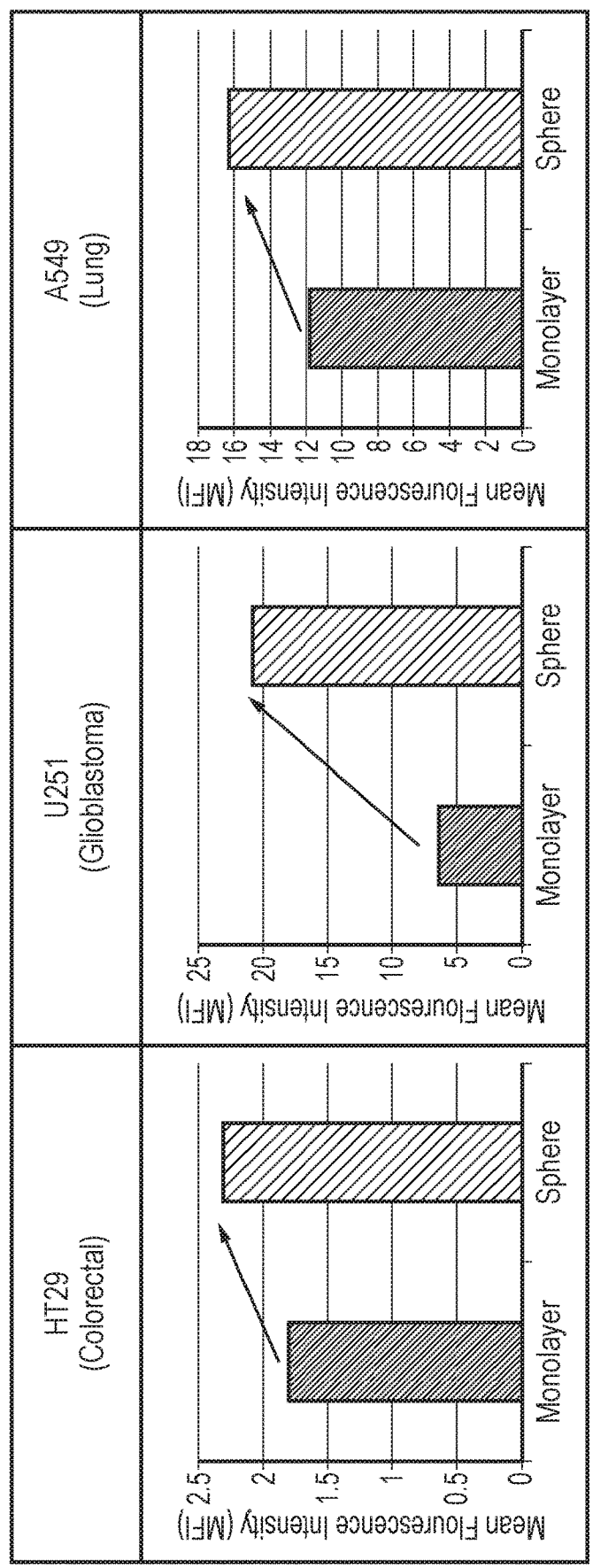

FIG. 19: 5T4 Expression on Cancer Stem Cells in Solid Tumours. The figure shows the level of 5T4 expression on "bulk" tumour cells (monolayer) or cancer stem cells (Sphere) in OVCAR-3 (Ovarian), MCF7 (Breast), HCT116 (Colorectal), HT29 (Colorectal), U251 (Glioblastoma) and A549 (Lung) cell lines.

HAEMATOLOGICAL CANCERS

There are numerous different types of haematological cancers, The present invention extends to haematological cancers which are not pre-B acute lymphoblastic leukaemia.

The main types of haematological cancer can be classed as leukaemia, lymphoma or myeloma.

The leukaemias are a group of cancers that usually begin in the bone marrow and result in high numbers of abnormal white blood cells. These white blood cells are not fully developed and are called blasts or leukaemia cells.

Clinically and pathologically, leukaemia is subdivided into a number of groups. The first division is between its acute and chronic forms:

Acute leukaemia is characterized by a rapid increase in the number of immature blood cells. The crowding that results from such cells makes the bone marrow unable to produce healthy blood cells. Immediate treatment is required in acute leukaemia because of the rapid progression and accumulation of the malignant cells, which then spill over into the bloodstream and spread to other organs of the body. Acute forms of leukaemia are the most common forms of leukaemia in children.

Chronic leukaemia is characterized by the excessive buildup of relatively mature, but still abnormal, white blood cells. Typically taking months or years to progress, the cells are produced at a much higher rate than normal, resulting in many abnormal white blood cells.

Whereas acute leukaemia must be treated immediately, chronic forms are sometimes monitored for some time before treatment to ensure maximum effectiveness of therapy. Chronic leukaemia mostly occurs in older people, but can occur in any age group.

Additionally, the diseases are subdivided according to which kind of blood cell is affected. This divides leukaemias into lymphoblastic or lymphocytic leukaemias and myeloid or myelogenous leukaemias. Most lymphocytic leukaemias involve B cells. In myeloid or myelogenous leukaemias, the cancerous change takes place in a type of marrow cell that normally goes on to form red blood cells, some other types of white cells, and platelets.

Thus, there are four main types of leukaemia: acute myeloid (AML), acute lymphoblastic (ALL), chronic myeloid (CML) and chronic lymphocytic (CLL). These 4 main types account for around 85% of all leukaemia cases.

Treatment may involve some combination of chemotherapy, radiation therapy, targeted therapy, and bone marrow transplant, in addition to supportive care and palliative care as needed.

Leukaemia can be classified and/or stratified according to various conventions, for example but not limited to those as discussed below. The present invention extends to all stages and classes.

AML

The French-American-British (FAB) classification of AML is based on the following:

| FAB subtype | Name |
| --- | --- |
| M0 | Undifferentiated acute myeloblastic leukemia |
| M1 | Acute myeloblastic leukemia with minimal maturation |
| M2 | Acute myeloblastic leukemia with maturation |
| M3 | Acute promyelocytic leukemia (APL) |
| M4 | Acute myelomonocytic leukemia |
| M4 eos | Acute myelomonocytic leukemia with eosinophilia |
| M5 | Acute monocytic leukemia |
| M6 | Acute erythroid leukemia |
| M7 | Acute megakaryoblastic leukemia |

CML

CML is classified into 3 groups that help predict outlook. These groups are referred to as phases instead of stages. The phases are based mainly on the number of immature white blood cells—myeloblasts (blasts)—that are seen in the blood or bone marrow. Different groups of experts have suggested slightly different cutoffs to define the phases, but a common system (proposed by the World Health Organization) is described below.

Chronic Phase

Patients in this phase typically have less than 10% blasts in their blood or bone marrow samples. These patients usually have fairly mild symptoms (if any) and usually respond to standard treatments. Most patients are diagnosed in the chronic phase.

Accelerated Phase

Patients are considered to be in accelerated phase if any of the following are true:

The bone marrow or blood samples have more than 10% but fewer than 20% blasts

High blood basophil count (basophils making up at least 20% of the white blood cells)

High white blood cell counts that do not go down with treatment

Very high or very low platelet counts that are not caused by treatment

New chromosome changes in the leukemia cells

Patients whose CML is in accelerated phase may have symptoms such as fever, poor appetite, and weight loss. CML in the accelerated phase does not respond as well to treatment as CML in the chronic phase.

Blast Phase (Also Called Acute Phase or Blast Crisis)

Bone marrow and/or blood samples from a patient in this phase have more than 20% blasts. The blast cells often spread to tissues and organs beyond the bone marrow. These patients often have fever, poor appetite, and weight loss. In this phase, the CML acts much like an aggressive acute leukemia.

ALL

Classification may be based on immunophenotype. Cytogenetic tests, flow cytometry, and other lab tests provide more detailed information about the subtype of ALL and the patient's prognosis. These tests help divide ALL into groups based on the immunophenotype of the leukemia, which takes into account:

The type of lymphocyte (B cell or T cell) the leukemia cells come from

How mature these leukemia cells are

The subtypes of ALL are now named as follows:

B-Cell ALL

Early pre-B ALL (also called pro-B ALL)—about 10% of cases

Common ALL—about 50% of cases

Pre-B ALL—about 10% of cases

Mature B-cell ALL (Burkitt leukemia)—about 4% of cases

T-Cell ALL

Pre-T ALL—about 5% to 10% of cases

Mature T-cell ALL—about 15% to 20% of cases

The subtypes of ALL each carry a slightly different outlook (prognosis), but other factors (like gene changes in the leukemia cells) may also have an impact.

Mixed Lineage Acute Leukemias

In recent years, newer lab tests have shown that a small number of acute leukemias actually have both lymphocytic and myeloid features. Sometimes the leukemia cells have both myeloid and lymphocytic traits in the same cells. In other cases, a person may have some leukemia cells with myeloid features and others with lymphocytic features. These types of leukemias may be called mixed lineage leukemia, ALL with myeloid markers (My+ ALL), AML with lymphoid markers, or biphenotypic acute leukemia (BAL).

Most studies suggest these leukemias tend to have a poorer outlook than standard subtypes of ALL or AML.

CLL

There are 2 different systems for staging CLL:

Rai system: This is used more often in the United States.

Binet system: This is used more widely in Europe.

Rai Staging System

The Rai system was originally devised in 1968. At that time, all that was needed to diagnose CLL was lymphocytosis—a high number of lymphocytes in the blood and bone marrow that didn't have any other cause (like infection). This was originally defined as over 15,000 lymphocytes/$mm^3$ of blood and at least 40% of the bone marrow being made up of lymphocytes.

Now, for a diagnosis of CLL, the patient must have at least 5,000/$mm^3$ of monoclonal lymphocytes (sometimes called a monoclonal lymphocytosis), but the overall lymphocyte count does not have to be high. Monoclonal means that the cells all came from the same cell, which can lead to them having the same chemical pattern on special testing.

For the purposes of this staging, you can substitute a diagnosis of CLL (such as with a monoclonal lymphocytosis) for lymphocytosis.

This system divides CLL into 5 stages:

Rai stage 0: Lymphocytosis and no enlargement of the lymph nodes, spleen, or liver, and with near normal red blood cell and platelet counts.

Rai stage I: Lymphocytosis plus enlarged lymph nodes. The spleen and liver are not enlarged and the red blood cell and platelet counts are near normal.

Rai stage II: Lymphocytosis plus an enlarged spleen (and possibly an enlarged liver), with or without enlarged lymph nodes. The red blood cell and platelet counts are near normal.

Rai stage III: Lymphocytosis plus anemia (too few red blood cells), with or without enlarged lymph nodes, spleen, or liver. Platelet counts are near normal.

Rai stage IV: Lymphocytosis plus thrombocytopenia (too few blood platelets), with or without anemia, enlarged lymph nodes, spleen, or liver.

In one aspect of the invention the haematological cancer is leukaemia. The leukaemia may be selected from chronic myeloid leukaemia, chronic lymphocytic leukaemia, acute myeloid leukaemia, B-cell acute lymphoblastic leukaemia (B-ALL), and T-cell acute lymphoblastic leukaemia (T-ALL).

In one aspect of the invention the haematological cancer is not ALL. In one aspect the haematological cancer is not B-ALL.

The haematological cancer according to the invention may be a lymphoma. Lymphoma is a group of cancers that develop from lymphocytes. The two main categories of lymphomas are Hodgkin's lymphomas (HL) and the non-Hodgkin lymphomas (NHL). Hodgkin lymphoma accounts for about 15% of lymphomas. It differs from other forms of lymphoma in its prognosis and several pathological characteristics. A Hodgkin lymphoma is marked by the presence of a type of cell called the Reed-Sternberg cell. Non-Hodgkin lymphomas, which are defined as being all lymphomas except Hodgkin lymphoma, are more common than Hodgkin lymphoma. A wide variety of lymphomas are in this class, and the causes, the types of cells involved, and the prognosis vary by type. The incidence of non-Hodgkin lymphoma increases with age. It is further divided into several subtypes.

The WHO classification, published in 2001 and updated in 2008 is based upon the foundations laid within the "revised European-American lymphoma classification" (REAL). This system groups lymphomas by cell type (i.e. the normal cell type that most resembles the tumor) and defining phenotypic, molecular, or cytogenetic characteristics. The five groups are:

1. Mature B cell neoplasms
2. Mature T cell and NK cell neoplasms
3. Precursor lymphoid neoplasm
4. Hodgkin lymphoma
5. Immunodeficiency-associated lymphoproliferative disorders Lymphoma is the most common blood cancer in young people aged 15 to 24, and over 14,000 new cases of lymphoma are diagnosed in the UK each year.

Current treatment may involve one or more of the following: chemotherapy, radiation therapy, targeted therapy, and surgery. In some non-Hodgkin lymphomas, an increased amount of protein produced by the lymphoma cells causes the blood to become so thick that plasmapheresis is performed to remove the protein.

In one aspect of the invention the haematological cancer is a lymphoma.

The haematological cancer according to the invention may alternatively be a myeloma. Myeloma is a cancer of plasma cells (a type of white blood cell normally responsible for producing antibodies) which develop in the bone marrow. Myeloma cells may travel through the blood stream and collect in other bones. As myeloma frequently occurs at many sites in the bone marrow, it is often referred to as multiple myeloma.

Initially, often no symptoms are noticed. When advanced, bone pain, bleeding, frequent infections, and anaemia may occur. Complications may include amyloidosis. The overproduction of myeloma cells in the bone marrow affects the production of the different types of cells that make up blood: white cells, red cells and platelets. Myeloma cells may also cause damage to bones, which can leave them prone to breaking.

Myeloma generally develops in older patients, although sometimes it is found in patients under the age of 40. Damage to the bones caused by myeloma cells can lead to hypercalcaemia. High calcium can cause dehydration and damage to the kidneys.

The prevalence of myeloma in the United States is reported to be approximately 77,600 cases with approximately 24,000 new cases in 2014. Average five-year survival rates are estimated to be less than 45% with survival rates depending on factors such as age, stage of diagnosis etc. Patients are typically treated with repeat rounds of combination therapy with the time intervals to relapse becoming shorter with each successive line of therapy. The majority of patients eventually have a relapse, which cannot be further treated. At this late stage, median survival is only six to nine months and treatment is primarily palliative to reduce symptoms and manage quality of life.

As discussed above, myeloma is a disease involving plasma cells.

Myeloma can be classified and/or stratified according to various conventions, for example see Fonseca et al. Leukemia (2009) 23, 2210-2221. There are several systems in use that characterize the bulk and aggressiveness of the disease.

For example, the International Myeloma Working Group diagnostic criteria and the International Staging System (ISS) are commonly used.

International Myeloma Working Group diagnostic criteria:

Asymptomatic/smoldering myeloma: Monoclonal (M)-protein ≥30 g/L and/or bone marrow clonal cells ≥10% but no related organ or tissue impairment (ROTI) (end-organ damage).

Symptomatic myeloma: M-protein ≥30 g/L and/or bone marrow clonal cells ≥10% and must have evidence of ROTI (end-organ damage) that can be attributed to the plasma cell proliferative process; manifested by CRAB (calcium, renal failure, anaemia, and bone lesions: increased serum calcium ≥11.5 mg/100 mL; renal insufficiency [serum creatinine >1.73 mmol/L]; normochromic, normocytic anaemia with a haemoglobin value >2 g/100 mL below the lower limit of normal or a haemoglobin value <10 g/100 mL; lytic lesions, severe osteopenia, or pathologic fractures).

Nonsecretory myeloma: Absence of an M-protein in the serum and urine, bone marrow plasmacytosis, and ROTI.

The stage of the myeloma may be classified according to the International Staging System:

Stage I: Serum beta-2 microglobulin <3.5 mg/L and serum albumin ≥3.5 g/dL

Stage II: Neither stage I nor stage III

Stage III: Serum beta-2 microglobulin ≥5.5 mg/L

References to "myeloma" herein are intended to encompass myeloma of all types and stages.

For example, the myeloma may be multiple myeloma.

The myeloma may be stage I, stage II or stage III myeloma.

Cancer Stem Cells

In another aspect of the invention, the inventor has surprisingly found that 5T4 is expressed in cancer stem cells in both haematological cancers and cancers characterised by solid tumours.

Cancer stem cells share some of the properties of normal stem cells including expression of membrane-bound multi-drug transporters and surface markers, the ability to self-renew and differentiate, and a dependence on similar signalling pathways. These properties allow CSCs to evade conventional chemotherapy, which may explain why many tumours recur following treatment (FIG. 18).

As demonstrated in the present Examples, 5T4 is expressed on stem cells in both solid tumours and haematological cancers. As used herein, "cancer stem cells" refer to cancer stem cells that possess characteristics associated with normal stem cells. For example, the ability to give rise to all cell types found in a particular cancer sample. Cancer stem cells are tumorigenic (tumour-forming) cells. Cancer stem cells can generate tumours through the stem cell processes of self-renewal and differentiation into multiple cell types. Such cells can persist in tumours as a distinct population and cause relapse and metastasis by giving rise to new tumours.

As depicted in FIG. 18, targeting cancer stem cells may improve patient outcomes as killing the cancer stem cells decreases the likelihood that tumour cells survive and go on to cause tumour relapse.

As such, targeting 5T4 present on cancer stem cells may reduce the likelihood of relapse of a cancer.

Thus, in one aspect, the present invention provides a method for preventing or reducing cancer relapse in a subject, wherein said method comprises administering a 5T4-targeting agent to said subject.

In a further aspect the invention provides a 5T4-targeting agent for use in preventing or reducing cancer relapse in a subject.

Also provided is use of a 5T4-targeting agent in the manufacture of a medicament for preventing or reducing cancer relapse in a subject, and use of a 5T4-targeting agent for preventing or reducing cancer relapse in a subject.

The term "cancer relapse" refers to the diagnosis of return, which includes radiographic diagnosis of return, or signs and symptoms of return of cancer, after a period of improvement or remission.

In one aspect of the invention is provided a method for treating a cancer metastasis, wherein said method comprises administering a 5T4-targeting agent to said subject. In a further aspect the invention provides a 5T4-targeting agent for use in treating a cancer metastasis in a subject. Also provided is use of a 5T4-targeting agent in the manufacture of a medicament for treating a cancer metastasis in a subject, and use of a 5T4-targeting agent for treating a cancer metastasis.

The invention also relates to a method for improving the survival time of cancer patients, wherein said method comprises administering a 5T4-targeting agent to said subject. In a further aspect the invention provides a 5T4-targeting agent for use in improving the survival time of cancer patients. Also provided is use of a 5T4-targeting agent in the manufacture of a medicament for improving the survival time of cancer patients, and use of a 5T4-targeting agent for improving the survival time of cancer patients.

This invention also relates to a method for reducing or eliminating cancer stem cells in cancer patients, wherein said method comprises administering a 5T4-targeting agent to said subject. In a further aspect the invention provides a 5T4-targeting agent for use in reducing or eliminating cancer stem cells in cancer patients. Also provided is use of a 5T4-targeting agent in the manufacture of a medicament for reducing or eliminating cancer stem cells in cancer patients, and use of a 5T4-targeting agent for reducing or eliminating cancer stem cells in cancer patients.

The expression "reducing cancer stem cells" encompasses reducing the number of cancer stem cells in the tumour tissue, e.g. in a given volume or in a given section area of the tumour tissue.

In one aspect the subject may have previously been treated with an alternative cancer treatment, such as a chemotherapeutic agent. The subject may be refractory to at least one cancer therapy, such as a chemotherapy treatment. The subject may be in relapse after a previous treatment with a cancer therapy, such as a chemotherapy treatment. The cancer may be a drug resistant cancer.

In one aspect the cancer is a haematological cancer as described herein.

In one aspect the haematological cancer may be selected from chronic lymphocytic leukaemia, multiple myeloma, acute myeloid leukaemia and B cell acute lymphoblastic lymphoma.

In one aspect the cancer is characterised by a solid tumour, wherein said cancer is not head and neck squamous cell carcinoma (HNSCC), non small cell lung cancer (NSCLC), breast cancer or gastric cancer. In one aspect the cancer is not head and neck squamous cell carcinoma (HNSCC), non small cell lung cancer (NSCLC), breast cancer, prostate cancer, hepatocellular carcinoma, gastric cancer or pancreatic cancer.

By way of non-limiting example, cancers characterised by solid tumours include bile duct, bone, bladder, brain/CNS, cervical, endometrial, muscle, mesothelioma, neuronal, oesophageal, ovarian, pleural/peritoneal membranes, renal, skin, small cell lung cancer (SCLC), testicular, thyroid, placental, uterine and vulval cancers.

In one aspect the cancer is selected from ovarian cancer, glioblastoma, and colorectal cancer. In one aspect the cancer may be small cell lung cancer (SCLC).

In one aspect the cancer is ovarian cancer or glioblastoma.

5T4 Antigen

5T4 is a 72 kDa oncofoetal glycoprotein that is known to be expressed on over 70% of carcinomas of the kidney, breast, gastrointestinal tract, colon and ovaries. Prior to the present invention, it was not, however, thought to be expressed on haematological malignancies.

5T4 expression, as detected by histochemical staining, appears to be tumour specific with only low level sporadic staining observed in the gut and pituitary. However this level of staining is so low that it is difficult to determine if it is specific. Immunohistochemical analysis indicates that 5T4 expression is an indicator of poor prognosis in colorectal cancer, ovarian cancer, gastric cancer and non-small cell lung cancer. Additionally, when tumour cells are transduced with the cDNA encoding 5T4, they display increased motility suggesting that expression of this molecule may induce metastatic properties in a tumour.

The 5T4 antigen is the polypeptide known as 5T4 and is characterised, for example, in WO89/07947. "5T4" may be human 5T4 as characterised by Myers et al, the sequence of which appears in GenBank at accession no. Z29083. A sequence for mouse or murine 5T4 (m5T4) appears in GenBank at Accession no. AJ012160. The organisation of the mouse and human 5T4 genes is described, for example, by King et al. Biochim Biophys Acta 1999; 1445 (3); 257-70. Canine and feline 5T4 sequences are described, for example, in WO02/38612.

Sequence analysis of the human 5T4 cDNA identified the antigen as a member of the leucine rich repeat (LRR) family of proteins (Myers, K. A. et al. (1994)). The protein contains a short cytoplasmic tail of 44 amino acids and an extracellular domain consisting of two leucine rich repeat (LRR)

regions with associated cysteine containing flanking regions and separated by a hydrophilic domain. All of the seven consensus NxS/T N-glycosylation sites in the extracellular domain are glycosylated with a combination of complex glycans, including two high mannose chains and five sialylated, bi- to tetra-antennary complex chains with minor quantities of core fucosylation (Shaw, D. M. et al. (2002)).

Sequence comparisons between the human and mouse 5T4 cDNAs (King et al. (1999)) indicates the highly conserved structure of 5T4 molecules between species. These molecules share 81% amino acid identity, with the cytoplasmic and transmembrane domains being completely conserved. Of the seven N-linked glycosylation sites in the human molecule, six are conserved in the mouse. The most N-terminal site (N81) is absent, but an additional site (N334) in the C-terminal flanking region is present predicting a similar level of glycosylation to the human molecules. The murine protein contains an additional six amino acids adjacent to the glycosylation site in the hydrophilic domain, which is a direct repeat of the preceding six amino acids. The expression of 5T4 in trophoblasts suggests it is present at a stage of development common to all mammals. This makes it likely that 5T4 is highly conserved throughout mammals.

The expression "5T4 antigen" or "5T4" as used herein encompasses fragments thereof, and preferably those fragments having distinct epitopes, and variants thereof comprising amino acid insertions, deletions or substitutions which retain the antigenicity of 5T4. Suitably, the term 5T4 antigen, includes peptides and other fragments of 5T4 which retain at least one common antigenic determinant of 5T4.

Thus 5T4 antigen as referred to herein includes amino acid mutants, glycosylation variants and other covalent derivatives of 5T4 which retain the physiological and/or physical properties of 5T4. Exemplary derivatives include molecules wherein the 5T4 is covalently modified by substitution, chemical, enzymatic, or other appropriate means with a moiety other than a naturally occurring amino acid. Such a moiety may be a detectable moiety such as an enzyme or a radioisotope.

Further included are naturally occurring variants of 5T4 found within a particular species, preferably a mammal. Such a variant may be encoded by a related gene of the same gene family, by an allelic variant of a particular gene, or represent an alternative splicing variant of the 5T4 gene.

Derivatives which retain common antigenic determinants can be fragments of 5T4. Fragments of 5T4 comprise individual domains thereof, as well as smaller polypeptides derived from the domains. Preferably, smaller polypeptides derived from 5T4 according to the invention define a single epitope which is characteristic of 5T4. Fragments may in theory be almost any size, as long as they retain one characteristic of 5T4. Preferably, fragments will be between 5 and 400 amino acids in length. Longer fragments are regarded as truncations of the full-length 5T4 and generally encompassed by the term "5T4". Advantageously, fragments are relatively small peptides of the order of 5 to 25 amino acids in length. Preferred are peptides about 9 amino acids in length.

Derivatives of 5T4 also comprise mutants thereof, which may contain amino acid deletions, additions or substitutions, subject to the requirement to maintain at least one feature characteristic of 5T4. Thus, conservative amino acid substitutions may be made substantially without altering the nature of 5T4, as may truncations from the 5' or 3' ends. Deletions and substitutions may moreover be made to the fragments of 5T4 comprised by the invention. 5T4 mutants may be produced from a DNA encoding 5T4 which has been subjected to in vitro mutagenesis resulting e.g. in an addition, exchange and/or deletion of one or more amino acids. For example, substitutional, deletional or insertional variants of 5T4 can be prepared by recombinant methods and screened for immuno-crossreactivity with the native forms of 5T4.

The fragments, mutants and other derivatives of 5T4 preferably retain substantial homology with 5T4. As used herein, "homology" means that the two entities share sufficient characteristics for the skilled person to determine that they are similar in origin and function.

"Substantial homology", where homology indicates sequence identity, means more than 40% sequence identity, preferably more than 45% sequence identity and most preferably a sequence identity of 50% or more, as judged by direct sequence alignment and comparison.

Targeting 5T4

By "targeting" it is meant that a therapeutic or prophylactic intervention is based on, or directed to, the 5T4 antigen. This may comprise, for example, an active immunotherapy approach, such as administering an immunological composition or vaccine comprising a 5T4 antigen to a subject. Alternatively, a passive immunotherapy approach may be taken, for example adoptive T cell transfer or B cell transfer, wherein a T or B cell or T and B cells which recognise a 5T4 antigen are isolated from tumours, or other bodily tissues (including but not limited to lymph node, blood or ascites), expanded ex vivo or in vitro and readministered to a subject. Such T or B cells may be engineered to recognise a 5T4 antigen.

In a further alternative an antibody which recognises the 5T4 antigen may be administered to a subject. In one aspect such antibody may be modified to deliver a cytotoxic payload to cells expressing the 5T4 antigen.

As discussed herein, in another aspect 5T4 antibody-drug conjugates may be used. Antibody-drug conjugates (ADCs) combine the binding specificity of monoclonal antibodies with the potency of chemotherapeutic agents. An example is an antibody-drug conjugate comprising a specific antibody containing non-natural amino acid and dolastatin linker derivative useful for treating 5T4-positive cancer e.g. colorectal and breast cancer in a patient (see for example WO2013/068874).

One skilled in the art will appreciate that for a cell surface antigen, an antibody will recognise the antigen. Where the antigen is an intracellular antigen, the antibody recognises the antigen peptide:MHC complex. An antibody which "recognises" an antigen encompasses both of these possibilities.

As defined herein "treatment" refers to reducing, alleviating or eliminating one or more symptoms of the disease which is being treated, relative to the symptoms prior to treatment.

"Prevention" (or prophylaxis) refers to delaying or preventing the onset of the symptoms of the disease. Prevention may be absolute (such that no disease occurs) or may be effective only in some individuals or for a limited amount of time.

In one aspect of the invention as described herein, the subject is a mammal, preferably a cat, dog, horse, donkey, sheep, pig, goat, cow, mouse, rat, rabbit or guinea pig, but most preferably the subject is a human.

In one aspect of the invention as described herein the method of treatment or prevention of cancer according to the invention comprises the step of identifying a subject in need of said treatment or prevention.

In one aspect of the invention as described herein, a tumour sample obtained from a patient may be analysed or screened for 5T4 expression prior to administration of a 5T4-targeting agent. For example, the sample may be a tumour sample, a blood sample or a tissue sample or a peripheral blood mononuclear cells sample from the subject. In one aspect the sample may be a bone marrow sample. A 5T4-targeting agent may be administered according to the invention to patients whose tumour samples show 5T4 expression. That is, the cancer according to the invention may be a 5T4-positive cancer, i.e. comprises a cell that expresses 5T4.

Antibodies

In one aspect, the 5T4-targeting agent is an antibody. That is, an antibody which recognises or is specific to 5T4, i.e. the antibody binds specifically to the 5T4 antigen.

"Specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least two-fold, more typically by at least 10-fold, often at least 100-fold; when used to detect analyte, specific binding is sufficiently discriminatory when determinative of the presence of the analyte in a heterogeneous (inhomogeneous) sample.

"Antibody" (Ab) includes monoclonal antibodies, polyclonal antibodies, multispecific antibodies (e.g., bispecific antibodies), and antibody fragments that exhibit the desired biological activity. Antibody fragments may be fragments comprising at least one antibody-antigen binding site. Antibody fragments can, for example, exhibit specific binding to 5T4 or fragments thereof. Thus, the biological activity may be the binding activity to 5T4. The term "immunoglobulin" (Ig) may be used interchangeably with "antibody".

An "antibody fragment" comprises a portion of an intact antibody, preferably the antigen binding or variable region of the intact antibody. Examples of antibody fragments include Fab, Fab', F(ab')2, and Fv fragments; linear antibodies; single-chain antibody molecules; and multispecific antibodies formed from antibody fragments.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

In one aspect the antibody is a monoclonal antibody.

The term "monoclonal antibody" as used herein refers to an antibody obtained from a substantially homogeneous population of antibodies, i.e. the individual antibodies comprising the population are identical except for possible naturally occurring mutations that may be present in minor amounts.

Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. Monoclonal antibodies may be prepared by standard methods in the art.

Monoclonal antibodies may be prepared using methods known in the art, for example hybridoma methods. In a hybridoma method, a mouse or other appropriate host animal is typically immunized with an immunizing agent to elicit lymphocytes that produce or are capable of producing antibodies that will specifically bind to the target, i.e. 5T4 in the present case.

Monoclonal antibodies may also be produced by recombinant DNA methods that are known in the art. DNA encoding suitable monoclonal antibodies may be isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

Monoclonal antibodies may include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the same biological activity.

Antibody fragments may also include insertions, deletions, substitutions, or other selected modifications of particular regions or specific amino acids residues, provided the binding activity of the fragment is not significantly altered or impaired compared to the non-modified antibody or antibody fragment.

These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods will be known to one skilled in the art and can include site-specific mutagenesis of the nucleic acid encoding the antibody fragment.

Antibodies may be humanized antibodies or human antibodies. Humanized forms of non-human (e.g., murine) antibodies are chimeric immunoglobulins, immunoglobulin chains or fragments thereof (such as Fv, Fab, Fab' or other antigen-binding sub-sequences of antibodies) which contain minimal sequence derived from non-human immunoglobulin.

Humanized antibodies include human immunoglobulins (recipient antibody) in which residues from a complementary determining region (CDR) of the recipient antibody are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may comprise at least a portion of an immunoglobulin constant region (Fc), typically that of a human immunoglobulin.

Methods for humanizing non-human antibodies are known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. As such, "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) may be used to produce a full repertoire of human antibodies in the absence of endogenous immunoglobulin production. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies may be administered to a subject in a pharmaceutically acceptable carrier. Typically, an appropriate amount of a pharmaceutically-acceptable salt is used in the formulation to render the formulation isotonic.

Examples of the pharmaceutically-acceptable carrier include saline, Ringer's solution and dextrose solution. Sustained release preparations such as semipermeable matrices of solid hydrophobic polymers containing the antibody may also be used. It will be apparent to one skilled in the art that certain carriers may be more preferable depending upon, for instance, the route of administration and concentration of antibody being administered.

Antibodies may be administered to the subject by injection (e.g., intravenous, intraperitoneal, intrapleural, subcutaneous, intramuscular), or by other methods such as infusion that ensure its delivery to the bloodstream in an effective form. The antibodies may also be administered by intratumoral or peritumoral routes, to exert local as well as systemic therapeutic effects.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered.

A typical daily dosage of an antibody used alone may be in the range of from about 1 (μg/kg to up to 100 mg/kg of body weight or more per day.

Following administration of an antibody, the efficacy of the antibody may be assessed in various ways known to one skilled in the art. For example, the size, number, and/or distribution of cancer cells in a subject receiving treatment may be monitored. A therapeutically-administered antibody that arrests tumour growth, results in tumour shrinkage, and/or prevents the development of new tumours, compared to the disease course that would occurs in the absence of antibody administration, is an efficacious antibody for treatment of cancer.

According to the present invention the antibody is a 5T4-specific antibody.

5T4-specific antibodies are commercially available, for example, from R&D Systems (MN, USA), LifeSpan BioSciences, Inc (WA, USA) and Creative Biolabs (NY, USA).

Examples of 5T4-specific antibodies are also described in WO 98/55607, WO2001/036486, WO2003/038098, WO2006/031653, US2006/0088522, US2016/0185859, WO2007/106744, WO2012/131527 and WO2013/068874.

Single chain anti-5T4 antibodies have also been described, as well as fusion proteins that include anti-5T4 antibody sequences fused to a therapeutic molecule. For example, anti-5T4 antibody sequences fused to the human IgG1 constant domain or the extracellular domain of murine B7.1 induces cytolysis of 5T4-expressing tumor cell lines (Myers et al. (2002) Cancer Gene Ther. 9: 884-96, Shaw et al. (2000) Biochim. Biophys. Acta. 1524: 238-46; U.S. patent application Publication No. 2003/0018004). Similarly, a single chain anti-5T4 antibody fused to a superantigen may stimulate. T cell-dependent cytolysis of non-small cell lung carcinoma cells in vitro (Forsberg et al. (2001) Br. J. Cancer 85: 129-36). A phase I clinical trial using PNU-214936, a murine Fab fragment of the monoclonal antibody 5T4 fused to a mutated superantigen staphylococcal enterocytotoxin A (SEA), showed limited cytotoxicity and some anti-tumor response (Cheng et al. (2004) J. Clin. Oncol. 22(4):602-609). A phase 3 trial of this product also published in Hawkins et al. Clin Cancer Res. 2016 Jul. 1; 22(13):3172-81. doi: 10.1158/1078-0432.CCR-15-0580. Epub 2016 Feb. 5.

In one aspect the antibody may be an H8 antibody (see Hole and Stern 1988 Br. J. Cancer 57:239-246), or an antibody based on the H8 antibody. The H8 antibody recognizes a conformational epitope of the 5T4 antigen (see e.g. Shaw et al. (2002) Biochem. J. 363: 137-45, WO98/55607), a rat monoclonal antibody (Woods et al. (2002) Biochem. J. 366: 353-65), and the 5T4 mouse monoclonal antibody (U.S. Pat. No. 5,869,053).

H8 5T4-specific antibodies are commercially available, for example from R&D Systems.

In another aspect the antibody that binds the 5T4 antigen may be a 2E4 antibody, as described in the present Examples, or an antibody based on the 2E4 antibody.

The sequence of the 2E4 antibody is set out in SEQ ID NO:12:

MEVQLQQSGPELVKPGASVKISCKASGYSFTGYYMHWVKQSHVKSLEWIG

RINPYNGATTYNQDFKDKASLTVDKSSSTASMELHSLTSEDSAVYYCALS

TMITTAWFAYWGQGTLVTVSPGGGGSGGGGTGGGGSNFVMTQTPKFLLAS

AGDRVTISCKASQSVSNDVGWYQQKPGQSPKLLIYFASNRYTGVPDRFIG

SGYGTDFTFTISTVQAEDLAVYFCQQDYSSPFTFGSGTKLEIK

Peptides and Vaccines

Cancer vaccines have been proposed, which contain cancer antigens or peptides from cancer antigens.

The present invention provides an immunological composition or vaccine comprising a 5T4 antigen or 5T4 antigen peptide as defined herein for use in treating or preventing a haematological cancer.

As discussed above, the sequences of various 5T4 antigen molecules are known in the art, and peptides or proteins may be derived therefore for use according to the present invention.

Suitable peptides may be as set out in, for example, WO2000/029428, WO2006/120473, WO2007/034188, Mulryan et al. (2002) Mol. Cancer Ther. 1: 1129-37; UK Patent Application Publication Nos. 2,370,571 and 2,378,704; EP Patent Application Publication Nos. EP 1,160,323 and 1,152,060, which are herein incorporated by reference.

The immunological composition or vaccine may be used in any of the methods or used as described herein for treating or preventing a haematological cancer according to the invention. As such, the invention encompasses a method of treating or preventing a haematological cancer in a subject comprising administering an immunological composition or vaccine according to the invention.

The term "peptide" is used in the normal sense to mean a series of residues, typically L-amino acids, connected one to the other typically by peptide bonds between the α-amino and carboxyl groups of adjacent amino acids. The term includes modified peptides and synthetic peptide analogues.

The peptide may be made using chemical methods (Peptide Chemistry, A practical Textbook. Mikos Bodansky, Springer-Verlag, Berlin.). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from the polypeptide which is or comprises the antigen. The composition of a peptide may be confirmed by amino acid analysis or sequencing (e.g., the Edman degradation procedure).

The immunological composition or vaccine may be a pharmaceutical composition which additionally comprises a pharmaceutically acceptable carrier, diluent or excipient. The pharmaceutical composition may optionally comprise one or more further pharmaceutically active polypeptides and/or compounds. Such a formulation may, for example, be in a form suitable for intradermal or subcutaneous administration, or for intravenous, or intraperitoneal infusion. See, for example, Butterfield, B M J. 2015 22; 350 for a discussion of cancer vaccines.

The composition may additionally comprise an adjuvant. Examples of adjuvants include but are not limited to aluminium salts, oil emulsions and bacterial components (e.g. LPS and liposomes).

In one aspect the vaccine may comprise a 5T4 antigen in the form of a peptide, protein or alternatively a DNA or RNA molecule which encodes the peptide or protein.

In addition a 5T4 antigen vaccine may be delivered in the context of a cell. For example, the 5T4 antigen or peptide may be either expressed, pulsed or loaded onto a cell, for example an antigen presenting cell, and the cell is then administered to the subject.

One example of this is a dendritic cell vaccine pulsed or loaded with the antigen(s) or peptide(s), or genetically modified (via DNA or RNA transfer) to express one, two or more antigens (see e.g. Butterfield 2015 supra). Methods of preparing dendritic cell vaccines are known in the art.

The cell according to the vaccine as discussed herein may be an antigen presenting cell, preferably a dendritic cell.

Suitable vaccines may also be in the form of DNA or RNA vaccines relating to 5T4 antigens as described herein. For example, DNA or RNA encoding 5T4 antigen, or peptide or protein derived therefrom may be used as the vaccine, for example by direct injection to a subject. The one or more 5T4 antigens may be delivered via a bacterial or viral vector containing DNA or RNA sequences which encode one or more antigens.

Vaccines as described herein may be administered in any suitable way. For example, vaccines may be delivered by any suitable delivery mechanism as known in the art. The vaccine may involve the use of a vector delivery system, or a vector delivery system may not be necessary. Vectors may be viral or bacterial. Suitable viral vectors may be derived from retroviruses adenoviruses, lentiviruses or pox viruses. Liposomes may be used as a delivery system. *Listeria* vaccines or electroporation may also be used.

Cell-based vaccines may be prepared ex vivo and then administered to the subject.

The invention further provides a cell expressing a 5T4 antigenic molecule, or a part thereof, such as a 5T4 peptide, on its surface, or a population thereof, which cell is obtainable (or obtained) by any of the methods herein for use in treating or preventing a haematological cancer.

For in vivo administration of the cells, any mode of administration of the cell population which is common or standard in the art may be used, e.g. injection or infusion, by an appropriate route. In one aspect $1 \times 10^4$ to $1 \times 10^8$ cells may be administered per kg of subject. In one aspect about or not more than $10^7$ cells per kg of subject may be administered. Thus, for example, in a human, a dose of $0.1-20 \times 10^7$ cells per kg of subject may be administered in a dose, i.e. per dose, for example as dose of T cells or a vaccination dose. In one aspect, between $1 \times 10^4$ to $1 \times 10^5$ cells, between $1 \times 10^5$ to $1 \times 10^6$ cells, between $1 \times 10^6$ to $1 \times 10^7$ cells or between $1 \times 10^7$ to $1 \times 10^8$ cells per kg of subject may be administered. For vaccination applications, $1-20 \times 10^6$ cells per dose may be used. The dose can be repeated at later times if necessary.

A vaccine may also be in the form of DNA or RNA coding for 5T4 and delivered by additional methods including but not limited to viral vectors, antigen presenting cells and electroporation.

Immunological compositions or vaccines described herein may be used in methods according to the invention. That is, the invention encompasses a method for treating or preventing a haematological cancer in a subject, comprising administering an immunological composition comprising a 5T4 antigen, such as a 5T4 peptide.

In one aspect the vaccination is therapeutic vaccination. In this aspect the immunological composition or vaccine is administered to a subject who has a haematological cancer to treat the haematological cancer.

In a further aspect the vaccination is prophylactic vaccination. In this aspect the immunological composition is administered to a subject who may be at risk of developing a haematological cancer.

In one aspect the vaccine is administered to a subject who has previously had a haematological cancer and in whom there is a risk of the a haematological cancer recurring.

The dose of antigen to be used in the immunological composition may depend on the antigen which is to be used. For in vivo use of a protein antigen the dose may be in the range 0.5-500 µg, for example 10-100 µg or 10-200 µg. For peptide antigens an in vivo dose of 0.1-4000 µg, e.g. 0.1-2000 µg, 0.1-1000 µg or 0.1-500 µg, for example 0.1-100 µg, may be employed.

The immunological composition or vaccine according to the invention may lead to generation of an immune response in the subject. An "immune response" which may be generated may be humoral and/or cell-mediated immunity, for example the stimulation of antibody production, or the stimulation of cytotoxic or killer cells, which may recognise and destroy (or otherwise eliminate) cells expressing "foreign" antigens on their surface. The term "stimulating an immune response" thus includes all types of immune responses and mechanisms for stimulating them and encompasses stimulating CTLs which forms a preferred aspect of the invention. Preferably the immune response which is stimulated is cytotoxic CD8 T cells and helper CD4+T Cells. The extent of an immune response may be assessed by markers of an immune response, e.g. secreted molecules such as IL-2 or IFNγ or the production of antigen specific T cells.

In one aspect the TroVax® vaccine may be used.

TroVax® (Oxford BioMedica plc) consists of a highly attenuated strain of vaccinia virus (VV), termed Modified Vaccinia Ankara, (MVA), and contains the human 5T4 glycoprotein gene under regulatory control of a modified promoter, mH5. (See for example, Amato et al. Clin Cancer Res; 16(22) Nov. 15, 2010; Harrop et al. Cancer Immunol Immunother. 2012 December; 61(12):2283-94; Harrop R et al. Cancer Immunol Immunother. 2013 September; 62(9): 1511-20, WO 2000/29428, WO 2010/007365, WO 2010/079339, and WO 2012/059750.)

TroVax® may be used in the methods and/or uses described herein.

Heterologous prime boost vaccination regimens may be used as described in WO 98/56919 (generation of a protective CD8+ T cell immune response against target antigens using different primer and booster compositions as sources of CD8+ T cell epitopes), or WO 2001/021201 (use of a replication-deficient adenoviral vector encoding an antigen or a CD8+ T cell epitope of the antigen to boost in the individual a CD8+ T cell immune response to the antigen following prior administration of a priming composition). The priming composition may comprise the antigen or epitope or nucleic acid encoding the antigen or epitope, and may be DNA, Ty-LVP'S or Modified Virus Ankara (MVA)), and WO 2012/172277 (using chimpanzee adenovirus for eliciting or boosting an immune response) may be used for the administration of vaccines targeting 5T4.

Cell Therapy

In a further aspect the invention provides a cell, preferably an immune cell, such as a T cell or a Natural Killer (NK) cell or an NK T cell which recognises 5T4 for use in the treatment or prevention of a haematological cancer in a subject. Alternatively put, the invention provides the use of an immune cell, such as a T cell, an NK cell or an NKT cell, which recognises 5T4 in the manufacture of a medicament for use in the treatment or prevention of a haematological cancer in a subject. In a further alternative the invention provides the use of an immune cell, preferably a T cell which recognises 5T4 in treating or preventing a haematological cancer in a subject. In one aspect such 5T4 targeting cells are tumour infiltrating lymphocytes (TILs). In one aspect the subject is mammalian, preferably human.

References to "an immune cell" are intended to encompass cells of the immune system, for example T cells, NK cells, NKT cells, B cells or dendritic cells. In one aspect the immune cell is a T cell. In a further aspect the immune cell is an NK cell or an NKT cell.

In one aspect the invention provides a population of cells which recognise 5T4 for use in the treatment or prevention of a haematological cancer in a subject. Alternatively put, the invention provides the use of a population of cells which recognise 5T4 in the manufacture of a medicament for use in the treatment or prevention of a haematological cancer in a subject. In a further alternative the invention provides the use of a population of cells, which recognise 5T4 in treating or preventing a haematological cancer in a subject. In one aspect the cell is an immune cell as described herein. Preferably the cells are T cells, NK cells or NKT cells.

The cell or cell population may be in the form of a composition, for example a pharmaceutical composition as described herein. In some embodiments, the pharmaceutical composition further comprises other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

In addition, buffering agents in some aspects may be included in the composition. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

Cell therapy may be carried out by autologous transfer, in which the cells are isolated and/or otherwise prepared from the subject who is to receive the cell therapy, or from a sample derived from such a subject. Thus, in one aspect, the cells are derived from a subject, e.g., patient, in need of a treatment and the cells, following isolation and processing are administered to the same subject.

Alternatively, the cell therapy may be carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. In alternative embodiments the allogeneic T cells may lack a functional T cell receptor (TCR) and/or human leukocyte antigen (HLA) such as HLA class I and/or HLA class II.

The pharmaceutical composition in some embodiments comprises the cells in amounts effective to treat or prevent the disease or condition, such as a therapeutically effective or prophylactic ally effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The present invention also provides a method for providing a cell population which targets 5T4 which comprises the steps of:

i) isolating a cell from a sample isolated from the subject; and ii) expanding the cell to provide a cell population which targets 5T4.

In one aspect the cell is a T cell. In one aspect the cell is a NK or NKT cell.

The sample may be a tumour, blood or tissue sample from the subject.

In one embodiment, the sample from which the cell is isolated may be a blood sample, a tumour sample, a tumour-associated lymph node sample or a sample from a metastatic site.

When the cell is a T cell, the population of T cells may comprise $CD8^+$ T cells, $CD4^+$ T cells or $CD8^+$ and $CD4^+$ T cells.

The resulting cell population may have an increased number of cells which target 5T4 (for example, compared with the sample isolated from the subject).

The T cell may have been rendered resistant to immune suppression, for example by gene editing of immune regulatory receptors (including but not restricted to Lag 3, PD1, TIGIT, PD-L1, BTLA, CTLA4, TGFbeta Receptor, IL10 Receptor).

In one aspect, a cell may be used which is an engineered cell, such as an engineered immune cell including: a genetically engineered antigen receptor that specifically binds to a target antigen. Cells suitable for modification may be obtained from a subject, such as a mammalian subject including but not limited to a human subject. Cells may be obtained from a number of sources, known to the skilled person, including peripheral blood mononuclear cells, bone marrow, lymph node tissue, cord blood, thymus tissue, tissue from a site of infection, ascites, pleural effusion, spleen tissue and tumours. Suitable cells include cells of the immune system, such as cells of the innate or adaptive immune systems (e.g. myeloid or lymphoid cells, including lymphocytes, such as T cells, NK cells or an NKT cells. Other suitable cells include stem cells, such as multipotent and pluripotent stem cells, including induced pluripotent stem cells (iPSCs). In one aspect the cells are primary cells, such as those isolated directly from a subject and/or isolated from a subject and frozen.

In certain aspects suitable cells may be obtained from a unit of blood collected from a mammalian subject using a number of techniques known to the skilled person such as Ficoll separation. In one aspect cells from the circulating blood of an individual are obtained by apheresis. The apheresis product typically contains lymphocytes, including T cells, monocytes, granulocytes, B cells, other nucleated white blood cells, red blood cell, and platelets. The cells collected by apheresis may be washed to remove the plasma fraction and, optionally, may be placed in an appropriate buffer or medium for subsequent processing steps. Cells may be washed, for example in phosphate buffered saline. As the absence of calcium can lead to increased activation of T cells, in certain embodiments the wash solution lacks calcium and/or magnesium or may lack many or all divalent cations.

The cells may be depleted of T regulatory cells (CD25+ cells) using methods known in the art such as the Miltenyi CD25 microbeads. The depletion of CD25+ cells may be performed prior to apheresis or during production of the CAR-expressing cells (for example T cells or NK cells). Other cell types that negatively affect expansion and/or function of cells expressing a CAR may also be removed. Such immune suppressor cells include cells expressing CD14, CD11b, CD33, CD15, or other markers of immune suppressor cells and may be removed from a population of cells by using methods known to the skilled person, such as magnetic immunoadherence or flow cytometry using monoclonal antibodies directed to cell surface markers.

The cells may also be depleted of cells which express one or more check-point inhibitors, for example PD1, CD223 (LAG3), PD-L1 and CTLA4, PD-L2, TIM3, CEACAM-1, CEACAM-3, CEACAM-5, VISTA, BTLA, TIGIT, LAIR1, CD160, 2B4, CD80, CD86, CD276 (B7-H3), B7-H4 (VTCN1), CD270 (HVEM or TNFRSF14), KIR, A2aR, MHC class I MHC class II, GALS, adenosine, TGFbeta receptor. A cell population may be depleted of cells expressing one or more check-point inhibitors at the same time as depletion of T regulatory cells.

Depletion of T regulatory cells, immune suppressor cells and cells expressing check-point inhibitors may be performed at the same time for example using beads expressing multiple antibodies that recognised such T regulatory cells, immune suppressor cells or check-point inhibitors or a mixture of beads expressing such antibodies. For example an anti-CD25 antibody or fragment thereof, or other binding moiety, and an anti-check-point inhibitor antibody or fragment thereof, or other binding moiety can be attached to the same bead or to a mixture of separate beads for simultaneous depletion. Alternatively depletion of certain cell types may be performed sequentially.

In one aspect the cells may be positively selected, for example by incubation with anti-CD3/anti-CD28-conjugated beads (eg Dynabeads® Human T-Activator CD3/CD28, or other suitable reagents.

In some aspects the affinity-based selection is via magnetic-activated cell sorting (MACS) (Miltenyi Biotec, Auburn, Calif.). MACS systems are capable of high-purity selection of cells having magnetic particles attached to them. MACS can operate in a mode where the target and non-target cells are sequentially eluted after the application of the external magnetic field. Cells attached to the magnetic particles are retained while the unattached cells are eluted then the cells that were held in the magnetic field may also be eluted. In certain aspects a closed system is used to carry out one or more of the isolation, cell preparation, separation, processing, incubation, culture, and/or formulation, for example to reduce handling. Closed systems are described in WO 2009/070003 or WO 2009/072003.

Immune cells may be activated and expanded ex vivo or in vitro, by methods known in the art, for example as described in WO 01/62895, WO 2016/196388, EP1586655, U.S. Pat. Nos. 5,199,942, 6,352,694, 7,144,575, 7,067,318, 7,172,869, 7,572,631. Following collection of mammalian CD34+ haematopoietic stem and progenitor cells from a peripheral blood harvest or from bone marrow explants, such cells may be expanded ex vivo in the presence of certain growth factors. In addition to the growth factors described in WO 92/21402, other factors such as flt3-L, IL-1, IL-3 and c-kit ligand can be used for culturing and expanding cells.

A population of immune cells may be expanded by contact with an agent and/or ligand attached to a surface, for example a 5T4 antigen, such as presented by an antigen presenting cell. Alternatively, such agent may stimulate the CD3/TCR complex associated signal and the ligand may stimulate a co-stimulatory molecule present on the surface of the cells. In one aspect T cell populations may be stimulated by contact with an anti-CD3 antibody or antigen-binding fragment thereof, or an anti-CD2 antibody immobilized on a surface, or by contact with a protein kinase C activator (e.g. bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody under conditions appropriate for stimulating proliferation of the T cells. To stimulate proliferation of either CD4+ T cells or CD8+ T cells, an anti-CD3 antibody and an anti-CD28 antibody and may be used.

In certain aspects immune cells (such as PBMCs or T cells) are expanded and stimulated by contacting the cells to one of both of an anti-CD3 antibody and IL-2. Cells may be expanded without anti-CD3 or anti-CD28 beads.

In one aspect the two agents are immobilized on beads, either on the same bead or on separate beads. By way of example, the agent providing the primary activation signal is an anti-CD3 antibody or antigen-binding fragment thereof, and the agent providing the co-stimulatory signal is an anti-CD28 antibody or antigen-binding fragment thereof; both agents are co-immobilized to the same bead. In one aspect equivalent molecular amounts of each antibody are bound to the beads to stimulate CD4+ T cell expansion and T cell growth. In certain aspects, a ratio of CD3:CD28 antibodies is bound to the beads such that an increase in T cell expansion is observed as compared to the expansion observed using such antibodies at a ratio of 1:1. In one aspect the ratio of CD3:CD28 antibody bound to the beads ranges from between 100:1 to 1:100. In one aspect more anti-CD28 antibody than anti-CD3 antibody is used.

In further aspects cells such as T cells, NK cells or NK-T cells are combined with agent-coated beads, the beads and the cells are subsequently separated and then the cells are cultured. Alternatively, prior to culture the agent-coated beads and cells are cultured together. Alternatively the beads and cells are first concentrated by the application of a force such as a magnetic force, resulting in increased binding of cell surface markers, thereby inducing cell stimulation. In certain aspects the beads are paramagnetic beads (such as Dynabeads or MACS beads).

In some aspects, the separation and/or other steps are carried out using the CliniMACS system (Miltenyi Biotec).

In one aspect, cells incorporating a nucleic acid encoding a CAR are expanded. Cells may be expanded in culture for a period between several hours to about 14 days. In certain aspects the cells may be expanded for longer than 14 days, particularly where several cycles of stimulation are performed.

Conditions suitable for cell culture will be known to the skilled person and include use of an appropriate culture medium (e.g., Minimal Essential Medium (MEM), DMEM, α-MEM, F12, RPMI 1640, X-vivo 15, X-vivo 20, Optimzer, AIM-V, TexMACs). The culture media may contain factors to improve proliferation and viability of the cells such as serum (human serum or foetal bovine serum), IL-2, insulin, IFN-γ, IL-4, IL-7, GM-CSF, IL-10, IL-12, IL-15, TGFβ, TNF-α or any other such additives known by the skilled person to increase proliferation and viability of cells. Cells will be maintained under conditions necessary to support growth, for example, an appropriate temperature (e.g. 37° C.) and atmosphere (e.g., air plus 5% $CO_2$).

The cells described herein may express a chimeric antigen receptor (CAR) or a T cell receptor (TCR) which specifically binds 5T4, or an affinity-enhanced TCR which specifically binds 5T4. Thus, the cell may be engineered to express a 5T4-specific CAR or TCR.

In one aspect the antigen-binding moiety of the engineered cell is a chimeric T cell receptor (TCR). Such TCRs may be recombinant TCRs or TCRs cloned from naturally occurring T cells.

A further option for targeting 5T4 therefore involves the use of cells, such as T cells, NK cells or NKT cells expressing CARs or TCRs specific for 5T4.

The cells may be engineered ex vivo to be specific to a particular antigen, and the autologous antigen-specific cells administered to a subject.

CARs and TCRs are discussed in further detail below, but various methods for the introduction of genetic components (such as CARs or TCRs) into cells, are well known in the art. Exemplary methods include viral transduction, e.g. using retroviral or lentiviral vectors, transposons, electroporation, and DNA targeting proteins such as zinc finger proteins, transcription activator-like protein fused to effector proteins such as an endonuclease (e.g., TALEs and TALENS) (June et al. 2009 Nature Reviews Immunology 9.10; 704-716).

In some aspects gene transfer is accomplished by first stimulating cell growth and/or activation, followed by transduction of the cells, and then followed by expansion of the modified cells to numbers sufficient for clinical applications.

Recombinant nucleic acids may be transferred into cells using recombinant infectious virus particles. Vectors derived from retroviruses, such as lentiviruses, are suitable for achieving long-term gene transfer since they allow long-term stable integration of a transgene and its propagation in daughter cells. Vectors derived from lentiviruses can also transduce non-dividing cells.

Suitable retroviral vectors include those derived from γ-retroviruses such as Murine Leukaemia Virus (MLV), Spleen-Focus Forming Virus (SFFV), human T-cell leukaemia virus (HTLV), mouse mammary tumour virus (MMTV), Rous sarcoma virus (RSV), Fujinami sarcoma virus (FuSV), Moloney murine leukaemia virus (Mo MLV), FBR murine osteosarcoma virus (FBR MSV), Moloney murine sarcoma virus (Mo-MSV), Abelson murine leukaemia virus (A-MLV), Avian myelocytomatosis virus-29 (MC29) and Avian erythroblastosis virus (AEV) and Myelopoliferative Sarcoma Virus (MPSV). A detailed list of retroviruses may be found in Coffin et al. (1997) "Retroviruses", Cold Spring Harbour Laboratory Press Eds: J M Coffin, S M Hughes, H E Varmus pp 758-763. Suitable lentiviral vectors may be derived from HIV-1, HIV-2, SIV, FIV, BIV, EIAV, CAEV or visna lentivirus and are described in U.S. Pat. Nos. 6,924,123, 7,056,699, WO 98/17815, WO 99/32646, WO 01/79518, WO 03/064665, U.S. Pat. No. 6,969,598.

The vector may also include the TRiP system described in WO 2015/092440 which prevents expression of the transgene during vector production.

Other vectors suitable for transducing the cells described herein include vectors derived from simian virus 40 (SV40), adenoviruses, adeno-associated virus (AAV). (see, e.g., Koste et al. (2014) Gene Therapy 2014 Apr. 3. doi: 10.1038/ gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November; 29(11): 550-557).

Recombinant nucleic acids may be transferred into the cells described herein via electroporation or transposition. Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Also provided are methods, nucleic acids, compositions, and kits, for producing the genetically engineered cells. The genetic engineering may involve introduction of a nucleic acid encoding the genetically engineered component or other component for introduction into the cell, such as a component encoding a gene-disruption protein or nucleic acid.

Methods for generating TCRs and affinity enhanced TCRs are known in the art. Affinity enhanced TCRs are TCRs with enhanced affinity for a peptide-MHC complex (including e.g. the isolation of TCR genes that encode TCRs from patient samples (e.g. patient peripheral blood or TILs) and the improvement of TCR affinity for a peptide-MHC complex via modification of TCR sequences (e.g. by in vitro mutagenesis and selection of enhanced affinity (or affinity matured) TCRs). Methods of introducing such TCR genes into cells (such as T cells, NK cells or NKT cells) are known in the art. Methods of identifying optimal-affinity TCRs involving the immunisation of antigen-negative humanised transgenic mice which have a diverse human TCR repertoire (e.g. TCR/MHC humanised mice such as ABabDII mice) with antigen, and isolation of antigen-specific TCRs from such immunised transgenic mice are also known in the art (see e.g. Obenaus M et al., Nat Biotechnol. 33(4):402-7, 2015). In some aspects high-affinity TCRs are generated, for example by the methods described in WO 2004/044004 or other methods known to the skilled person.

In certain aspects according to the invention as described herein the cell or cell populations or compositions are reinfused into a subject, for example following isolation and expansion of cells such as T cells, NK cells or NKT cells. Suitable methods to achieve this are described herein and will also be known to one skilled in the art. For example, for methods for generating, selecting and expanding T cells see e.g. Dudley J Immunother. 2003; 26(4): 332-342, and Rosenberg et al. 2011 Clin Cancer Res:17(13):4550-7. Methods for reinfusing T cells are described in Dudley et al. Clin Cancer Res. 2010 Dec. 15; 16(24): 6122-6131, and Rooney et al. Blood. 1998 Sep. 1; 92(5):1549-55.

In one aspect the present invention relates to a method for treating a haematological cancer in a subject which comprises administering a cell composition as described herein to the subject. The cell composition may be a T cell, NK cell or NKT cell composition.

The method may comprise the following steps:
(i) isolation of a cell containing sample from the subject;
(ii) expansion of a cell population which targets 5T4; and
(iii) administering the cells from (ii) to the subject.

The cells may be engineered to target 5T4 as described herein, e.g. using a 5T4-specific CAR or TCR.

As such, the method may comprise the following steps:
(i) isolation of a cell containing sample;
(ii) engineering the cell to express a CAR or a TCR which recognises 5T4 to provide a cell population which targets 5T4; and
(iii) expanding the engineered cells
(iv) administering the cells from (ii) or (iii) to the subject.

The method above may include an optional expansion step prior to stage (ii).

The invention also provides a method of treating a patient who has a haematological cancer comprising:
(i) identifying a patient who has a haematological cancer; and
(ii) optionally determining whether such patient's haematological cancer cells express the 5T4 antigen; and
(iii) administering to said patient a cell or cell population (or any of the 5T4-targeting agents) as defined herein.

Wherein T cells are used an expanded population of 5T4-reactive T cells may have a higher activity than a population of T cells not expanded, for example, using a 5T4 peptide. Reference to "activity" may represent the response of the T cell population to restimulation with a 5T4 peptide, or antigen e.g. a peptide corresponding to the peptide used for expansion. Suitable methods for assaying the response are known in the art. For example, cytokine production may be measured (e.g. IL2 or IFNγ production may be measured). The reference to a "higher activity" includes, for example, a 1-5, 5-10, 10-20, 20-50, 50-100, 100-500, 500-1000-fold increase in activity.

Affinity-enhanced TCRs may be generated by identifying a T cell clone from which the TCR α and β chains with the desired target specificity are cloned. The candidate TCR then undergoes PCR directed mutagenesis at the complimentary determining regions of the α and β chains. The mutations in each CDR region are screened to select for mutants with enhanced affinity over the native TCR. Once complete, lead candidates are cloned into vectors to allow functional testing in T cells expressing the affinity-enhanced TCR.

CARs are proteins which, in their usual format, graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals.

The most common form of these molecules use single-chain variable fragments (scFv) derived from monoclonal antibodies to recognize a target antigen. The scFv is fused via a spacer and a transmembrane domain to a signalling endodomain. Such molecules result in activation of the cell in which they are expressed in response to recognition by the scFv of its target. When cells express such a CAR, they recognize and kill target cells that express the target antigen. Several CARs have been developed against tumour associated antigens, and adoptive transfer approaches using such CAR-expressing cells are currently in clinical trial for the treatment of various cancers. CARs are described in, for example, WO 2014/031687.

In some aspects the antibody portion of a recombinant receptor (e.g. a CAR) further includes at least a portion of an immunoglobulin constant region, such as a hinge region, for example, an IgG4 hinge region, and/or a CH1/CL and/or Fc region. In certain aspects the portion of the constant region serves as a spacer region between the antigen-recognition component, e.g. the scFv, and the transmembrane domain. The spacer can be of a length that provides for increased responsiveness of the cell following antigen binding, as compared to responsiveness in the absence of the spacer.

Exemplary spacers include those described in WO 2014/031687. The spacer may vary in length from between about 10 to 200 amino acids.

The antigen recognition domain is generally linked to one or more intracellular signalling components such as signalling components that mimic activation through an antigen receptor complex, such as a TCR complex and optionally associated co-stimulatory signal, in the case of a CAR, and/or signal via another cell surface receptor. Thus in some aspects the antigen-binding component is linked to one or more transmembrane and intracellular signalling domains. In some aspects the transmembrane domain fused to the extracellular domain. In one aspect a transmembrane domain that is naturally associated with one of the domains in the receptor is used. In some instances the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from the alpha, beta, or zeta chain of the T cell receptor, CD28, CD3 epsilon, CD45, CD4, CD5, CD9, CD16, CD22, CD33, CD37, CD64, CD80, CD86, CD134, CD137, CD154. Alternatively the transmembrane domain may be synthetic. In some aspects the synthetic transmembrane domain comprises predominantly hydrophobic residues such as leucine and valine. In some aspects, a triplet of phenylalanine, tryptophan and valine will be found at each end of a synthetic transmembrane domain. In some aspects the linkage is via linkers, spacers, and/or transmembrane domains.

Suitable intracellular signalling domains of the recombinant receptor include those that mimic or approximate a signal through a natural antigen receptor (e.g. CD3 signal), a signal through such a receptor in combination with a co-stimulatory receptor (e.g. CD3/CD28 signal) and/or a signal through a co-stimulatory receptor alone. In some aspects, a short oligo- or polypeptide linker is present and forms a linkage between the transmembrane domain and the cytoplasmic signalling domain of the recombinant receptor such as the CAR.

A recombinant receptor such as a CAR generally includes at least one intracellular signalling component or components. In some aspects, the receptor includes an intracellular component of a TCR complex, such as a TCR CD3 chain that mediates T-cell activation and cytotoxicity, such as a CD3 zeta chain. Thus in some aspects, the antigen-binding portion is linked to one or more cell signalling domains. In some aspects, cell signalling domains include CD3 transmembrane, CD3 intracellular signalling domains, and/or other CD transmembrane domains. In some embodiments the receptor further includes a portion of one or more additional molecules such as Fc receptor γ CD8, CD4, CD25, or CD16. For example in some aspects the chimeric receptor includes a chimeric molecule between CD3-zeta (CD3-ζ) or FC receptor γ and CD8, CD4, CD25 or CD16.

In some aspects, upon binding of the CAR or other chimeric receptor, the cytoplasmic domain or intracellular signalling domain of the receptor activates at least one of the normal effector functions or responses of the immune cell, such as cytolytic activity or T-helper activity, such as secretion of cytokines or other factors. In some aspects a truncated portion of an intracellular signalling domain of an antigen receptor component or co-stimulatory molecule is used in place of an intact immunostimulatory chain, for example, if it transduces the effector function signal. In some aspects the intracellular signalling domain or domains include the cytoplasmic sequences of the T cell receptor (TCR) and in some aspects also those cytoplasmic sequences of co-receptors that in the natural context act in concert with such receptors to initiate signal transduction following antigen receptor engagement.

For a natural TCR, full activation generally requires not only signalling through the TCR, but also a co-stimulatory signal. Thus, in some aspects, to promote full activation, a component for generating secondary or co-stimulatory signal is also included in the CAR. In other aspects the CAR does not include a component for generating a co-stimulatory signal. In some aspects an additional CAR is expressed in the same cells and provides the component for generating the secondary or co-stimulatory signal.

T cell activation is in some aspects described as being mediated by two classes of cytoplasmic signalling sequences: those that initiate antigen-dependent primary activation through the TCR (primary cytoplasmic signalling sequences) and those that act in an antigen-independent manner to provide a secondary or co-stimulatory signal (secondary cytoplasmic signalling sequences). In some aspects the CAR includes one or both of such signalling components.

In some aspects the CAR includes a primary cytoplasmic signalling sequence that regulates primary activation of the TCR complex. Primary cytoplasmic signalling sequences that act in a stimulatory manner may contain signalling motifs which are known as immunoreceptor tyrosine-based activation motifs (ITAMs). TCR zeta, FcR gamma, GcR beta, CD3 gamma, CD3 delta, CD3 epsilon, CDS, CD22, CD79a, CD79b, and CD66d are examples of primary cytoplasmic signalling sequences which contain ITAMs. In certain aspects the cytoplasmic signalling domain in the CAR includes a sequence derived from CD3 zeta.

In certain aspects the CAR includes a signalling domain and/or transmembrane portion of a costimulatory receptor such as CD28, 4-1BB, OX40, DAP10 and ICOS. In some aspects the same CAR includes both the activating and costimulatory components.

In some aspects the activating domain is included within one CAR whereas the co-stimulatory component is provided by another CAR recognizing a different antigen. In some aspects the CARs include activating or stimulatory CARs, costimulatory CARs, both expressed on the same cell (see WO 2014/055668). In some aspects the cells include one or more stimulatory or activating CAR and/or a co-stimulatory CAR. In other aspects cells further include inhibitory CARs such as a CAR recognizing an antigen other than the one associated with and/or specific for the disease or condition whereby an activating signal delivered through the disease-targeting CAR is diminished or inhibited by binding of the inhibitory CAR to its ligand, for example to reduce off-target effects (iCARs, see Fedorov et al 2013, Sci Transl Med. 5: 215).

In certain aspects the intracellular signalling domain comprises a CD28 transmembrane and signalling domain linked to a CD3 (e.g. CD3-zeta) intracellular domain. In some aspects the intracellular signalling domain comprises a chimeric CD28 and CD137 (4-1BB/TNFRSF9) co-stimulatory domains linked to a CD3 zeta intracellular domain.

In some aspects the CAR encompasses one or more costimulatory domains and an activation domain e.g. primary activation domain in the cytoplasmic portion. Exemplary CARs include CD3 zeta, CD28 and 4-1BB.

In certain aspects the CAR includes an extracellular portion containing an antibody or antibody fragment. In some aspects the chimeric antigen receptor includes an extracellular portion containing the antibody or fragment and an intracellular signalling domain. In some aspects the antibody or fragment includes an scFv and the intracellular domain contains an ITAM. In some aspects the intracellular signalling domain includes a signalling domain of a zeta chain of a CD3-zeta chain. In some aspects the CAR includes a transmembrane domain linking the extracellular domain and the intracellular signalling domain. In some aspects, the transmembrane domain contains a transmembrane portion of CD28. In some aspects the CAR contains an intracellular domain of a T cell co-stimulatory molecule. In some aspects the T cell co-stimulatory molecule is CD28 or 4-1BB.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. The TCR may be modified on any cell comprising a TCR, including, for example, a helper T cell, a cytotoxic T cell, a memory T cell, regulatory T cell, natural killer T cell, and gamma delta T cell.

The TCR may be an endogenous TCR, i.e., the TCR that is endogenous or native to (naturally-occurring on) the T cell. In such a case, the T cell comprising the endogenous TCR can be a T cell that was isolated from a mammal which is known to express the particular antigen. The T cell may be a primary T cell isolated from a subject with e.g. cancer. The T cell may be a tumour infiltrating lymphocyte (TIL) or a peripheral blood lymphocyte isolated from a subject. Alternatively, a T cell comprising an endogenous antigen-specific TCR may be a T cell within a mixed population of cells isolated from a mammal, and the mixed population can be exposed to the antigen which is recognized by the endogenous TCR while being cultured in vitro. The T cell which comprises the TCR that recognizes the antigen, expands or proliferates in vitro, thereby increasing the number of T cells having the endogenous antigen-specific receptor.

The antigen-specific TCR, e.g. 5T4 specific TCR according to the present invention, may be an exogenous TCR, i.e., an antigen-specific TCR that is not native to (not naturally-occurring on) the T cell. A recombinant TCR is a TCR which has been generated through recombinant expression of one or more exogenous TCR α-, β-, γ-, and/or δ-chain encoding genes. A recombinant TCR can comprise polypeptide chains derived entirely from a single mammalian species, or the antigen-specific TCR can be a chimeric or hybrid TCR comprised of amino acid sequences derived from TCRs from two different mammalian species. For example, the antigen-specific TCR can comprise a variable region derived from a murine TCR, and a constant region of a human TCR such that the TCR is "humanized." Methods of making recombinant TCRs are known in the art. See, for example, U.S. Pat. Nos. 7,820,174; 8,785,601; 8,216,565; and U.S. Patent Application Publication No. 2013/0274203.

A T cell of the invention as described herein may comprise an endogenous antigen-specific TCR and may also be transformed, e.g. transduced or transfected, with one or more nucleic acids encoding an exogenous (recombinant) TCR or other recombinant chimeric receptor. Such exogenous chimeric receptors, e.g., chimeric TCRs, can confer specificity for additional antigens to the transformed T cell beyond the antigens for which the endogenous TCR is naturally specific.

In one aspect of the invention, any of the antigen-binding moieties as described may be multi-specific, i.e. it recognizes more than one antigen. In one aspect the antigen-binding moiety is a bi- or tri-specific antibody. A number of methods exist in the art for generating multi-specific antibodies and will be known by the skilled person.

In one aspect the antigen-binding moiety may also bind a tumour-associated antigen, including but not limited to differentiation antigens (such as melanocyte differentiation antigens), mutational antigens (such as p53), overexpressed cellular antigens (such as HER2), viral antigens (such as human papillomavirus proteins), and cancer/testis (CT) antigens that are expressed in germ cells of the testis and ovary but are silent in normal somatic cells (such as MAGE and NY-ESO-1.

5T4-Specific Car

The present invention also provides a 5T4-specific CAR comprising an extracellular ligand binding domain comprising heavy (VH) and light (VL) variable fragments from a monoclonal anti-5T4 antibody, a linker, a hinge, a transmembrane domain, and a cytoplasmic domain which includes a signalling domain and a co-stimulatory domain. The CAR according to the invention may be used in any of the methods or uses of the invention as described herein.

The Table below sets out exemplary sequences of various components of the CAR:

| SEQ ID NO | Description | Amino acid sequence |
|---|---|---|
| 2 | Oncostatin M leader | MGVLLTQRTLLSLVLALLFPSMAS |
| 3 | H8 anti5T4 domain | MEVQLQQSGPDLVKPGASVKISCKASGYSFTGYYMHWVKQSHG KSLEWIGRINPNNGVTLYNQKFKDKAILTVDKSSTTAYMELRSLTS EDSAVYYCARSTMITNYVMDYWGQVTSVTVSSGGGGSGGGGTG GGGSSIVMTQTPTFLLVSAGDRVTITCKASQSVSNDVAWYQQKP GQSPTLLISYTSSRYAGVPDRFIGSGYGTDFTFTISTLQAEDLAVY FCQQDYNSPPTFGGGTKLEIKR |

-continued

| SEQ ID NO | Description | Amino acid sequence |
|---|---|---|
| 11 | 2E4 anti5T4 domain | MEVQLQQSGPELVKPGASVKISCKASGYSFTGYYMHWVKQSHV KSLEWIGRINPYNGATTYNQDFKDKASLTVDKSSSTASMELHSLT SEDSAVYYCALSTMITTAWFAYWGQGTLVTVSPGGGGSGGGGT GGGGSNFVMTQTPKFLLASAGDRVTISCKASQSVSNDVGWYQQ KPGQSPKLLIYFASNRYTGVPDRFIGSGYGTDFTFTISTVQAEDLA VYFCQQDYSSPFTFGSGTKLEIK |
| 4 | Linker | AAA |
| 5 | CD8 hinge | LSNSIMYFSHFVPVFLPAKPTTTPAPRPPTPAPTIASQPLSLRPEA CRPAAGGAVHTRGLDFACD |
| 6 | CD8 transmembrane region | IYIWAPLAGTCGVLLLSLVITLYC |
| 7 | 41BB costimulatory domain | KRGRKKLLYIFKQPFMRPVQTTQEEDGCSCRFPEEEEGGCEL |
| 8 | CD3 zeta stimulatory domain | LRVKFSRSADAPAYQQGQNQLYNELNLGRREEYDVLDKRRGRD PEMGGKPRRKNPQEGLYNELQKDKMAEAYSEIGMKGERRRGKG HDGLYQGLSTATKDTYDALHMQALPPR |

In one aspect the 5T4-specific CAR according to the invention comprises an "anti-5T4" domain or extracellular ligand binding domain having at least 70, 75, 80, 85, 90, 91, 92, 93, 94, 95, 96, 97, 98, 99 or 100% sequence identity to SEQ ID NO:3. The anti-5T4 domain may be derived from the mouse monoclonal H8 antibody as discussed herein. In one aspect the anti-5T4 domain has at least 95%, preferably at least 98% or more preferably at least 99% sequence identity to SEQ ID NO:3.

In another aspect the anti-5T4 domain may be derived from the 2E4 antibody. The 2E4 antibody is described in the present Examples.

In one aspect the extracellular ligand binding domain comprises a VH chain comprising CDRs from the H8 monoclonal antibody and a VL chain comprising the CDRs from the mouse monoclonal H8 antibody. These sequences are known in the art—see for example WO2016/034666.

The extracellular ligand binding domain may be comprise VH and VL chains which are humanised as discussed herein.

In one aspect the 5T4-specific CAR according to the invention comprises an "anti-5T4" domain or extracellular ligand binding domain having at least 70, 75, 80, 85, 90, 91, 92, 93, 94, 95, 96, 97, 98, 99 or 100% sequence identity to SEQ ID NO:11. The anti-5T4 domain may be derived from the 2E4 antibody as discussed herein. In one aspect the anti-5T4 domain has at least 95%, preferably at least 98% or more preferably at least 99% sequence identity to SEQ ID NO:11.

In one aspect the 5T4-specific CAR according to the invention comprises a "linker" domain having at least 70, 75, 80, 85, 90, 91, 92, 93, 94, 95, 96, 97, 98, 99 or 100% sequence identity to SEQ ID NO:4. In one aspect the linker domain has at least 95%, preferably at least 98% or more preferably at least 99% sequence identity to SEQ ID NO:4.

In one aspect the 5T4-specific CAR according to the invention comprises a "CD8 hinge" domain having at least 70, 75, 80, 85, 90, 91, 92, 93, 94, 95, 96, 97, 98, 99 or 100% sequence identity to SEQ ID NO:5. In one aspect the CD8 hinge domain has at least 95%, preferably at least 98% or more preferably at least 99% sequence identity to SEQ ID NO:5.

In one aspect the 5T4-specific CAR according to the invention comprises a "CD8 transmembrane" domain having at least 70, 75, 80, 85, 90, 91, 92, 93, 94, 95, 96, 97, 98, 99 or 100% sequence identity to SEQ ID NO:6. In one aspect the CD8 transmembrane domain has at least 95%, preferably at least 98% or more preferably at least 99% sequence identity to SEQ ID NO:6.

In one aspect the 5T4-specific CAR according to the invention comprises a "41BB costimulatory" domain having at least 70, 75, 80, 85, 90, 91, 92, 93, 94, 95, 96, 97, 98, 99 or 100% sequence identity to SEQ ID NO:7. In one aspect the 41BB costimulatory domain has at least 95%, preferably at least 98% or more preferably at least 99% sequence identity to SEQ ID NO:7.

In one aspect the 5T4-specific CAR according to the invention comprises a "CD3 zeta stimulatory" domain having at least 70, 75, 80, 85, 90, 91, 92, 93, 94, 95, 96, 97, 98, 99 or 100% sequence identity to SEQ ID NO:8. In one aspect the CD3 zeta stimulatory domain has at least 95%, preferably at least 98% or more preferably at least 99% sequence identity to SEQ ID NO:8.

In one aspect the invention provides a 5T4-specific CAR which has the sequence set out in SEQ ID NO:1, or a sequence with at least 92% identity to SEQ ID NO:1.

```
SEQ ID NO: 1:
MGVLLTQRTLLSLVLALLFPSMASMEVQLQQSGPDLVKPGASVKISCKAS

GYSFTGYYMHWVKQSHGKSLEWIGRINPNNGVTLYNQKFKDKAILTVDKS

STTAYMELRSLTSEDSAVYYCARSTMITNYVMDYWGQVTSVTVSSGGGGS

GGGGTGGGGSSIVMTQTPTFLLVSAGDRVTITCKASQSVSNDVAWYQQKP

GQSPTLLISYTSSRYAGVPDRFIGSGYGTDFTFTISTLQAEDLAVYFCQQ

DYNSPPTFGGGTKLEIKRAAALSNSIMYFSHFVPVFLPAKPTTTPAPRPP

TPAPTIASQPLSLRPEACRPAAGGAVHTRGLDFACDIYIWAPLAGTCGVL

LLSLVITLYCKRGRKKLLYIFKQPFMRPVQTTQEEDGCSCRFPEEEEGGC
```

-continued

ELLRVKFSRSADAPAYQQGQNQLYNELNLGRREEYDVLDKRRGRDPEMGG

KPRRKNPQEGLYNELQKDKMAEAYSEIGMKGERRRGKGHDGLYQGLSTAT

KDTYDALHMQALPPR

In one aspect the CAR has the sequence of SEQ ID NO:1.

In one aspect the CAR has a sequence which is at least 92, 93, 94, 95, 96, 97, 98 or 99% identical to SEQ ID NO:1.

In one aspect the invention provides a 5T4-specific CAR which has the sequence set out in SEQ ID NO:13, or a sequence with at least 70% identity to SEQ ID NO:13.

SEQ ID NO: 13:
MGVLLTQRTLLSLVLALLFPSMASMEVQLQQSGPELVKPGASVKISCKAS

GYSFTGYYMHWVKQSHVKSLEWIGRINPYNGATTYNQDFKDKASLTVDKS

SSTASMELHSLTSEDSAVYYCALSTMITTAWFAYWGQGTLVTVSPGGGGS

GGGGTGGGGSNFVMTQTPKFLLASAGDRVTISCKASQSVSNDVGWYQQKP

GQSPKLLIYFASNRYTGVPDRFIGSGYGTDFTFTISTVQAEDLAVYFCQQ

DYSSPFTFGSGTKLEIKAAALSNSIMYFSHFVPVFLPAKPTTTPAPRPPT

PAPTIASQPLSLRPEACRPAAGGAVHTRGLDFACDIYIWAPLAGTCGVLL

LSLVITLYCKRGRKKLLYIFKQPFMRPVQTTQEEDGCSCRFPEEEEGGCE

LLRVKFSRSADAPAYQQGQNQLYNELNLGRREEYDVLDKRRGRDPEMGGK

PRRKNPQEGLYNELQKDKMAEAYSEIGMKGERRRGKGHDGLYQGLSTATK

DTYDALHMQALPPR

In one aspect the CAR has the sequence of SEQ ID NO:13.

In one aspect the CAR has a sequence which is at least 70, 71, 72, 73, 74 75, 76, 77, 78, 79, 80, 81, 82, 83, 84, 85, 86, 87, 88, 89, 90, 91, 92, 93, 94, 95, 96, 97, 98 or 99% identical to SEQ ID NO:13.

Sequence identity may be assessed by any convenient method. However, for determining the degree of sequence identity between sequences, computer programs that make multiple alignments of sequences are useful, for instance Clustal W (Thompson et al., (1994) Nucleic Acids Res., 22: 4673-4680). Programs that compare and align pairs of sequences, like ALIGN (Myers et al., (1988) CABIOS, 4: 1-17), FASTA (Pearson et al., (1988) PNAS, 85:2444-2448; Pearson (1990), Methods Enzymol., 183: 63-98) and gapped BLAST (Altschul et al., (1997) Nucleic Acids Res., 25: 3389-3402) are also useful for this purpose.

Furthermore, the Dali server at the European Bioinformatics institute offers structure-based alignments of protein sequences (Holm (1993) J. Mol. Biol., 233: 123-38; Holm (1995) Trends Biochem. Sci., 20: 478-480; Holm (1998) Nucleic Acid Res., 26: 316-9).

Multiple sequence alignments and percent identity calculations may be determined using the standard BLAST parameters, (using sequences from all organisms available, matrix Blosum 62, gap costs: existence 11, extension 1).

Alternatively, the following program and parameters may be used: Program: Align Plus 4, version 4.10 (Sci Ed Central Clone Manager Professional Suite). DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

Thus included in the scope of the invention are variants of the stated or given sequences, as long as the variant retains the functional activity of the parent i.e. the variants are functionally equivalent, in other words they have or exhibit an activity of the parent, for example in the context of a CAR structure. Such variants may comprise amino acid substitutions, additions or deletions of one or more amino acid compared to the parent sequence.

By a "variant" of the given amino acid sequence is intended to mean that the side chains of, for example, one or two of the amino acid residues may be altered (for example by replacing them with the side chain of another naturally occurring amino acid residue or some other side chain) such that the peptide retains the functional activity of the parent peptide from which it is derived.

Variants may involve the replacement of an amino acid residue by one or more of those selected from the residues of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

Such variants may arise from homologous substitution i.e. like-for-like/conservative substitution such as basic for basic, acidic for acidic, polar for polar etc. Non-homologous substitution may also occur i.e. from one class of residue to another or alternatively involving the inclusion of unnatural amino acids such as ornithine, diaminobutyric acid, norleucine, pyridylalanine, thienylalanine, naphthylalanine and phenylglycine.

A substitution may be a conservative substitution. As used herein, a "conservative substitution" refers to changing amino acid identity at a given position to replace with an amino acid of approximately equivalent size, charge and/or polarity. Examples of natural conservative substitutions of amino acids include the following 8 substitution groups (designated by the conventional one-letter code): (1) M, I, L, V; (2) F, Y, W; (3) K, R, (4) A, G; (5) S, T; (6) Q, N; (7) E, D; and (8) C, S. Also included are functionally-equivalent derivatives in which one or more of the amino acids are chemically derivatised, e.g. substituted with a chemical group. Functionally-equivalent derivatives may be modified chemically by reacting specific amino acids either before or after synthesis of the peptide. Examples are known in the art e.g. as described in R. Lundblad, Chemical Reagents for Protein Modification, 3rd ed. CRC Press, 2004 (Lundblad, 2004. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto.

Nucleic Acids and Vectors

The invention also encompasses a nucleic acid molecule having a nucleotide sequence which encodes the amino acid sequence of SEQ ID NO:1 or a sequence with at least 92% identity to SEQ ID NO:1. The nucleic acid molecule may encode an amino acid sequence having 92, 93, 94, 95, 96, 97, 98, 99 or 100% sequence identity to SEQ ID NO:1. In one aspect the nucleic acid molecule encodes an amino acid sequence which consists of the sequence of SEQ ID NO:1.

In one aspect the nucleic acid molecule has a sequence which encodes the amino acid sequence of any of SEQ ID NOs: 2, 3, 4, 5, 6, 7 and/or 8, and/or a sequence or sequences with at least 70, 75, 80, 85, 90, 91, 92, 93, 94, 95, 96, 97, 98, 99 or 100% sequence identity thereto. In one aspect the level of sequence identity is at least 95% or preferably 98%.

In one aspect the nucleic acid molecule has a sequence which encodes the amino acid sequence of SEQ ID NOs: 2, 3, 4, 5, 6, 7 and 8.

A "nucleic acid molecule", as referred to herein, may be DNA or RNA, naturally-occurring or synthetic, or any combination thereof. Nucleic acids encoding a 5T4-specific CAR may be constructed in such a way that it may be translated by the machinery of the cells of a host organism. Thus, natural nucleic acids may be modified, for example to increase the stability thereof. DNA and/or RNA, but especially RNA, may be modified in order to improve nuclease resistance.

For example, known modifications for ribonucleotides include 2'-O-methyl, 2'-fluoro, 2'-NH$_2$, and 2'-O-allyl. Modified nucleic acids may comprise chemical modifications which have been made in order to increase the in vivo stability of the nucleic acid, enhance or mediate the delivery thereof, or reduce the clearance rate from the body. Examples of such modifications include chemical substitutions at the ribose and/or phosphate and/or base positions of a given RNA sequence. See, for example, WO 92/03568; U.S. Pat. No. 5,118,672; Hobbs et al., (1973) Biochemistry 12:5138; Guschlbauer et al., (1977) Nucleic Acids Res. 4:1933; Schibaharu et al., (1987) Nucleic Acids Res. 15:4403; Pieken et al., (1991) Science 253:314.

The invention also encompasses nucleic acid molecules that hybridise to a nucleic acid molecule as described herein, for example having a nucleotide sequence which encodes the amino acid sequence of SEQ ID NO:1 or a sequence with at least 92% identity to SEQ ID NO:1 under high, moderate or low stringency conditions. In one aspect the conditions are high stringency conditions.

Stringency of hybridisation refers to conditions under which polynucleic acid hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65-68° C. High stringency conditions can be provided, for example, by hybridisation in an aqueous solution containing 6×SSC, 5×Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2-0.1×SSC, 0.1% SDS.

Moderate stringency refers to conditions equivalent to hybridisation in the above described solution but at about 60-62° C. In that case the final wash is performed at the hybridisation temperature in 1×SSC, 0.1% SDS.

Low stringency refers to conditions equivalent to hybridisation in the above described solution at about 50-52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

The invention also encompasses a vector comprising a nucleic acid molecule having a nucleotide sequence which encodes the amino acid sequence of SEQ ID NO:1 or a sequence with at least 92% identity to SEQ ID NO:1. In one aspect the nucleic acid molecule has the sequence as set out in SEQ ID NO:9.

The nucleic acid molecule may be operably linked to a promoter. In one aspect the EF1α promoter is utilized (see SEQ ID NO:10).

The nucleic acid may be in an expression cassette or expression vector (e.g. a plasmid for introduction into a bacterial host cell, or a viral vector, or a plasmid or viral vector such as a lentivirus for transfection of a mammalian host cell). Suitable lentiviral vectors may be derived from HIV-1, HIV-2, SIV, FIV, BIV, EIAV, CAEV or visna lentivirus and are described in U.S. Pat. Nos. 6,924,123, 7,056, 699, WO1998/055607, WO 1998/17815, WO 1999/32646, WO 2001/79518, WO 2003/064665, U.S. Pat. No. 6,969, 598.

As used herein, a "vector" may be any agent capable of delivering or maintaining nucleic acid in a host cell, and includes viral vectors, plasmids, naked nucleic acids, nucleic acids complexed with polypeptide or other molecules and nucleic acids immobilised onto solid phase particles.

As discussed herein, the invention encompasses a method for providing immune cells for immunotherapy comprising introducing ex-vivo into said immune cells nucleic acid molecules or vectors of the invention.

In one aspect, said nucleic acid molecule is included in a lentiviral vector. In a further aspect the lentiviral vector is derived from HIV or EIAV.

Cancer Treatment or Prevention

The 5T4-specific CAR of the present invention may be used in therapy i.e. as a medicament.

In particular, the 5T4-specific CAR of the present invention may be used in the treatment or prevention of cancer.

The invention provides a method for the treatment or prevention of cancer in a subject comprising administering a 5T4-specific CAR of the invention to the subject.

Also provided is use of the 5T4-specific CAR of the invention in the manufacture of a medicament for use in the treatment or prevention of cancer, and use of the 5T4-specific CAR in the treatment or prevention of cancer.

The 5T4-specific CAR of the invention may be used in in the treatment or prevention of cancers that express the 5T4 antigen.

For example, such cancers may include, but are not limited to, cancers involving solid tumours such as bile duct, bone, bladder, brain/CNS, breast, colorectal, cervical, endometrial, gastric, head and neck, hepatic, lung, muscle, mesothelioma, neuronal, oesophageal, ovarian, pancreatic, pleural/peritoneal membranes, prostate, renal, skin, testicular, thyroid, placental, uterine and vulval tumours.

In one aspect the cancer does not involve a solid tumour, and is a haematological cancer as described herein.

In one aspect the cancer is ovarian cancer.

In one aspect the cancer is mesothelioma.

In one aspect the cancer is myeloma.

In one aspect the cancer is chronic lymphocytic leukaemia, acute myeloid leukaemia, multiple myeloma B cell acute lymphoblastic leukaemia, chronic myeloid leukaemia or T cell acute lymphoblastic leukaemia.

In one aspect the cancer is pre-B acute lymphoblastic leukaemia, for example childhood pre-B acute lymphoblastic leukaemia.

Immune Cells

Provided are cells, such as engineered immune or immuno stimulatory cells, as well as methods for producing and using the cells, such as in adoptive therapy, and compositions, such as pharmaceutical compositions, containing the cells.

The present invention thus provides an immune cell expressing a 5T4-specific CAR as described herein. A population of such cells is also provided.

In one aspect the invention provides a method for providing an immune cell, such as a T cell, NK cell or NKT cell, comprising introducing into a cell ex vivo a nucleic acid or vector as defined herein.

In one aspect the cell or population of cells may be used in therapy, i.e. as a medicament.

The cell or population of cells may be used for treating or preventing cancer.

In one aspect the cancer is myeloma.

In one aspect the cell may be genetically modified to render it more suitable for allogeneic transplantation.

The cell may be made allogeneic, for instance, by inactivating at least one gene expressing one or more component of a T-cell receptor (TCR) as described in WO 2013/176915, which may be combined with the inactivation of a gene encoding or regulating HLA or β2m protein expression. The risk of graft versus host syndrome and graft rejection may be reduced.

The immune cell may be further genetically engineered to improve resistance to immunosuppressive drugs or chemotherapy treatments, for example which are used as standard care for treating 5T4 positive malignant cells. For instance, CD52 and glucocorticoid receptors (G), which are drug targets of Campath (alemtuzumab) and glucocorticoids treatments, can be inactivated to make the cells resistant to these treatments and give them a competitive advantage over endogenous T-cells not endowed with specific 5T4 CARs. Expression of CD3 gene can also be suppressed or reduced to confer resistance to Teplizumab, another immune suppressive drug. Expression of HPRT can also be suppressed or reduced to confer resistance to 6-thioguanine, a cytostatic agent commonly used in chemotherapy.

Genes encoding proteins that act as "immune checkpoints" that act as regulators of T-cell activation, such as PDCD1 or CTLA-4, may also be inactivated.

In one aspect, the cell may comprise another genetically engineered antigen receptor, such as a costimulatory receptor, such as a chimeric costimulatory receptor, that specifically binds to another antigen and is capable of inducing a costimulatory signal to the cell. In some aspects, such another target antigen and the first target antigen recognized by the first receptor are distinct.

Administration

The cell or population of cells according to the invention may be administered in the form of a composition such as a pharmaceutical composition, which may comprise the cell or population of cells and one or more pharmaceutically acceptable excipient.

The administration of a cell or population of cells or composition may be by any suitable means, for example injection ingestion implantation, transplantation or inhalation or transfusion.

Administration may be by any suitable route, for example local or systemic administration.

In one aspect administration may be intravenous, intraperitoneal, subcutaneous, intradermal, intratumoural or intramuscular.

In one aspect administration is local administration, for example intraperitoneal or intrapleural administration. In one aspect the cancer is ovarian cancer or mesothelioma and administration is intraperitoneal (ovarian) or intrapleural (mesothelioma).

In one aspect administration is systemic, and the cancer is myeloma.

The number of cells to be administered may be in the range of $1 \times 10^5$ to $1 \times 10^{10}$ cells/kg body weight. In some aspects the number of cells to be administered is about $1 \times 10^6$-$2 \times 10^7$ cells per kg body weight. In some aspects the number of cells to be administered is in the range of $1 \times 10^7$-$1 \times 10^{11}$ cells. The cells may administered once or multiple times within the ranges described above and by using infusion techniques that are commonly known in immunotherapy (see, e.g. Rosenberg et al 1998 New Eng. J. Med. 319; 1676). In certain aspects the cells may be administered via the intraperitoneal or intrapleural route. In one aspect the cancer is ovarian cancer or mesothelioma.

In certain aspects it may be desired to administer cells (such as T cells, NK cells or NK-T cells) to a subject and then subsequently re-draw blood (or perform apheresis), activate the cells and re-infuse the activated and/or expanded cells to the subject.

The number of cells to be administered to a patient will vary depending on the precise nature of the condition being treated and the status of the patient. The scaling of doses for administration to patients can be performed according to accepted methods described in the art.

In certain aspects lymphodepletion is performed on a subject e.g. prior to the administration of cells (such as T cells, NK cells or NKT cells) that express for example a CAR or a TCR. Lymphodepletion comprises administering one or more of melphalan, Cytoxan, cyclophosphamide, and fludarabine or similar agents known to the skilled person to be suitable for lymphodepletion.

Combination Therapies

The 5T4-targeting agent, for example 5T4-specific CAR T cell, according to the invention may be used as a monotherapy or in combination with, for example, standard of care for treatment of cancers, e.g. a haematological cancer.

'In combination' may refer to administration of the additional therapy before, at the same time as or after administration of any aspect according to the present invention.

Accordingly, methods for the treatment of cancer include administering to a patient in need thereof an effective amount of a 5T4-targeting agent, such as the 5T4-specific CAR T cell of the invention, as a monotherapy or in combination with an additional anti-cancer agent or other agent to alleviate symptoms of the cancer.

For example, the 5T4-targeting agent may be administered in combination with checkpoint blockade therapy, co-stimulatory antibodies, chemotherapy and/or radiotherapy, targeted therapy or monoclonal antibody therapy.

In one aspect the 5T4-targeting agent may be administered in combination with an inhibitor of an immune checkpoint protein. Examples of inhibitory immune checkpoint proteins include but are not limited to PD-1, CTLA-4, BTLA, KIR, LAG3, TIGIT, CD155, B7H3, B7H4, VISTA and TIM3. Examples of activatory immune checkpoint proteins include but are not limited to GITR, OX40, 4-1BB, ICOS, HVEM. Immune checkpoint proteins may also refer to proteins which bind to other immune checkpoint proteins which modulate the immune response in an inhibitory or activatory manner. Such proteins include but are not limited to PD-L1, PD-L2, CD80, CD86, HVEM, GAL9, ICOS-Ligand, OX-40 Ligand, GITR-Ligand, 4-1BB-Ligand.

In one aspect the 5T4-targeting agent may be administered in combination with cytokine therapy. Cytokine therapies include but are not limited to IFN-α, IL-2, IFN-γ, IL-1, IL-3, GM-CSF/IL-3 fusion protein, IL-4, -5, -7, -10, -12, -18, -21, and TNF-α therapies.

A chemotherapeutic entity as used herein refers to an entity which is destructive to a cell, that is the entity reduces the viability of the cell. The chemotherapeutic entity may be a cytotoxic drug. A chemotherapeutic agent contemplated includes, without limitation, alkylating agents, anthracyclines, epothilones, nitrosoureas, ethylenimines/methylmelamine, alkyl sulfonates, alkylating agents, antimetabolites, pyrimidine analogs, epipodophylotoxins, enzymes such as L-asparaginase; biological response modifiers such as IFNα, IL-2, G-CSF and GM-CSF; platinum coordination complexes such as cisplatin, oxaliplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

By way of non-limiting example, in one aspect the 5T4-targeting agent may be administered in combination with carfilzomib (e.g. KYPROLIS®), a proteasome inhibitor used to treat multiple myeloma (see Siegel D S et al. Blood 2012; 120:2817-2825). Carfilzomib can be administered as an intravenous/IV infusion. Carfilzomib has been combined with various additional agents to treat multiple myeloma. For example, carfilzomib has been combined with lenalidomide and/or dexamethasone and/or pomalidomide. In one aspect, carfilzomib may be administered in a combination therapy with lenalidomide or pomalidomide, dexamethasone, and a 5T4-targeting agent.

Carfilzomib has also been combined with panobinostat (see Berdeja J G et al. Haematologica 2015; 100:670-676). In one aspect, carfilzomib is administered in a combination therapy with panobinostat and 5T4-targeting agent.

Another exemplary agent for combination therapy is daratumumab (e.g. DARZALEX™), a human monoclonal antibody that binds CD38 (a glycoprotein highly expressed on multiple myeloma cells). Daratumumab can be administered to patients by intravenous infusion to treat multiple myeloma (see Lokhorst H M et al. N Engl J Med 2015; 373:1207-1219).

In one aspect the 5T4-targeting agent may be combined with elotuzumab (e.g.EMPLICITI™), a monoclonal antibody that binds CD319, or signaling lymphocytic activation molecule F7 (SLAMF7), a marker for malignant multiple myeloma cells. Elotuzumab can be administered to patients by intravenous infusion to treat multiple myeloma (see Zonder J A et al. Blood 2012; 120: 552-559).

Alternatively, the combination therapy may involve lenalidomide (e.g.REVLIMID®), an immunomodulatory agent given to patients to treat multiple myeloma.

Another exemplary agent for combination therapy is bortezomib (e.g. VELCADE®), a proteasome inhibitor given to patients to treat multiple myeloma and mantle cell lymphoma (see Richardson P G et al. N Engl J Med 2003; 348:2609-2617). Bortezomib can be administered to patients via intravenous injection.

Another exemplary agent for combination therapy is cyclophosphamide (e.g. CYTOXAN®), an alkylating agent used to treat cancer (including multiple myeloma, acute myelocytic leukaemia, Hodgkin's and non-Hodgkin's lymphoma, breast cancer, and lung cancer, among others).

Melphalan, an alkylating agent, may also be used in a combination therapy treat cancer (including multiple myeloma and ovarian cancer). Melphalan can be administered orally, as an injection or infusion.

Other exemplary agents for combination therapy include pomalidomide (e.g.POMALYST®), an immunomodulatory agent used to treat multiple myeloma, and ixazomib (NINLARO®), a proteasome inhibitor used to treat cancer (including multiple myeloma).

Drug Conjugates

As discussed herein, in a further aspect, the 5T4-targeting agent according to the invention may itself act as a carrier to selectively deliver, for example, a toxic molecule to cancer cells, e.g. haematological cancer cells. That is, the specificity of, for example, an antibody/CAR can achieve selective delivery of the toxic payload to cells expressing 5T4.

By way of example, specificity of a 5T4-specific antibody or CAR/CAR T cell may be exploited to deliver a linked cytotoxic agent to a cancer cell, such as a haematological cell.

In one aspect, an antibody-drug conjugate or CAR T cell-drug conjugate may be used.

Suitable conjugates and methods for conjugation are known in the art—see for example the review in Parslow et al. Biomedicines 2016, 4:14.

The invention will now be further described by way of Examples, which are meant to serve to assist one of ordinary skill in the art in carrying out the invention and are not intended in any way to limit the scope of the invention.

EXAMPLES

Example 1. Production of 2E4 Antibodies and Designing 5T4 CAR Constructs

Production of 2E4 Antibodies

A recombinant protein comprising the extracellular domain of 5T4 with a C-terminal enterokinase cleavage sequence, myc epitope and a six histidine tag, purified from CHO cells using column chromatography (nickel beads) was used as the immunogen. The Immuno-Precise (Canada) rapid prime protocol was employed (immunisation of 3 mice followed by 4 rapid boosts) to make mAbs in mice.

Donor spleen cells were fused with SP2/0 myeloma IgG hybridomas. mAbs were screened against the recombinant protein and counter-screened against the extracellular domain of a different leucine rich protein carrying the same C-terminal tag by ELISA. 10 Supernatants were selected for further study.

All supernatants recognised recombinant human 5T4 by western blot, although in cell lysates additional bands were detected by some supernatants. Using strength of recognition of both reduced and unreduced 5T4 protein on western blot, four mAbs were chosen for protein G column purification. Sequencing and further analyses by western blot and ELISA demonstrated that each of the four mAbs is unique.

| mAb | Western | ELISA | Purified | Isotype | Sequence |
|-----|---------|-------|----------|---------|----------|
| 2E4 | ✓ | ✓ | ✓ | IgG1 | ✓ |
| 6F4 | ✓ | ✓ | ✓ | IgG1 | ✓ |
| 2B1 | ✓ | ✓ | ✓ | IgG1 | ✓ |
| 7G6 | ✓ | ✓ | ✓ | IgG1 | ✓ |

The 2E4 antibody was chosen for further study.

5T4 CAR Constructs

The EF1α-H8-4-1BB/CD3ζ 5T4 construct (pRKh-EF1α-H8-4-1BB) was generated as described in FIG. 1, panel B; a codon-optimised sequence encoding the 5T4-CAR protein (SEQ ID NO: 9) (comprised of the H8 scFv antigen binding domain, CD8 hinge and transmembrane domains, 4-1BB costimulatory domain, and the CD3ζ stimulatory domain) was generated by de novo DNA synthesis. The synthesised 5T4-CAR cassette was inserted into a HIV-1 GFP genome plasmid (pRKHVCG) to replace the GFP gene, and positioned the 5T4-CAR transgene downstream of an internal cytomegalovirus (CMV) promoter, to give rise to the pRKh5T4CD8 plasmid. Finally, the CMV promoter was substituted with the elongation factor 1α (EF1α) promoter to yield pRKh-EF1α-H8-4-1BB; the EF1α sequence (SEQ ID NO: 10) was derived from the pEF1α-coTRAP-Puro plasmid.

The pRKh-EF1α-H8-4-1BB plasmid was constructed via a set of molecular cloning experiments. Both pRKHVCG and pUC57-h5T4-CD8 (housing the sequence encoding the 5T4-CAR protein, flanked by two restriction sites corresponding to those also found in pRKHVCG) parental constructs were digested with two distinct restriction enzymes to yield complementary cohesive ends, to facilitate directional ligation. The pRKHVCG vector backbone and 5T4-CAR encoding-fragment were isolated by means of gel electrophoresis and subsequent gel purification. The former fragment was treated with an alkaline phosphatase step to preclude self-ligation. Both linear fragments were ligated with the aid of DNA ligase, and the resulting pRKh5T4CD8 construct propagated in the common DH5α E. coli strain. Substitution of the promoter sequence was achieved via a method akin to that described above.

-H8-CD8-4-1BB-CD3ζ (Codon-Optimised sequence)
SEQ ID NO: 9
ATGGGAGTGCTGCTGACCCAGAGAACCCTGCTGTCTCTGGTGCTGGCCCT

GCTGTTCCCTAGCATGGCCAGCATGGAAGTGCAGCTGCAGCAGAGCGGCC

CTGACCTCGTGAAACCTGGCGCCTCCGTGAAGATCAGCTGCAAGGCCAGC

GGCTACAGCTTCACCGGCTACTACATGCACTGGGTCAAGCAGAGCCACGG

CAAGAGCCTGGAATGGATCGGCCGGATCAACCCCAACAACGGCGTGACCC

TGTACAACCAGAAGTTCAAGGACAAGGCCATCCTGACCGTGGACAAGAGC

-continued
AGCACCACCGCCTACATGGAACTGCGCGAGCCTGACCAGCGAGGACAGCGC

CGTGTACTACTGCGCCCGGTCCACCATGATCACCAACTACGTGATGGACT

ACTGGGGCCAAGTGACCAGCGTGACCGTGTCTAGCGGAGGCGGAGGATCT

GGCGGCGGAGGAACAGGCGGAGGGGGATCTAGCATCGTGATGACCCAGAC

CCCCACCTTCCTGCTGGTGTCTGCCGGCGACAGAGTGACCATCACATGCA

AGGCCTCCCAGAGCGTGTCCAACGACGTGGCCTGGTATCAGCAGAAGCCT

GGCCAGAGCCCCACCCTGCTGATTAGCTACACCAGCTCCAGATATGCCGG

CGTGCCCGACAGATTCATCGGCAGCGGCTATGGCACCGACTTCACCTTCA

CCATCAGCACACTGCAGGCCGAGGACCTGGCTGTGTACTTCTGTCAGCAA

GACTACAACAGCCCCCCTACCTTCGGCGGAGGCACCAAGCTGGAAATCAA

GAGAGCCGCCGCTCTGAGCAACAGCATCATGTACTTCAGCCACTTCGTGC

CCGTGTTTCTGCCCGCCAAGCCTACCACAACCCCTGCCCCTAGACCTCCT

ACCCCAGCCCCTACAATCGCCAGCCAGCCTCTGTCTCTGAGGCCCGAGGC

TTGTAGACCTGCTGCTGGCGGAGCCGTGCACACCAGAGGACTGGATTTCG

CCTGCGACATCTACATCTGGGCCCCTCTGGCCGGCACATGTGGCGTGCTG

CTGCTGAGCCTCGTGATCACCCTGTACTGCAAGCGGGGCAGAAAGAAGCT

GCTGTACATCTTCAAGCAGCCCTTCATGCGGCCCGTGCAGACCACCCAGG

AAGAGGACGGCTGCTCCTGCAGATTCCCCGAGGAAGAAGAAGGCGGCTGC

GAGCTGCTGAGAGTGAAGTTCAGCAGATCCGCCGACGCCCCTGCCTACCA

GCAGGGACAGAATCAGCTGTACAACGAGCTGAACCTGGGCAGACGGGAAG

AGTACGACGTGCTGGACAAGCGGAGAGGCAGGGACCCTGAGATGGGCGGC

AAGCCCAGAAGAAAGAACCCCCAGGAAGGCCTGTATAACGAACTGCAGAA

AGACAAGATGGCCGAGGCCTACAGCGAGATCGGAATGAAGGGCGAGCGGA

GAAGAGGCAAGGGCCACGATGGACTGTACCAGGGCCTGAGCACCGCCACC

AAGGACACCTATGACGCCCTGCACATGCAGGCTCTGCCCCCCAGATGA

-EF1α promoter
SEQ ID NO: 10
GGCTCCGGTGCCCGTCAGTGGGCAGAGCGCACATCGCCCACAGTCCCCGA

GAAGTTGGGGGGAGGGGTCGGCAATTGAACCGGTGCCTAGAGAAGGTGGC

GCGGGGTAAACTGGGAAAGTGATGTCGTGTACTGGCTCCGCCTTTTTCCC

GAGGGTGGGGAGAACCGTATATAAGTGCAGTAGTCGCCGTGAACGTTCT

TTTTCGCAACGGGTTTGCCGCCAGAACACAGGTAAGTGCCGTGTGTGGTT

CCCGCGGGCCTGGCCTCTTTACGGGTTATGGCCCTTGCGTGCCTTGAATT

ACTTCCACCTGGCTGCAGTACGTGATTCTTGATCCCGAGCTTCGGGTTGG

AAGTGGGTGGGAGAGTTCGAGGCCTTGCGCTTAAGGAGCCCCTTCGCCTC

GTGCTTGAGTTGAGGCCTGGCCTGGGCGCTGGGGCCGCCGCGTGCGAATC

TGGTGGCACCTTCGCGCCTGTCTCGCTGCTTTCGATAAGTCTCTAGCCAT

TTAAAATTTTTGATGACCTGCTGCGACGCTTTTTTTCTGGCAAGATAGTC

TTGTAAATGCGGGCCAAGATCTGCACACTGGTATTTCGGTTTTTGGGGCC

GCGGGCGGCGACGGGCCCGTGCGTCCCAGCGCACATGTTCGGCGAGGCG

GGGCCTGCGAGCGCGGCCACCGAGAATCGGACGGGGGTAGTCTCAAGCTG

GCCGGCCTGCTCTGGTGCCTGGCCTCGCGCCGCCGTGTATCGCCCCGCCC

-continued
```
TGGGCGGCAAGGCTGGCCCGGTCGGCACCAGTTGCGTGAGCGGAAAGATG

GCCGCTTCCCGGCCCTGCTGCAGGGAGCTCAAAATGGAGGACGCGGCGCT

CGGGAGAGCGGGCGGGTGAGTCACCCACACAAAGGAAAAGGGCCTTTCCG

TCCTCAGCCGTCGCTTCATGTGACTCCACGGAGTACCGGGCGCCGTCCAG

GCACCTCGATTAGTTCTCGAGCTTTTGGAGTACGTCGTCTTTAGGTTGGG

GGGAGGGGTTTTATGCGATGGAGTTTCCCCACACTGAGTGGGTGGAGACT

GAAGTTAGGCCAGCTTGGCACTTGATGTAATTCTCCTTGGAATTTGCCCT

TTTTGAGTTTGGATCTTGGTTCATTCTCAAGCCTCAGACAGTGGTTCAAA

GTTTTTTTCTTCCATTTCAGGTGTCGTGA
```

The EF1α-2E4-4-1BB/CD3ζ 5T4 construct (pRKh-EF1α-2E4-4-1BB) was generated as described in FIG. 1, panel C; a sequence encoding the 2E4 antigen binding moiety (SEQ ID NO: 11) was synthesised and inserted into pRKh-EF1α-H8-4-1BB, replacing the H8 domain sequence.

-2E4 antigen binding moiety
SEQ ID NO: 14
```
ATGGAAGTGCAGCTGCAGCAGTCTGGCCCCGAGCTCGTGAAACCTGGCGC

CTCCGTGAAGATCAGCTGCAAGGCCAGCGGCTACAGCTTCACCGGCTACT

ACATGCACTGGGTCAAGCAGAGCCACGTGAAGTCCCTGGAATGGATCGGC

CGGATCAACCCCTACAACGGCGCCACCACCTACAACCAGGACTTCAAGGA

CAAGGCCTCCCTGACCGTGGACAAGAGCAGCAGCACCGCCAGCATGGAAC

TGCACAGCCTGACCAGCGAGGACAGCGCCGTGTACTACTGTGCCCTGAGC

ACCATGATCACCACCGCTTGGTTTGCCTACTGGGGCCAGGGCACACTCGT

GACCGTGTCTCCAGGAGGCGGAGGATCTGGCGGCGGAGGAACAGGCGGAG

GGGGATCTAACTTCGTGATGACCCAGACCCCCAAGTTCCTGCTGGCCTCT

GCCGGCGACAGAGTGACCATCAGCTGCAAGGCCAGCCAGAGCGTGTCCAA

CGACGTGGGCTGGTATCAGCAGAAGCCCGGCCAGAGCCCCAAGCTGCTGA

TCTACTTCGCCAGCAACCGGTACACCGGCGTGCCCGACAGATTCATCGGC

AGCGGCTACGGCACCGACTTCACCTTCACCATCAGCACCGTGCAGGCCGA

GGACCTGGCCGTGTACTTCTGTCAGCAAGACTACAGCAGCCCTTTCACCT

TCGGCTCCGGCACCAAGCTGGAAATCAAGG
```

Example 2. In Vitro Activity of CAR-5T4 T Cells—FIGS. 2-4

Tumour Cell Lines:

The tumour cell lines investigated were NCI-H226 (Mesothelioma, ATCC; Middlesex, UK), SKOV-3 (Ovarian adenocarcinoma, ATCC; Middlesex, UK), BT20 (Breast carcinoma, ATCC; Middlesex, UK), OVCAR-3 (Ovarian adenocarcinoma, ATCC; Middlesex, UK), LS174T (Colorectal adenocarcinoma, ATCC; Middlesex, UK), DLD-1 (Colorectal, ATCC; Middlesex, UK),) and NCI-H929 (Myeloma, ATCC; Middlesex, UK).

The media used to culture each cell line was as follows: NCI-H226 Media: RPMI 1640 (SIGMA, DORSET, UK), 1% Glutamine (SIGMA, DORSET, UK), 1% HEPES (Gibco; Paisley, UK), 1% Sodium Pyruvate (SIGMA, DORSET, UK) and 10% FBS (SeraLabs; West Sussex, UK). SKOV-3 Media: McCoys 5a Media (Life Technologies; Carlsbad Calif., US; Carlsbad Calif., US), 1% Glutamine (SIGMA, DORSET, UK), 10% FBS (SeraLabs; West Sussex, UK). BT20 Media: Eagles Minimum Essential Medium (SIGMA, DORSET, UK), 10% FBS (SeraLabs; West Sussex, UK), 1% glutamine (SIGMA, DORSET, UK). OVCAR-3 Media: RPMI 1640 (SIGMA, DORSET, UK), 1% Glutamine (SIGMA, DORSET, UK), 1% HEPES (Gibco; Paisley, UK), 1% Sodium Pyruvate (SIGMA, DORSET, UK), 1% Insulin (SIGMA, DORSET, UK) and 20% FBS (SeraLabs; West Sussex, UK) LS174T media: Eagles Minimum Essential Medium (SIGMA, DORSET, UK), 10% FBS (SeraLabs; West Sussex, UK), 1% glutamine (SIGMA, DORSET, UK). NCI-H929: RPM1640 (SIGMA, DORSET, UK), 10% FBS (SeraLabs; West Sussex, UK) and 1% Glutamine (SIGMA, DORSET, UK).

The cells were grown in T75 Flasks and passaged according to standard cell culture protocols until they reached >80% Confluency. The cells were cultured in an incubator (Panasonic; Loughborough, UK) at 37° C. and 5% CO2. The NCI-H226, SKOV-3 and NCI-H929 cells were passaged twice weekly at a 1:10 dilution. The BT20, OVCAR-3 and LS174T cells were passaged once a week also at a 1:10 dilution. Adherent cell lines were washed in PBS (SIGMA, DORSET, UK) and dissociated from the flask using TrypLE Express™ (GIBCO; Paisley, UK) at 37° C. for 5 minutes, neutralize with an equal volume of media, centrifuged and resuspended in an appropriate volume of media for further cell culture or for use in cytokine release assays or WST-1 assays or PBS for flow cytometry. Non-adherent cell lines (NCI-H929) were removed from culture, centrifuged and resuspended in media before use in further cell culture or PBS for flow cytometry. Cells were stored on ice, except for immediate routine tissue culture.

For this routine culture the cells were added in a 1:10 dilution to media to make a total volume of 25 ml in T75 flasks. Cells that were used in cytokine release assays and WST-1 assays were handled on ice, counted using the Guava PCA (Millipore; Watford, UK), pelleted and resuspended in media at a concentration of 1×10$^5$ cells/ml and 1×10$^4$ cells/ml, respectively.

PBMCs and T Cell Activation:

PBMCs were purchased from CTL (Bonn, Germany), or previously generated from blood purchased from Covance (Maidenhead, UK). T cells were activated from vials of PBMCs, cultured in T cell media consisting of: X-Vivo 15 (Sartorius; Surrey, UK), Human AB Serum (Akron Biotech; Florida, US), GlutaMax (Life Technologies; Carlsbad Calif., US), HEPES (Gibco; Paisley, UK; Paisley, UK), N-Acetylcysteine (APP Pharmaceuticals; Illinois, US), Sodium Pyruvate (SIGMA, DORSET, UK), MEM Eagle Vitamin mix (Lonza; Slough, UK) and rhiL-2 (R&D Systems; Abingdon, UK). Briefly, a vial of frozen PBMCs was revived by gently thawing in a water bath set to 37° C. and cells were added slowly to pre-warmed media. An aliquot of cells was counted using the Guava PCA. The cells were spun down and resuspended in a volume of media to give 5×10$^5$ cells/ml. The T cells were activated using CD3/CD8 expansion beads (GIBCO; Paisley, UK) at a bead to cell ratio of 3:1. The beads were washed and resuspended in PBS before 4×10$^6$ cells and 1.2×10$^7$ beads and 500 µl media were added to a 24-well plate.

T Cell Transduction/Generation of CAR T Cells

PBMCs were prepared for T cell activation as described above. The cells were then transduced twice; on consecutive days (Day 0, immediately following activation and Day 1) by the addition of 250 µl appropriately diluted vector;

CAR-T 5T4 constructs (H8 and 2E4). The cells were transduced with vectors at a Multiplicity of Infection (MOI) of 1, 0.33 and 0.11 representing the ratio of viral particles to susceptible cells. As a negative control, PBMCs were activated but no vector was added. Following transduction the cells were maintained in MM+IL-2 at a concentration of $5\times10^5$. To maintain the cells, the wells were thoroughly resuspended by gentle pipetting and an aliquot was removed for counting on Days 3, 6, 9, 10 and 14 using the Guava PCA. MM+IL2 was added to the cells to maintain them at a concentration of $5\times10^5$ cells/ml, transferring expanding cultures to T25 and T75 flasks as required. On Day 10, the media was not supplemented with IL-2. Cells were cultured until Day 14, when they assessed for functionality by cytokine release and cell killing (WST-1) assays.

Cytokine Release Assay

The Cytokine Release assays were performed according to the manufacturer's instructions. Test sample (7 μl) was added to 43 μl of buffer. CBA analysis was performed using a CBA Flex Set (BD Biosciences; Oxford, UK) according to the protocol. The data were analysed on the FCAP Array software (BD Biosciences; Oxford, UK).

WST-1/Cell Killing Assay

Target cells (NCI-H226 or LS174T) were added to each well ($1\times10^4$ of a flat bottomed 96-well plate. T cells were added at E:T ratios of 0.5:1, 1:1, 10:1 and 30:1. Target cells only and T cells only controls were also prepared. Cells were incubated in a 5% $CO_2$ atmosphere at 37° C. for 18-24 hours.

The following day, 50 μl WST-1 reagent was diluted 1:10 PBS and was added to the cells and the plates were read every hour using an absorbance plate reader at 440 nm with 630 nm reference wavelength. Percentage of cell killing was calculated by:

$$([\text{Experimental O.D})-(\text{Control O.D.})]/([\text{Maximal O.D.})-(\text{Control O.D.}])\times100$$

Example 3. Specificity of CAR-5T4 T Cells—FIG. 5

The specificity of the 5T4 CAR constructs was determined by blocking experiments in which a 5T4-specific monoclonal antibody (Panel A) or soluble 5T4 protein (Panel B) was incubated with tumour cell lines and CAR-5T4 T cells. Both blocking agents were titrated and the impact on IFNγ secretion assessed.

Tumour Cell Lines

The tumour cell lines investigated were NCI-H226 (Mesothelioma, ATCC; Middlesex, UK), and LS174T (Colorectal adenocarcinoma, ATCC; Middlesex, UK). The media used to culture NCI-H226 cells was: RPMI 1640 (SIGMA, DORSET, UK), 1% Glutamine (SIGMA, DORSET, UK), 1% HEPES (Gibco; Paisley, UK), 1% Sodium Pyruvate (SIGMA, DORSET, UK) and 10% FBS (SeraLabs; West Sussex, UK). The media used to culture LS174T cells was: Eagles Minimum Essential Medium (SIGMA, DORSET, UK), 10% FBS (SeraLabs; West Sussex, UK), 1% glutamine (SIGMA, DORSET, UK). NCI-H929: RPM11640 (SIGMA, DORSET, UK), 10% FBS (SeraLabs; West Sussex, UK) and 1% Glutamine (SIGMA, DORSET, UK).

The cells were grown in T75 Flasks and passaged according to standard cell culture protocols until they reached >80% Confluency. The cells were cultured in an incubator (Panasonic; Loughborough, UK) at 37° C. and 5% $CO_2$. The adherent cell lines were washed in PBS (SIGMA, DORSET, UK) and dissociated from the flask using TrypLE Express™ (GIBCO; Paisley, UK) at 37° C. for 5 minutes, neutralize with an equal volume of media, centrifuged and resuspended in an appropriate volume of media for further cell culture or for use in cytokine release assays or WST-1 (cell killing) assays or PBS for flow cytometry.

PBMCs and T Cell Activation:

PBMCs were purchased from CTL (Bonn, Germany), or previously generated from blood purchased from Covance (Maidenhead, UK). T cells were activated from vials of PBMCs, cultured in T cell media consisting of: X-Vivo 15 (Sartorius; Surrey, UK), Human AB Serum (Akron Biotech; Florida, US), GlutaMax (Life Technologies; Carlsbad Calif., US), HEPES (Gibco; Paisley, UK; Paisley, UK), N-Acetyl-cysteine (APP Pharmaceuticals; Illinois, US), Sodium Pyruvate (SIGMA, DORSET, UK), MEM Eagle Vitamin mix (Lonza; Slough, UK) and rhIL-2 (R&D Systems; Abingdon, UK). Briefly, a vial of frozen PBMCs was revived by gently thawing in a water bath set to 37° C. and cells were added slowly to pre-warmed media. An aliquot of cells was counted using the Guava PCA. The cells were spun down and resuspended in a volume of media to give $5\times10^5$ cells/ml. The T cells were activated using CD3/CD8 expansion beads (GIBCO; Paisley, UK) at a bead to cell ratio of 3:1. The beads were washed and resuspended in PBS before $4\times10^6$ cells and $1.2\times10^7$ beads and 500 μl media were added to a 24-well plate.

T Cell Transduction/Generation of CAR T Cells

PBMCs were prepared for T cell activation as described above. The cells were then transduced twice; on consecutive days (Day 0, immediately following activation and Day 1) by the addition of 250 μl appropriately diluted vector; CAR-T 5T4 constructs (H8 and 2E4). The cells were transduced with vectors at a Multiplicity of Infection (MOI) of 1, 0.33 and 0.11 representing the ratio of viral particles to susceptible cells. As a negative control, PBMCs were activated but no vector was added. Following transduction the cells were maintained in MM+IL-2 at a concentration of $5\times10^5$. To maintain the cells, the wells were thoroughly resuspended by gentle pipetting and an aliquot was removed for counting on Days 3, 6, 9, 10 and 14 using the Guava PCA. MM+IL2 was added to the cells to maintain them at a concentration of $5\times10^5$ cells/ml, transferring expanding cultures to T25 and T75 flasks as required. On Day 10, the media was not supplemented with IL-2. Cells were cultured until Day 14, when they assessed for functionality by cytokine release and cell killing (WST-1) assays.

Cytokine Release Assays:

No Blocking

T cells and target cells were set up as for the WST-1 cell killing assay. Prior to the addition of WST-1, an aliquot of the supernatant (50 μL) was removed, transferred to another plate and stored at −20° C. prior to analysis by Cytokine Release Assay.

Blocking with 5T4 Protein T cells were incubated with serially diluted recombinant 5T4 protein before being incubated for 1 hour. T Cells were added to tumour cells at an E:T ratio of 1:1 ($1\times10^5$ cells) in a round bottom 96-well plate and incubated for 18-24 hours at 37° C. in a 5% $CO_2$ atmosphere before the supernatants were removed and transferred to another plate and stored at −20° C. prior to analysis by Cytokine Release Assay.

Blocking with the 5T4-Specific Monoclonal Antibody 2E4

Tumour cells NCI-H226 and LS174T were incubated with serial dilutions (1:10) with a starting concentration of 200 μg/ml of anti-5T4 antibody 2E4 for 1 hour. T Cells were added to tumour cells incubated with 2E4 antibody at an E:T ratio of 1:1 ($1\times10^5$ cells) in a round bottom 96-well plate and incubated for 18-24 hours at 37° C. in a 5% CO2 atmosphere before the supernatants were removed and transferred to another plate and stored at −20° C. prior to analysis by Cytokine Release Assay.

The Cytokine Release assays were performed according to the manufacturer's instructions. Test sample (7 µl) was added to 43 µl of buffer. CBA analysis was performed using a CBA Flex Set (BD Biosciences; Oxford, UK) according to the protocol. The data were analysed on the FCAP Array software (BD Biosciences; Oxford, UK).

Example 4. Transduction of T Cells from Cancer Patients and CAR-T Cell Functionality The following recombinant lentiviral vectors were used in this study:

| Test Article | Batch No. | Strength (DNA) Titre (TU*/ml) | RNA Titre (copies/ml) | Sterility | Mycoplasma | Endotoxin |
|---|---|---|---|---|---|---|
| EF1α-H8-CAR-CD3ζ/4-1BB | C/23/10/2015/H8-41BB | 1.8E+08 | 6.2E+11 | Pass | Negative | Pass |
| EF1α-2E4-CAR-CD3ζ/4-1BB | C/16/10/2015/2E4-41BB | 2.9E+08 | 1.3E+12 | Pass | Negative | Pass |

*TU = Transducing Units

The test article vector was suspended in TSSM formulation buffer containing 20 mM Tris, 100 mM NaCl, 10 mg/mL sucrose, 10 mg/mL mannitol, pH 7.3. The TSSM buffer was supplied by Oxford BioMedica (UK) Ltd and was stored frozen.

The study was split into 4 parts:
1. Collection of matched tumour and peripheral blood mononuclear cells from approximately 15 patients with ovarian cancer
2. Assessment of 5T4 expression on formalin fixed paraffin embedded (FFPE) ovarian tumour sections using immunohistochemistry
3. Assessment of 5T4 expression on disaggregated tumour cells using flow cytometry
4. Assessment of CAR-T cell functionality, when co-cultured with Ovarian cancer cells, measured by cytokine release (highlighted in FIG. 6).

Collection of Matched Tumour and Blood Samples

Solid tumour biopsies were collected from patients undergoing surgery for ovarian cancer at St Mary's Hospital, Manchester, UK. Samples were collected through the Central Manchester University Hospital NHS Foundation Trust Biobank with appropriate ethical approval (Ref: 14/NW/1260) and informed consent. Solid tumour biopsies were collected into a sterile universal containing MACS Tissue Storage Solution (Miltenyi Biotec, Germany) and either transported directly to the laboratory for processing or stored at 4° C. for up to 24 hours prior to processing. 20-30 ml of blood was collected into BD Vacutainer blood collection tube containing EDTA (BD Biosciences, Oxford, UK). Blood samples were stored at room temperature and processed within 24 hours of collection. Samples available for analysis are listed in Table 1.

TABLE 1

Matched Tumour and Blood Samples from Patients with Ovarian Cancer. The table lists the patient's from which tumour tissue and peripheral blood mononuclear cells are available for analysis. The table lists the sample ID, disease stage, type of surgical intervention, tumour histology and availability of formalin fixed paraffin embedded (FFPE) tumour tissue.

| Sample ID | Disease Stage | Primary or Interval Debulking Surgery (IDS) | Histology | FFPE tissue Available |
|---|---|---|---|---|
| MOC 33 | FIGO 3C | Primary | High grade serous ovarian cancer | Yes |
| MOC 35 | FIGO 3C | Primary | High grade serous ovarian cancer | Yes |
| MOC 36 | FIGO 4 | IDS | High grade serous ovarian cancer | Yes |
| MOC 37 | FIGO 4 | Primary | High grade serous ovarian cancer | Yes |
| MOC 45* | FIGO 3C | IDS | High grade serous ovarian cancer | Yes |
| MOC 46 | FIGO 4 | IDS | High grade serous ovarian cancer | Yes |
| MOC 48 | FIGO 3C | IDS | High grade serous ovarian cancer | Yes |
| MOC 52 | FIGO 3C | Primary | High grade serous ovarian cancer | Yes |
| MOC 53 | FIGO 3C | Recurrent | Clear cell carcinoma | Yes |
| MOC 54 | FIGO 3C | IDS | High grade serous ovarian cancer | Yes |
| MOC 55 | FIGO 3C | IDS | High grade serous ovarian cancer | Yes |
| MOC 57 | FIGO 3C | Primary | Low grade serous ovarian cancer | Yes |

[*This patient had high grade serous ovarian cancer and received neoadjuvant chemotherapy prior to surgery. She was known to have a mass on her liver which was thought to be a metastatic lesion pre-operatively. She had a very good response to chemotherapy and the only significant disease at the time of surgery was the biopsied liver lesion, which was subsequently shown to be a benign haemangioma of the liver.]

Assessment of 5T4 Expression in Desegregated Tumour Cells

Tumour Disaggregation

Ovarian tumour samples were dissociated into single-cell suspensions using a commercial mechanical/enzymatic degradation kit (GentleMACS, Miltenyi Biotec, Germany) according to the manufacturer's protocol. Briefly, tumour biopsies were cut into 2-4 mm$^3$ fragments using a sterile scalpel and transferred into a C-tube (Miltenyi Biotec, Germany) with RPMI-1640 (Lonza, Slough, UK) and the appropriate volumes of enzymes H, R and A (Human Tumour Dissociation Kit, Miltenyi Biotec, Germany). The C-tube was then placed upside down onto the GentleMACS dissociator and subjected to three 36-second mechanical dissociation programs (h_tumour-01, h_tumour-02 and h_tumour-03). This was interjected by two 30-minute incubations at 37° C. under continuous rotation using the MACSmix Tube Rotator (Miltenyi Biotec, Germany), performed after the first and second dissociations programs. Following disaggregation, the suspension was passed through a 100 μm strainer into a 50 ml Falcon with 20 ml of T-cell media, and centrifuged at 400G for 5 minutes. The supernatant was discarded and the remaining cell pellet was thoroughly resuspended and cells counted. Cells were then cryopreserved in 90% FCS/10% DMSO at a density of 1-2×10$^7$ cells/ml.

Flow Cytometry

Cells from the tumour disaggregation were resuspended in T cell media at a concentration of 1×10$^6$ cells/ml. 100 μl aliquots of the cell suspension (1×10$^5$ cells) were transferred into the appropriate number of wells on a 96-well U-bottom plate. Cells were washed once in FACS buffer and stained with EpCAM (PE, clone 9C4, Biolegend) and 5T4 (clone H8 and 2E4) antibodies at 1:100 in FACS buffer for 30 minutes at 4° C. in the dark. Following this, cells were washed once in FACS buffer and then resuspended in 200 μl of 1% para-formaldehyde (PFA) (Sigma-Aldrich, UK) in PBS. Fixed cells were transferred into FACS tubes. Analysis was performed on the LSR Fortessa (BD Biosciences, UK). Data was analysed using FlowJo v. 7.6.2 software (Tree Star Inc, Ashland, Oreg.). Compensation was performed manually with single stain controls.

FIG. 8 shows that the majority of tumour disaggregates tested contained a large percentage (>50%) of 5T4 positive cells. The graph also shows that staining of tumour disaggregates with either H8 or 2E4 5T4-specific monoclonal antibodies yields comparable results.

4.3. T-Cell Transduction and CAR-T Functionality

Dose Preparation

The vector was supplied pre-formulated in a TSSM formulation buffer (as above). Vials of vector were thawed on wet-ice. If necessary, the vials of vector were thawed briefly (a few minutes) at room temperature. Once thawed the vial were briefly pulsed (5-10 seconds, 13,000 rpm) in a microfuge to ensure any vector article is collected from inside the lid/cap and suspended by gentle mixing by pipetting up and down about 3 times. Thawed vector was maintained on wet ice after thawing and used within 3 hours of removal from frozen storage. All dilutions of vector were made in to cell culture media.

T Cell Transduction and Expansion

Peripheral blood mononuclear cells (PBMCs) were collected by ficoll density centrifugation from patients with Ovarian cancer and frozen in aliquots. Upon defrosting of an aliquot, T cells from the PBMC were enriched by negative Isolation (Miltenyl Biotec) and mixed with the appropriate lentiviral vector, anti-CD3/CD28 dynabeads (Invitrogen, UK) and IL-2 (100 IU/mL; Novartis). T cells expanded in number over the next 7-14 days with fresh media and IL-2 added as required (generally every 2-3 days). Dynabeads were removed from the culture after 3-5 days by magnetic separation. Days 1-7 have 300 IU/mL IL2 reduced to 100 IU/mL for the remaining days. At the end of culture, cells were harvested by centrifugation, dead cells removed by ficoll density centrifugation and viable cell numbers determined by trypan blue exclusion and haemocytometer counts.

As shown in FIG. 7, transduction levels of PBMCs derived from ovarian cancer patients (Panel A) are comparable to transduction of healthy donors Panel B when using either the H8 or the 2E4 CAR constructs.

Assessment of CAR-T Cell Functionality

In vitro functionality assays involved co-culture of CAR-T cell populations with matched target tumour cells at a 1:1 ratio in 200 μL of media in individual wells of a 96 well plate. Simultaneously, CAR-T cells were cultured alone (negative control) and with 50 ng/mL PMA and 1 μg/mL Ionomycin (positive control). Following 24 hours incubation at 37° C., supernatant was collected and cytokines production measured. IFNγ and IL-2 production will be measured using the IFNγ and the IL-2 ELISA kits (both Diaclone, France), according to the manufacturer's instructions.

FIG. 9 shows that patient's CAR-T 5T4 cells secrete IFNγ in response to co-culture with SKOV-3 and OVCAR-3 cell lines as well as their own (autologous) tumour disaggregates.

Example 5. In Vivo Efficacy Against Ovarian Cancer Model

The following example focused upon testing of the 5T4 specific CARs against SKOV-3 tumours established in the NSG mouse. Buffy coats obtained from NHSBT were used as a source of peripheral blood mononuclear cells (PBMC). CD3+ T cells were isolated by negative isolation (Miltenyi Biotec), activated with dynabeads and transduced with pre-tested quantities of lentivirus vector encoding either the anti-5T4(H8).CD28.CD3ζ (5T4.CD28ζ) or anti-5T4(H8).4-1BB.CD3ζ (5T4.4-1BBζ) CARs. The transduced cells were then expanded in vitro prior to analysis for CAR expression and in vitro function before intravenous infusion into NSG mice bearing established SKOV-3.Luc tumours. This is further detailed below.

In Vitro Generation of CAR T Cells.

Buffy coat (BC) 92 and 102 were used to source T cells. From BC92, T cell isolation resulted in an increase of CD3+ T cell frequency from 53 to 83% with a reduction in the frequency of CD14+ myeloid cells (14 to 2.4%) and CD19+ B cells (12.3 to 0.7%). From BC108, CD3+ T cells were enriched from 36.6 to 81.5% with CD14+ myeloid cells and CD19+ B cells each reduced to a relative frequency of less than 1% (CD14+ 28.3 to 0.9%; CD19+ 22.7 to 0.5%).

Approximately 1-1.5×10$^6$ CD3+ T cells were used to establish the initial transduction culture involving Dynabeads™ (ThermoFisher) (1:1 ratio), IL-2 (100 IU/mL) and lentiviral vector. After seven days, Dynabeads™ (ThermoFisher) were removed from the culture, cells counted and approximately 0.5×10$^6$ cells used for rapid expansion (culture with irradiated feeder cells from three allo-donors, anti-CD3, anti-CD28 and 300 IU/mL of IL-2 reducing to 100 IU/mL after seven days of culture) for two weeks. At this point, T cells were collected, ficolled, washed and counted. In each case, a minimum expansion of 200 fold was observed for each culture (Mock, 5T4.CD28ζ, 5T4.4-1BBζ) with >10$^8$ total cells generated.

In Vivo Testing of 5T4 CAR T Cells.

Initial in vivo testing of the 5T4 CARs followed a design previously used in our group for other CAR/TCR models. In brief, approximately $2.5 \times 10^6$ SKOV3.Luc cells were injected by the intraperitoneal route into recipient NSG (NOD/SCID IL-2R$\gamma^{-/-}$) mice and seven days later, CAR-T cells were infused by the IV route (approximately $2 \times 10^7$ total cells). Animals were imaged by the Bruker system on day 6 (1 day prior to T-cell transfer) and then at regular times thereafter until approximately day 60 when the mice were sacrificed. This time point was chosen as our previous work has shown that NSG mice begin to develop symptoms of xenograft versus host disease (xGvHD) approximately 50-60 days after human T-cell transfer as a result of the human T-cells recognising mouse tissue antigens.

Bruker imaging clearly showed that mice receiving saline or $2 \times 10^7$ control, non-transduced mock T-cells from the same buffy coat had an increasing level of luminescence. This correlated with saline and Mock T cell treated animals all succumbing to tumour within 45 days of tumour administration. In one set of samples, no increase in luminescence was observed for both 5T4 CAR-T cell groups and these mice all survived through to the day 60 end point with no evidence of tumour. In another set of samples, there did appear to be a small increase in luminescence in mice receiving 5T4.4-1BBζ CAR-T cells as compared to 5T4.CD28ζ CAR-T cells and one animal in the 5T4.4-1BBζ tumour group succumbed to tumour before the day 60 endpoint. No animals succumbed to tumour in the 5T4.CD28ζ CAR treatment group.

FIG. 10 shows the survival of NSG mice treated with 5T4 CAR T cells compared to control groups receiving saline or mock transduced T cells.

Combining the survival of all experiments, both 5T4.CAR T cell treated groups had highly significant differences in survival when compared against saline and mock treated animals ($p<0.001$, Log Rank test).

Example 6. Minimum Dose and Delivery Route Requirements Against Ovarian Cancer Model This study was designed to estimate the minimum dose of 5T4-CAR transduced T cells required to demonstrate efficacy in a murine NSG mouse model bearing an Ovarian (SKOV-3) tumour cell line (as shown above).

In addition, this study also compared intra-venous with intra-peritoneal routes of delivery of CAR-T cells.

Transduction

The following vectors were used in this study

| Test Article | Batch No. | Strength (DNA) Titre (TU/mL) | RNA Titre (Copies/mL) | Sterility | Mycoplasma | Endotoxin |
|---|---|---|---|---|---|---|
| CMV-5T4(H8)-CAR-CD3ζ/CD28 | 5T4180714CD28 | $2.3 \times 10^8$ | $3.8 \times 10^{11}$ | Pass | Negative | Pass |
| CMV-5T4(H8)-CAR-CD3ζ/4-1BB | 5T425071441 BB | $3.5 \times 10^7$ | $4.5 \times 10^{12}$ | Pass | Negative | Pass |

Transduction was performed similarly to the protocol described above. In brief: peripheral blood mononuclear cells (PBMCs) were collected by ficoll density centrifugation from normal healthy donors (buffy cones supplied from the NHS BT or blood donations from volunteers) and frozen in aliquots. Upon defrosting of an aliquot, T cells from the PBMC were enriched by negative isolation (Miltenyi Biotec) and mixed with the appropriate lentiviral vector, anti-CD3/CD28 Dynabeads™ (Invitrogen, UK) and IL-2 (100 IU/mL; Novartis). T cells were expanded over the next 7-14 days with fresh media and IL-2 added as required (generally every 2-3 days). Dynabeads™ were removed from the culture after 3-5 days by magnetic separation. If larger number of T cells were required, a rapid expansion protocol involving irradiated feeder cells (3 donor PBMC from frozen, allogeneic NHSBT buffy cones were pooled and irradiated (25Gγ, Paterson Building X-ray source) cultured with CART cells at a ratio of 100 feeder cells:1 CART cell and mitogenically stimulated with anti-CD3 (OKT3; orthoclone, Janssen Cilag) and CD28 (R&D systems) anti bodies at 30 ng/ml plus IL-2 (Chiron, Amsterdam), feeding with IL-2 every other day for 14 days. Days 1-7 have 300 IU/mL IL-2 reduced to 100 IU/ml for the remaining period. At the end of culture, cells were harvested by centrifugation, dead cells removed by ficoll density centrifugation and viable cell numbers determined by trypan blue exclusion and haemocytometer counts.

| Minimum Dose Study groups | | |
|---|---|---|
| Group | No. Mice | Treatment (IV Administration) |
| 1 | 3 | $1 \times 10^7$ 5T4-CAR-CD3ζ/CD28 |
| 2 | 3 | $3 \times 10^6$ 5T4-CAR-CD3ζ/CD28 |
| 3 | 3 | $1 \times 10^6$ 5T4-CAR-CD3ζ/CD28 |
| 4 | 3 | $0.3 \times 10^6$ 5T4-CAR-CD3ζ/CD28 |
| 5 | 3 | $2 \times 10^7$ Mock-Transduced T cells |
| 6 | 3 | Saline |
| 7 | 3 | $1 \times 10^7$ 5T4-CAR-CD3ζ/4-1BB |
| 8 | 3 | $3 \times 10^6$ 5T4-CAR-CD3ζ/4-1BB |
| 9 | 3 | $1 \times 10^6$ 5T4-CAR-CD3ζ/4-1BB |
| 10 | 3 | $0/3 \times 10^6$ 5T4-CAR-CD3ζ/4-1BB |

Study Protocol to Assess Minimum Dose

1. Day 0: Inject $2.5 \times 10^6$ SKOV-3 Luc cells intra-peritoneal (IP) in 100 μL saline.
2. Day 7: Infuse 5T4 CAR-T cells by the intra-venous (IV) route in 100 μL saline (See above table for dose; control animals to receive $2 \times 10^7$ mock transduced cells and saline only)
3. Days 6, 13, 20, 27, 34, 41 and 48: IVIS imaging of tumours using Lumina system
4. Days 14, 21, 28 and 60: Tail bleeds taken to analyse T-cell engraftment.

Day 60: Experimental endpoint. Where possible, tissue will be collected from animals that have developed tumour.

| Route of administration study groups | | | |
|---|---|---|---|
| Group | No. Mice | Route | Treatment (IV Administration) |
| 1 | 3 | IV | $1 \times 10^7$ 5T4-CAR-CD3ζ/CD28 |
| 2 | 3 | IP | $1 \times 10^7$ 5T4-CAR-CD3ζ/CD28 |
| 3 | 3 | IP | $1 \times 10^6$ 5T4-CAR-CD3ζ/CD28 |
| 4 | 3 | IP | $1 \times 10^7$ Mock-Transduced T cells |
| 5 | 3 | IP | $1 \times 10^7$ Mock-Transduced T cells |
| 6 | 3 | IP | Saline |
| 7 | 3 | IV | $1 \times 10^7$ 5T4-CAR-CD3ζ/4-1BB |
| 8 | 3 | IP | $1 \times 10^7$ 5T4-CAR-CD3ζ/4-1BB |
| 9 | 3 | IP | $1 \times 10^6$ 5T4-CAR-CD3ζ/4-1BB |

Study Protocol to Assess Route of Administration

1. Day 0: Inject $2.5 \times 106$ SKOV-3 Luc cells i.p in 1001-11 saline.
2. Day 7: Infuse 5T4 CART-cells by the intra-peritoneal (i.p.) or i.v. route (See Table 3 for dose
  details; control animals to receive $2 \times 107$ mock transduced cells and saline only)
3. Days 6, 13, 20, 27, 34, 41 and 48: IVIS imaging of tumours using Lumina system
4. Days 14, 21, 28 and 60: Tail bleeds taken to analyse T-cell engraftment.
5. Day 60: Tissue collected and available for IHC to determine 5T4 expression and also to interrogate for 5T4 CAR. Terminal bleeds collected and analysed by flow cytometry for 5T4 CAR-T cells. Where CAR-T cells are present to sufficient numbers, in vitro assessment of engrafted CAR-T cell function to be assessed by in vitro co-culture with 5T4+ and 5T4-target cells for cytokine production (either by ELISA of culture supernatants or intracellular flow cytometry).

Results for Minimal Efficacious Dose

It was clear in this experiment from the bioluminescence that SKOV3.Luc tumour bearing NSG mice were effectively protected against tumour growth by doses of 5T4.CD28ζ CAR-T cells to a dose of $0.1 \times 10^7$ T cells which equates to a dose of $2.2 \times 10^5$ CAR-T cells. It was also clear that all mice in the 5T4.4-1BBζ CART cell group developed tumour by the end of the experimental time point.

The median survival of mice In the saline and mock T cell groups were both 56 days as compared to 95 days for the lowest T cell dose in the 5T4.CD28ζ CART cell group and 86 days in the $0.3 \times 10^7$ 5 T4.CD28ζ CART cell group although the latter was affected by non-tumour related events. A median survival for the remaining 5T4.CD28ζ CART cell groups could not be determined due to the high survival in each of these experimental groups (FIG. 11). In comparison, the highest 5T4.4-1BBζ T cell dose ($10^7$ T cells equating to $7.6 \times 10^5$ CAR-T cells), showed an improved level of survival against controls with a median survival of 116 days achieved with one animal remaining alive but with significant tumour load at the end of the experiment. A delay in tumour growth was observed in the $0.3 \times 10^7$ T cell group ($2.3 \times 10^5$ CART cells; median survival 78 days) but no effective anti-tumour response observed in the two lowest CAR-T cell groups ($0.1 \times 10^7$ total cells equating to $7.6 \times 10^4$ CAR-T cells and $0.03 \times 10^7$ total cells equating to $2.3 \times 10^4$ CAR-T cells).

Overall, this experiment demonstrated that as few as $2.2 \times 10^5$ 5 T4.CD28ζ CAR-T cells delivered a significant in vivo anti-tumour effect. The survival of mice with established SKOV-3 tumours was enhanced by therapy with $7.6 \times 10^5$ 5 T4.4-1BBζ CAR-T cells although this dose of CART cells failed to eradicate all tumour in this specific experiment.

Results for Route of Administration

The bioluminescence images (FIG. 12) showed that SKOV3-Luc tumour growth was controlled in mice receiving the high dose of 5T4.CD28ζ CAR-T cells by the IV or IP route ($1 \times 10^7$ total T cells which was equivalent to $6.5 \times 10^5$ CAR+ T cells). There was a clear delay in tumour growth in both IV and IP treated animals receiving $10^6$ 5 T4.CD28ζ CAR-T cells (equivalent to $6.5 \times 10^4$ CAR+ T cells) but tumour did develop in these animals resulting in deaths in each group before the end of the experiment ($1 \times 10^7$ total T cells which was equivalent to $6.5 \times 10^5$ CAR+ T cells). For animals receiving 5T4.4-1BBζ CAR-T cells, there was a reduced level of protection against tumour growth with the highest dose of CAR-T cells unable to prevent tumour growth in all animals ($1 \times 10^7$ total T cells which was equivalent to $2.6 \times 10^5$ CAR+ T cells). Control animals all succumbed to tumour growth within 74 days.

The combined group luminescence analysis clearly shows the anti-tumour potency of $10^7$ 5 T4.CD28ζ CAR-T cells given by either route with a suggestion of a transient response by the local IP infusion of $10^6$ 5 T4.CD28ζ CAR-T cells although by day 28, the level of tumour growth in both IP and IV $10^6$ 5 T4.CD28ζ CAR-T cell groups appears to be equivalent.

Importantly, all 5T4.CD28ζ CAR T cell groups showed a statistically significant degree of tumour growth as compared to control groups but there was no statistical difference seen between the therapy groups that were most likely due to the small group size in this proof of principle experiment. In contrast, only the highest dose of 5T4.4-1BBζ CAR-T cells had any significant effect upon SKOV-3-Luc tumour growth with a clear reduction in tumour growth for approximately three weeks before evidence of tumour growth by day 28. However, the individual tumour growth curves paint a slightly more complicated story as compared to the whole population where tumour growth was controlled and indeed decreased in two animals at later time points with one animal clearly developing tumour that resulted in cull around day 80. This delayed anti-tumour kinetics of 4-1BBζ CAR activity in comparison to the relatively rapid anti-tumour activity of the CD28-based CAR has been described in a recent publication from the Sadelain Lab (Zhao et al. (2015) Cancer Cell 28(4): 415-428).

These observations of anti-tumour effect mediated by the CD28 based CARs translated to improved survival over control animals while only the $10^6$ 5 T4.4-1BBζ IP showed significant improvement in survival against control groups although the loss of one animal in the higher dose IP group impacted upon the survival analysis in this experiment.

Overall, this study suggests that CAR-T cells infused by either the IP or IV route of administration show equivalent relative efficacy.

Example 7. Comparison Between CAR-T Cells Bearing H8 and 2E4α-5T4 Antibodies

This study was conducted to determine whether there any evidence of superior efficacy when comparing constructs which use different 5T4 scFvs (EF1α-H8-CAR-CD3ζ/4-

1BB or EF1α-2E4-CAR-CD3ζ/4-1BB) in the SKOV-3 ovarian cancer model.

The vectors used in this study are shown below

| Test Article | Batch No. | Strength (DNA) Titre (TU/ml*) | RNA Titre (copies/ml) | Sterility | Mycoplasma | Endotoxin |
|---|---|---|---|---|---|---|
| EF1α-H8-CAR-CD3ζ/4-1BB | C/23/10/2015/H8-41BB | 1.8E+08 | 6.2E+11 | Pass | Negative | Pass |
| EF1α-2E4-CAR-CD3ζ/4-1BB | C/16/10/2015/2E4-41BB | 2.9E+08 | 1.3E+12 | Pass | Negative | Pass |
| CMV-5T4-CAR CD3ζ/4-1BB | 5T425071441BB | 3.5E+07 | $4.5 \times 10^{11}$ | Pass | Negative | Pass |
| HIV-Luc-i-GFP Vector | N/A | 5.85E+05 | Not Tested | Not Tested (0.22 μm filtered) | Not Tested | Not Tested |

T-cell transduction was performed as described above.

Treatment Groups for SKOV-3/NSG Tumour Model

| Animal Group Number | Treatment | Route of Administration of T cells | Tumour Cell Challenge Route | No. of animals/group |
|---|---|---|---|---|
| 1 | $1 \times 10^7$ mock-transduced T cells | I.V. | I.P. | 5 |
| 2 | $1 \times 10^7$ PBMCs transduced with CMV-H8-CAR-CD3ζ/4-1BB | I.V. | I.P. | 5 |
| 3 | $1 \times 10^7$ transduced with EF1α-H8-CAR-CD3ζ/4-1BB | I.V. | I.P. | 5 |
| 4 | $1 \times 10^7$ transduced with EF1α-2E4-CAR-CD3ζ/4-1BB | I.V. | I.P. | 5 |

Results

The 5T4-specific response of each cell population was assessed by co-culture with SKOV-3 tumour cells. All 5T4-CAR T cell populations produced IFNγ and IL-2 above the background level of cytokine production of the mock transduced T cells. Furthermore, it appeared that the constructs containing the EF1α promoter compared to the CMV promoter yielded higher cytokine levels. However, due to the lack phenotyping data for the CMV group, it is impossible to rule out the possibility that the number of CAR+ T cells was lower in the CMV group compared to the EF1α groups and therefore explaining the lower cytokine release. The same explanation does not hold for the comparison of H8 and 2E4 constructs where the percentage of 2E4 transduced T cells is higher (29%) than for the H8 construct (12.9%), but the level of cytokine secretion is lower.

Assessment of 5T4 CAR-T cell efficacy against SKOV-3 cell challenge was subsequently tested in vivo in NSG mice (treatment groups as listed above). Bioluminescence showed that the SKOV3 tumour burden was comparable across groups on day 7 (the day of CAR-T cell administration) and that a retardation of tumour growth was seen in the EF1α-2E4-CAR-CD3ζ/4-1BB (2E4-EF1α) and EF1α-H8-CAR-CD3ζ/4-1BB (H8-EF1α) treated animals, but not the CMV-H8-CAR-CD3ζ/4-1BB group.

Overall, as highlighted in FIG. 13, there was a statistically significant increase in survival with EF1α-H8-CAR-CD3ζ/4-1BB T-cells compared to EF1α-2E4-CAR-CD3ζ/4-1BB T-cells (P=0.008, Log-rank, Mantel-Cox test). Based upon the transduction efficiency reported in Table 5, $10^7$ target dose of T cells contained $2.9 \times 10^6$ CAR+ cells transduced with EF1α-2E4-CAR-CD3ζ/4-1BB and $1.29 \times 10^6$ CAR+ cells transduced with EF1α-H8-CAR-CD3ζ/4-1BB. As such, the superior efficacy seen with the H8 construct was not expected based on CAR+ T cell dose alone, suggesting that the construct itself is more potent than the 2E4-CAR-CD3ζ/4-1BB equivalent in this model.

Example 8: In Vivo Efficacy Against Myeloma Cancer Model

Treatment Groups for assessment of 5T4 CAR-T cell efficacy against a myeloma cell line

| Animal Group No. | Treatment (Total number of T cells) | Route of CART Cell Administration | Cell Line | Tumour Challenge Route (Cell Number) | No. of animals/group |
|---|---|---|---|---|---|
| 7 | $1 \times 10^7$ mock-transduced T cells | I.V. | NC1-H929 (myeloma) | I.P. ($2 \times 10^6$) | 5 |

-continued

Treatment Groups for assessment of 5T4 CAR-T cell efficacy against a myeloma cell line

| Animal Group No. | Treatment (Total number of T cells) | Route of CART Cell Administration | Cell Line | Tumour Challenge Route (Cell Number) | No. of animals/group |
|---|---|---|---|---|---|
| 8 | $1 \times 10^7$ transduced with EF1α-H8-CAR-CD3ζ/4-1BB | I.V. | NCI-H929 (myeloma) | I.P. ($2 \times 10^6$) | 5 |
| 9 | $1 \times 10^7$ transduced with EF1α-2E4-CAR-CD3ζ/4-1BB | I.V. | NCI-H929 (myeloma) | I.P. ($2 \times 10^6$) | 5 |
| 10 | $1 \times 10^7$ mock-transduced T cells | I.V. | NCI-H929 (myeloma) | I.V. ($2 \times 10^6$) | 5 |
| 11 | $1 \times 10^7$ transduced with EF1α-H8-CAR-CD3ζ/4-1BB | I.V. | NCI-H929 (myeloma) | I.V. ($2 \times 10^6$) | 5 |
| 12 | $1 \times 10^7$ transduced with EF1α-2E4-CAR-CD3ζ/4-1BB | I.V. | NCI-H929 (myeloma) | I.V. ($2 \times 10^6$) | 5 |

Results

As detailed in the above table, NSG mice were challenged with $2 \times 10^6$ NCI-H929 cells via the I.P. or I.V. route of administration. 7 days post tumour challenge, mice were treated with $1 \times 10^7$ CAR-T cells via the I.V. route of administration. Based on the phenotype of transduced T cells, a dose of $5.98 \times 10^6$ CAR$^+$ T cells transduced with EF1α-H8-CAR-CD3ζ/4-1BB were delivered and $3.86 \times 10^6$ CAR$^+$ T cells transduced with EF1α-2E4-CAR-CD3ζ/4-1BB.

Following IV challenge with the NCI-H929 myeloma cell line (which expresses low levels of 5T4), mice treated with EF1α-H8-CAR-CD3ζ/4-1BB transduced T cells showed statistically significant improvement in survival relative to animals treated with mock transduced T cells or EF1α-2E4-CAR-CD3ζ/4-1BB transduced T cells (P=0.0018 and P=0.034 respectively; see FIG. 14).

Example 9—Expression of 5T4 in Myeloma Cells

5T4 expression was examined by FACS using Oxford BioMedica's anti-5T4 H8 monoclonal antibody and immunohistochemistry was performed using the anti-5T4 antibody from R&D Systems according to the following methods:

Assessment of 5T4 Expression by Flow Cytometry

The antibody used for tumour cell flow cytometry was the anti-5T4 H8 murine monoclonal antibody; this was used as a directly PE-conjugated antibody. The antibody was titrated to determine the optimum concentration for detection of cell surface expression of 5T4 on the tumour cell lines. The concentrations used ranged from 25 µg/ml down to 0.5 µg/ml. The antibody was diluted in FACS buffer (BD Biosciences; Oxford, UK). A mouse IgG1 isotype control (BD; Oxford, UK; conjugated as appropriate) was used as a negative control. After counting the cells were re-suspended in PBS to a concentration of $1 \times 10^6$ cells/ml. 500 µl of cell suspension was added to each FACS tube and the cells were washed in PBS at a total volume of 4 ml. The diluted antibody were then added to the pelleted cells and incubated for 30 minutes at +4° C. If a secondary antibody was added the cells were washed in PBS as above, the antibody added and the cell incubated for 30 minutes at +4° C. The cells were then washed again in 1 ml PBS and fixed with Cytofix (BD Biosciences; Oxford, UK). The data was acquired on a BD FACSVerse (BD Biosciences; Oxford, UK) and analysed on FACSuite software (BD Biosciences; Oxford, UK).

The optimum antibody concentration for 5T4 staining was found to be 2.5 µg/mL; this concetration was used in all subsequent experiments.

Assessment of 5T4 Expression by Immunophistochemistry

FFPE sections were dewaxed by washing 3× in 100% xylene for 5 min each time

FFPE sections were rehydrated by washing for 5 min each in 100%, 92% & 70% ethanol Sections were then placed in dH2O for 5 min Antigen retrieval was performed by incubating the sections first in 1× antigen retrieval solution (Dako) for 30 min at 95° C. in a heated waterbath & then in fresh 1× antigen retrieval solution for 20 min at room temperature Sections were then placed in dH2O for 5 min Sections were blocked in blocking solution (PBS with 1% BSA & 2% FBS) for 1 h at room temperature Blocking buffer was removed the Dako amplification kit was used according to the manufacturers instructions using the maximum number & length of washes stated in the protocol 5T4 antibody (R&D) was used as 25 µg/ml & the concentration matched by an IgG1 control (ebioscience)

Sections were then counterstained with Haematoxylin for 1 min then washed 3× in dH2O for 5 min each time Sections were dehydrated by washing for 5 min each in 70%, 92% & 100% ethanol Sections were washed 3× for 5 min each in 100% xylene Sections were mounted with DPX Sections were then scanned using the Mirax Scanner and images processed using the Panoramic Viewer software The FACS results are shown in FIG. 15. 5T4 expression was detected by FACS in 3 of 5 multiple myeloma cell lines tested: Myeloma cell lines JJN3, RPMI-8229 and H929 were positive for 5T4 expression. U266 and THEIL cell lines were negative by FACS. MFC7 breast cancer cells were used as a positive control.

Using immunohistochemical staining 5T4 expression was detected in the JJN3, RPMI-8226 and H929 myeloma cell lines. H929 was used in the studies described above.

The results are shown in FIG. 16. Figure Panel A and B represent negative (CHO cells stained for 5T4) and positive (CHO cells stably expressing 5T4 and stained for 5T4 expression) controls respectively. FIG. 16 Panel C shows MCF7 breast cancer cells stained for 5T4 expression. FIG. 16 Panel D shows H929 myeloma cells stained for 5T4 expression.

Example 10—Expression of 5T4 in Human Myeloma Samples

5T4 expression, in myeloma samples recovered from patients, was examined by immunohistochemistry using the anti-5T4 antibody from R&D Systems according to the following methods Sections (4 μm) from FFPE blocks of colon, placenta and multiple myeloma were prepared using a Leica microtome. All reagents used were part of the EnVision™ FLEX+ kit (Dako, K8012) unless otherwise stated.

Sections were subjected to antigen retrieval at pH6.1 in a Dako PT Link chamber at 97° C. for 20 minutes, using Envision™ FLEX Target Retrieval Solution. Following antigen retrieval at pH 6.1, sections were placed in Envision Flex Wash Buffer (pH 7.6, Dako, #K8007) for 5 minutes, before being loaded onto a Dako Autostainer Plus. Sections were then incubated for 5 minutes with Envision Flex Peroxidase blocking reagent, and then washed twice with Flex Wash buffer. Subsequently, sections were incubated for 10 minutes with serum free protein block reagent (Dako, #X0909), which was removed by air-jet.

All sections were incubated with primary antibody or in the absence of primary antibody for 30 minutes. The anti-5T4 antibody was applied at 3.125 μg/ml, and a concentration and species matched non-immune mouse IgG1 was used as an isotype control antibody. Assay reagents were validated by incubation of sections of colon with an antibody against pancytokeratin (PCK).

After incubation with primary antibodies, sections were washed twice with Flex Wash buffer, incubated with Flex HRP polymer for 20 minutes, then washed twice with Flex Wash buffer. All sections were then incubated with diaminobenzidine (DAB) substrate for 10 minutes, and then washed with distilled water.

Sections were counterstained with haematoxylin, dehydrated in an ascending series of ethanols (90-99%), cleared in three changes of xylene and cover-slipped under DePeX. Digital images were captured using an Aperio ScanScope AT Turbo digital scanner and analysed by research staff and consultant pathologist to assess 5T4 immunoreactivity.

Of 16 samples assessed for 5T4 expression two showed occasional weak 5T4-immunoreactive myeloma cells. One sample showed a weak-moderate immunostain and a fourth sample demonstrated moderate immunostaining in the cytoplasm and on the plasma membrane of tumour cells. Overall 4 samples were 5T4-immunoreactive (FIG. 17) and the remaining 12 samples were negative for 5T4, representing 25% positivity for 5T4.

Example 11—Expression of 5T4 in Haematological Cancers

Material and Methods

Assessment of 5T4 Expression on Haematological Malignancies

5T4 expression on haematological malignancies was assessed by flow cytometry using a FACS machine as described below.

Liquid Tumour Samples

Samples of bone marrow cells or peripheral blood mononuclear cells (PBMCs) were selected from patients with the following haematological malignancies:
  i. Multiple Myeloma,
  ii. Chronic Myeloid Leukaemia (CML)
  iii. Chronic Lymphocytic Leukaemia (CLL)
  iv. Acute Myeloid Leukaemia (AML)
  v. B-cell acute Lymphoblastic Leukaemia (B-ALL)
  vi. T-cell Acute Lymphoblastic Leukaemia (T-ALL)
  vii. Acute Promyelocytic Myeloid Leukaemia (APML).

These samples were acquired from Tissue Solutions Ltd., Histologix Ltd. and the Manchester Cancer Research Centre (MCRC) Biobank.

Assessment of 5T4 Expression on Haematological Malignancies: Staining Protocol and Gating Strategy Vials of cells were thawed and re-suspended in RPMI-1640 media supplemented with 10% FBS, 5 mM L-glutamine, 100 U/mL penicillin/100 μg/mL streptomycin. Following this, cells were washed and re-suspended in PBS. Cells were divided equally into the relevant number of FACS tubes for the samples being analysed. Cells were then incubated with Zombie Aqua™ as per manufacturer's protocol. Following incubation, cells were washed in BD FACS Stain Buffer (catalogue number 554656). All patient samples were stained using a custom conjugated 5T4-PE antibody obtained from APS and co-stained with various tumour markers as described in the respective sections below for 30 minutes to 1 hour at +2° C. to +8° C. Cells were washed twice with stain buffer following incubation and re-suspended in BD CytoFix (554655) as per manufacturer's protocol. Cells were then pelleted and re-suspended in PBS.

Acquisition was performed on a FACSVerse flow cytometer (BD Biosciences). In each case, 10,000 events in the Live Cell gate were acquired. Data analysis was performed using FlowJo version 10.

For the exclusion of dead cells, where present, the Zombie Aqua™ fixable viability kit (BioLegend) was used. Cell debris was further excluded based on Forward versus Side scatter (FSC/SSC).

Results

Peripheral blood or bone marrow samples recovered from patients with CLL, multiple myeloma, B-ALL, AML, CML, APML and T-ALL were assessed for 5T4 expression by flow cytometry. Several lineage cell surface markers were used in order to help identify the malignant cell type amongst other non-malignant cells present in the samples as well as markers indicative of a cancer stem cell phenotype.

Overall findings from the study are summarised in the Table below. It can be seen that a 5T4 expression is seen in different haematological malignancies.

CD34 was used as the primary phenotypic marker to determine if 5T4 is expressed on CSCs. As shown in the Table below, 5T4 was found to be expressed in a number of cancer stem cells.

TABLE

5T4 Expression in Haematological Malignancies. The table shows the number of patient samples analysed for 5T4 expression by FACS along with the percentage of samples which were determined to be 5T4 positive and whether expression on cancer stem cells was detected.

| Cancer | Total number of samples | Number (%) 5T4 Positive | Expression on Cancer Stem Cells |
|---|---|---|---|
| Chronic Lymphocytic Leukaemia | 11 | 11 (100%) | Yes |
| Multiple Myeloma | 31 | 22 (71%) | Yes |
| Acute Myeloid Leukaemia | 36 | 17 (47%) | Yes |
| B Cell Acute Lymphoblastic Leukaemia | 21 | 8 (38%) | Yes |
| Chronic Myeloid Leukaemia | 7 | 1 (14%) | No |

TABLE-continued

5T4 Expression in Haematological Malignancies. The table shows the number of patient samples analysed for 5T4 expression by FACS along with the percentage of samples which were determined to be 5T4 positive and whether expression on cancer stem cells was detected.

| Cancer | Total number of samples | Number (%) 5T4 Positive | Expression on Cancer Stem Cells |
|---|---|---|---|
| T-Cell Acute Lymphoblastic Leukaemia | 11 | 1 (9%) | No |
| Acute Promyelocytic Myeloid Leukaemia | 9 | 0 (0%) | No |

Example 12—Assessment of 5T4 Expression on Cancer Stem Cells in Solid Tumour Cell Lines Solid Tumour Cell Lines The following cell lines were assessed for 5T4 expression following culture as a monolayer (standard cell culture conditions) or following sphere formation (enriched for CSCs):
i. OVCAR-3 (Ovarian Cancer)
ii. MCF7 (Breast Cancer)
iii. HCT116 (Colorectal Cancer)
iv. HT29 (Colorectal Cancer)
v. A549 (Lung Cancer)
vi. U251 (Glioblastoma)

Monolayer Cell Culture

HCT116, HT29, MCF7 and A549 cells were cultured in DMEM medium containing 10% foetal bovine serum (FBS), 2 mM L-glutamine and 50 µg/ml penicillin-streptomycin. OVCAR3 cells were cultured in RPMI medium containing 20% FBS, 10 µg/ml human insulin, 2 mM L-glutamine and 50 µg/ml penicillin-streptomycin. U251 cells were cultured MEM medium containing 10% FBS, 1% sodium pyruvate, 1% non-essential amino acids, 2 mM L-glutamine and 50 µg/ml penicillin-streptomycin. All cells were cultured at 37° C., 5% $CO_2$/95% air atmosphere, with 95% relative humidity.

Sphere Cell Culture

The method for sphere culture was adapted from Farnie et al. (2007) Journal of the National Cancer Institute 99, 616-627). Poly-HEMA was dissolved in 95% ethanol and added to cell culture flasks and then the ethanol was allowed to evaporate off overnight. HCT116 and HT29 cells were cultured in basic sphere medium (DMEM/F12, 100 IU/ml penicillin, 100 µg/ml streptomycin, 1×B27 supplement); MCF7, U251 and A549 cells were cultured in mammosphere medium (basic sphere plus 10 ng/ml hEGF, 5 µg/ml insulin, 0.5 µg/ml hydrocortisone) and OVCAR3 cells were cultured in ovarian sphere medium (basic sphere plus 20 ng/ml hEGF, 5 µg/ml insulin, 15 ng/ml hbFGF and 0.4% FBS).

Experimental Cell Culture and Flow Cytometry

Each cell line was cultured in two T75 flasks in monolayer conditions and four T175 flasks in sphere conditions as described above at 2000 cells per $cm^2$. After 24 hr, three sphere flasks and one monolayer flask of each cell line were harvested into single cell suspensions and labelled with 5T4-PE (5 µl per test) with or without CD133-APC (5 µl per test, eBioscience™, cat #17-1338-42) or CD117-APC (5 µl per test, eBioscience™, cat #17-1178-42). Corresponding isotype labelling was performed for each cell line and condition (IgG1-PE, 12.5 µl per test; and IgG1-APC, 5 µl per test, eBioscience™, cat #17-4714-82). Antibody labelling was performed in FACS buffer (PBS, 5% FCS, 100 IU/ml penicillin, 100 µg/ml streptomycin) on ice for 30 minutes in 96 well plates before wells were washed twice in FACS buffer. Flow cytometry was performed on a MACSQuant Analyzer 10, and analysis was performed using FlowJo V10.

The remaining monolayer flasks were kept in culture until cells reached at least 60% confluency ('bulk cells'), whilst the remaining sphere flasks were cultured for 7 days before harvest into single cell suspensions for flow cytometry. Antibody labelling was performed as described above.

Results

The results are shown in FIG. 19. The data in this study demonstrate that 5T4 is expressed on cancer stem cells for the cell lines studied. In addition, the consistent increases in MFI suggest a potential higher expression of 5T4 per cell on cancer stem cells.

All documents referred to herein are hereby incorporated by reference in their entirety, with special attention to the subject matter for which they are referred. Various modifications and variations of the described methods and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A 5T4-specific chimeric antigen receptor (CAR) comprising the amino acid sequence set out in SEQ ID NO: 1.

2. A nucleic acid molecule that comprises a nucleotide sequence encoding a 5T4-specific chimeric antigen receptor (CAR), said CAR comprising the amino acid sequence set out in SEQ ID NO: 1.

3. The nucleic acid molecule of claim 2, wherein the nucleic acid comprises a nucleotide sequence set out in SEQ ID NO: 9.

4. An immune cell that is a T cell, an NK cell, or an NKT cell and that expresses the 5T4-specific CAR according to claim 1.

5. A population of immune cells according to claim 4 in a pharmaceutical composition.

6. A vector containing the nucleic acid molecule according to claim 2 operably linked to a promoter.

7. The vector according to claim 6 that is a viral vector.

8. The vector according to claim 7 that is a lentiviral vector.

9. An immune cell that is a T cell, an NK cell, or an NKT cell that is transformed or transfected with the vector of claim 7.

10. The vector according to claim 6, wherein the nucleic acid molecule comprises the nucleotide sequence set out in SEQ ID NO: 9.

11. A method for treating a 5T4-expressing cancer in a human subject, the method comprising administering to a subject in need thereof a population of immune cells according to claim 5.

12. The method of claim 11, wherein the 5T4-expressing cancer is chronic lymphocytic leukaemia, myeloma, acute myeloid leukaemia, B cell acute lymphoblastic leukaemia, chronic myeloid leukemia, or T cell acute lymphoblastic leukaemia.

13. The method of claim 11, wherein the 5T4-expressing cancer is ovarian cancer or mesothelioma.

14. The method of claim 11, wherein the method further comprises administering to the subject a further cancer therapy.

15. A method of making an immune cell expressing a 5T4-specific chimeric antigen receptor (CAR), the method comprising transducing immune cells with the viral vector of claim 7.

16. The method according to claim 15, wherein the viral vector is a lentiviral vector and the promoter is the EF1α promoter set out in SEQ ID NO: 10.

17. A monoclonal antibody that binds human 5T4, wherein the antibody comprises the heavy (VH) and light (VL) variable fragments of the antibody that comprises the amino acid sequence set out in SEQ ID NO: 11.

18. A nucleic acid molecule comprising a nucleotide sequence encoding the VH and VL fragments of the monoclonal antibody of claim 17.

19. A 5T4-specific chimeric antigen receptor (CAR) comprising an extracellular ligand binding domain, a hinge, a transmembrane domain, and a cytoplasmic domain that includes a signaling domain and a co-stimulatory domain, wherein the ligand binding domain comprises the heavy (VH) and light (VL) variable fragments of an antibody that comprises the amino acid sequence set out in SEQ ID NO: 11.

20. The 5T4-specific CAR of claim 19, wherein said CAR comprises the amino acid sequence set out in SEQ ID NO: 13.

21. A nucleic acid molecule comprising a nucleotide sequence encoding the 5T4-specific CAR of claim 20.

22. An immune cell that is a T cell, an NK cell, or an NKT cell and that expresses the 5T4-specific CAR according to claim 19.

23. A population of immune cells according to claim 22 in a pharmaceutical composition.

24. An immune cell that is a T cell, an NK cell, or an NKT cell and that expresses the 5T4-specific CAR according to claim 20.

25. A vector containing the nucleic acid molecule according to claim 18 operably linked to a promoter.

26. A vector containing the nucleic acid molecule according to claim 21 operably linked to a promoter.

27. The vector according to claim 26 that is a viral vector.

28. The vector according to claim 27 that is a lentiviral vector.

29. An immune cell that is a T cell, an NK cell, or an NKT cell that is transformed or transfected with the vector of claim 27.

30. A method for treating a 5T4-expressing cancer in a human subject, the method comprising administering to a subject in need thereof a population of immune cells according to claim 23.

31. The method of claim 30, wherein the 5T4-expressing cancer is ovarian cancer, mesothelioma, chronic lymphocytic leukaemia, myeloma, acute myeloid leukaemia, B cell acute lymphoblastic leukaemia, chronic myeloid leukemia, or T cell acute lymphoblastic leukaemia.

32. The method of claim 30, wherein the method further comprises administering a further cancer therapy.

33. A method of making an immune cell expressing a 5T4-specific chimeric antigen receptor (CAR), the method comprising transducing immune cells with the vector of claim 27.

34. The method according to claim 33, wherein the viral vector is a lentiviral vector.

* * * * *